(12) United States Patent
Boudreault et al.

(10) Patent No.: US 9,799,838 B2
(45) Date of Patent: Oct. 24, 2017

(54) FLUORINATED ORGANIC ELECTROLUMINESCENT MATERIALS AND DEVICES

(71) Applicant: Universal Display Corporation, Ewing, NJ (US)

(72) Inventors: Pierre-Luc T. Boudreault, Pennington, NJ (US); Walter Yeager, Yardley, PA (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 15/177,906

(22) Filed: Jun. 9, 2016

(65) Prior Publication Data

US 2016/0285013 A1    Sep. 29, 2016

Related U.S. Application Data

(63) Continuation of application No. 14/509,274, filed on Oct. 8, 2014, now Pat. No. 9,397,302.

(51) Int. Cl.
*H01L 29/08* (2006.01)
*H01L 51/00* (2006.01)
(Continued)

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1029* (2013.01); *C09K 2211/1033* (2013.01); *C09K 2211/1044* (2013.01); *C09K 2211/185* (2013.01); *H01L 51/5016* (2013.01);
(Continued)

(58) Field of Classification Search
CPC ............ H01L 51/0085; H01L 51/5016; C07F 15/0033
USPC .......................................................... 257/40
See application file for complete search history.

(56) References Cited

U.S. PATENT DOCUMENTS 4,769,292 A    9/1988  Tang et al.
5,061,569 A    10/1991 VanSlyke et al.
(Continued)

FOREIGN PATENT DOCUMENTS

CN    103694277     4/2014
DE    102010009193  8/2011
(Continued)

OTHER PUBLICATIONS

Extended European Search Report issued on Mar. 1, 2016 for corresponding EP Patent Application No. 15185414.8.
(Continued)

*Primary Examiner* — Caleb Henry
(74) *Attorney, Agent, or Firm* — Duane Morris LLP

(57) ABSTRACT

Novel ligands for metal complex compounds that are useful as a phosphorescent emitter in organic light emitting devices that incorporate fluorinated side chains in the ligands are disclosed. Such metal complex has at least one substituent R selected from the group consisting of partially fluorinated alkyl, partially fluorinated cycloalkyl, and combinations thereof, wherein R is directly bonded to an aromatic ring, In the compound, C having an F attached thereto is separated by at least one carbon atom from the aromatic ring.

19 Claims, 2 Drawing Sheets

(51) Int. Cl.
*C07F 15/00* (2006.01)
*C09K 11/06* (2006.01)
*H01L 51/50* (2006.01)
*H01L 51/52* (2006.01)

(52) U.S. Cl.
CPC ...... *H01L 51/5024* (2013.01); *H01L 51/5206* (2013.01); *H01L 51/5221* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,164,045 B2 * | 1/2007 | Grushin ............... C07F 9/5004 568/429 |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,816,016 B1 | 10/2010 | Herron et al. |
| 8,071,975 B2 * | 12/2011 | LeCloux ............... C07C 211/49 136/263 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0228583 A1 * | 10/2006 | Kamatani ............ C07F 15/004 428/690 |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0228940 A1 * | 10/2007 | Hashimoto ......... C07F 15/0033 313/504 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0038586 A1 | 2/2008 | Nishizeki et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0073849 A1 * | 3/2011 | Knowles ............. C07F 15/0033 257/40 |
| 2013/0200349 A1 * | 8/2013 | Soga .................... C08G 61/10 257/40 |
| 2014/0138663 A1 | 5/2014 | Aratani et al. |
| 2014/0364611 A1 * | 12/2014 | Mak .................... C07F 15/0033 546/4 |

FOREIGN PATENT DOCUMENTS

| | | |
|---|---|---|
| EP | 0650955 | 5/1995 |
| EP | 1725079 | 11/2006 |
| EP | 2034538 | 3/2009 |
| EP | 2182002 | 5/2010 |
| JP | 200511610 | 1/2005 |
| JP | 2007123392 | 5/2007 |
| JP | 2007254297 | 10/2007 |
| JP | 2008074939 | 4/2008 |
| KR | 20140060974 | 5/2014 |
| WO | 01/39234 | 5/2001 |
| WO | 02/02714 | 1/2002 |
| WO | 0215654 | 2/2002 |
| WO | WO0244189 | 6/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |

(56) References Cited

FOREIGN PATENT DOCUMENTS

| | | |
|---|---|---|
| WO | 2009086028 | 7/2009 |
| WO | 2009100991 | 8/2009 |
| WO | 2015000955 | 1/2015 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NΛCΛN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

(56) References Cited

OTHER PUBLICATIONS

Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

FLUORINATED ORGANIC ELECTROLUMINESCENT MATERIALS AND DEVICES

CROSS-REFERENCE TO RELATED APPLICATIONS

This application is a continuation of U.S. patent application Ser. No. 14/509,274, filed on Oct. 8, 2014.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel ligands for metal complexes for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

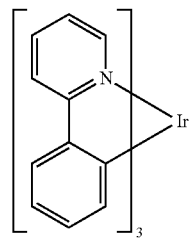

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

This invention discloses novel ligands for metal complexes that are useful as a phosponrescent emitter in organic light emitting device. Applicant believes that incorporation of the new side chains on the ligands allow the fine tuning of emission color of the metal complex while maintaining good device efficiency and device lifetime.

According to an embodiment, a composition comprising a novel compound is disclosed, wherein the compound is capable of functioning as a phosphorescent emitter in an organic light emitting device at room temperature. The compound has at least one aromatic ring and at least one substituent R, wherein each of the at least one R is independently selected from the group consisting of partially fluorinated alkyl, partially fluorinated cycloalkyl, and combinations thereof; wherein each of the at least one R is directly bonded to one of the aromatic rings, wherein in each of the at least one R, C having an F attached thereto is separated by at least one carbon atom from the aromatic ring.

According to another embodiment, a first device comprising a first organic light emitting device is also provided. The first organic light emitting device can include an anode, a cathode, and an organic layer, disposed between the anode and the cathode. The organic layer can include the compound having at least one aromatic ring and at least one substituent R, wherein each of the at least one R is independently selected from the group consisting of partially fluorinated alkyl, partially fluorinated cycloalkyl, and combinations thereof; wherein each of the at least one R is directly bonded to one of the aromatic rings, wherein in each of the at least one R, C having an F attached thereto is separated by at least one carbon atom from the aromatic ring. The first device can be a consumer product, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
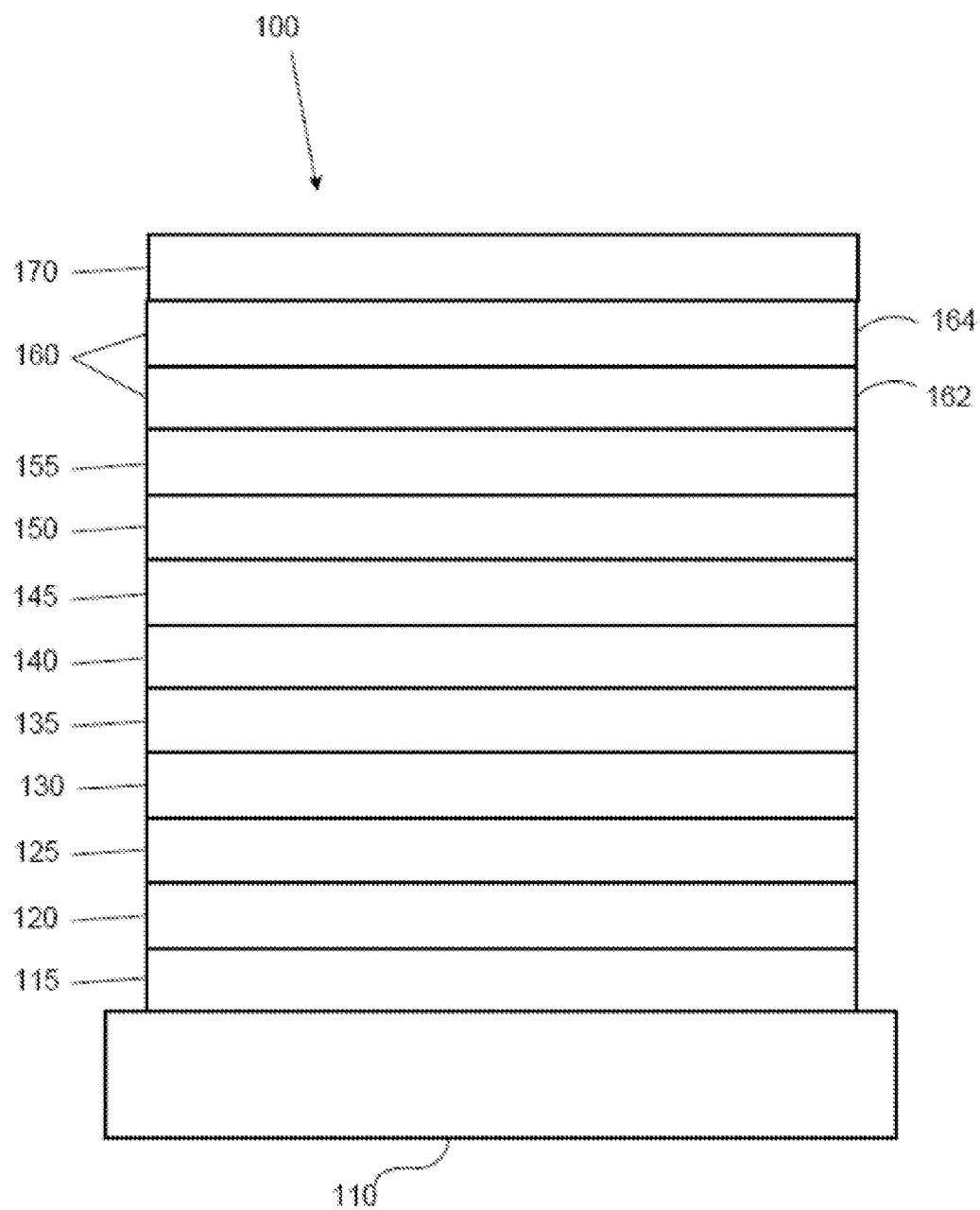
FIG. 1 shows an organic light emitting device.

FIG. 1 shows an organic light emitting. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
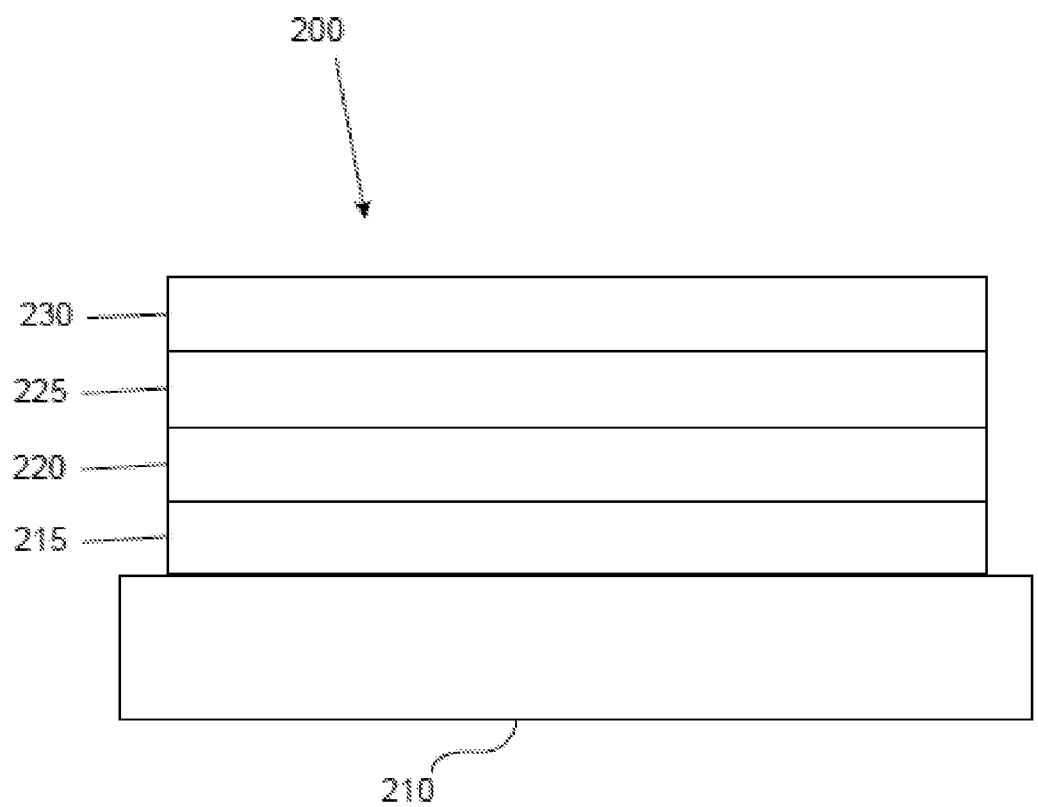
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halide," or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to an embodiment, a composition comprising a novel first compound is disclosed, wherein the first compound is capable of functioning as a phosphorescent emitter in an organic light emitting device at room temperature. The first compound has at least one aromatic ring and at least one substituent R, wherein each of the at least one substituent R is independently selected from the group consisting of partially fluorinated alkyl, partially fluorinated cycloalkyl, and combinations thereof; wherein each of the at least one substituent R is directly bonded to one of the aromatic rings, and wherein in each of the at least one substituent R, C having an F attached thereto is separated by at least one carbon atom from the aromatic ring.

Each of the at least one substituent R being directly bonded to one of the aromatic rings means that each R can be bonded to different aromatic rings or some of the Rs can be bonded to the same aromatic ring. Partially fluorinated group means that not all of the carbon-hydrogen bonds in a group have been replaced by carbon-fluorine bonds, in other words, there is at least one carbon-hydrogen bond remaining in that group.

In one embodiment, the first compound is capable of emitting light from a triplet excited state to a ground singlet state at room temperature.

In one embodiment, the first compound is a metal coordination complex having a metal-carbon bond. The metal can be selected from the group consisting of Ir, Rh, Re, Ru, Os, Pt, Au, and Cu. In one preferred embodiment, the metal is Ir. In another preferred embodiment, the metal is Pt.

In one embodiment of the first compound, C having an F attached thereto is separated by at least two carbon atoms from the aromatic ring. In another embodiment, C having an F attached thereto is separated by at least three carbon atoms from the aromatic ring.

In one embodiment of the first compound, each of the at least one substituent R contains at least one $CF_3$ group. In a preferred embodiment, each of the at least one substituent R contains only $CF_3$ group and no CF or $CF_2$ groups. In another embodiment, none of the at least one substituent R contain any $CF_3$ groups.

In one embodiment, the first compound does not have any F atoms other than those in the at least one substituent R.

In one embodiment of the first compound, the aromatic ring comprises LUMO electron density of the first compound.

In one embodiment of the first compound, m in the formula $C_nH_{2n+1-m}F_m$ and $C_qH_{2q-1-m}F_m$ is not a multiple of 3. In another embodiment, m is a multiple of 3.

According to an aspect of the present disclosure, the first compound as defined above has the formula of $M(L^1)_x(L^2)_y(L^3)_z$; wherein $L^1$, $L^2$, and $L^3$ can be the same or different;
  wherein x is 1, 2, or 3;
  wherein y is 0, 1, or 2;
  wherein z is 0, 1, or 2;
  wherein x+y+z is the oxidation state of the metal M;
  wherein $L^1$, $L^2$, and $L^3$ are each independently selected from the group consisting of:

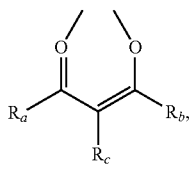
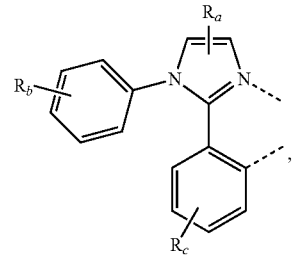
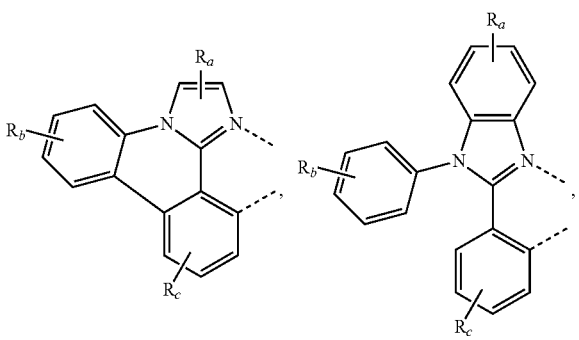
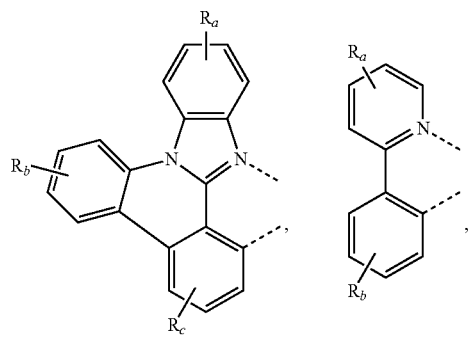
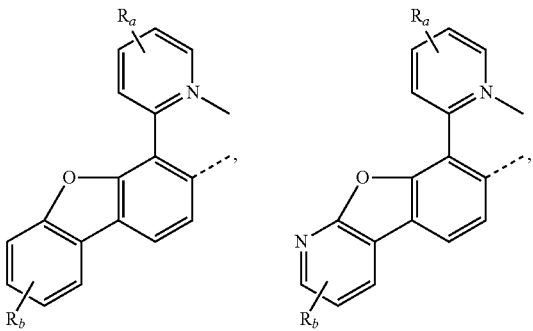
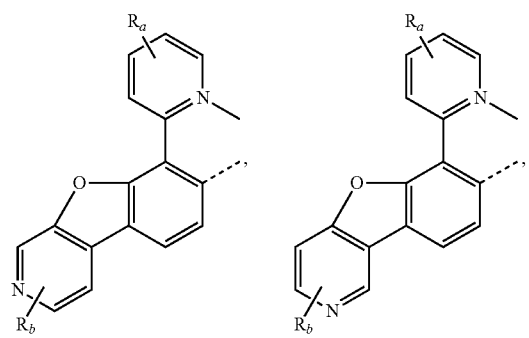

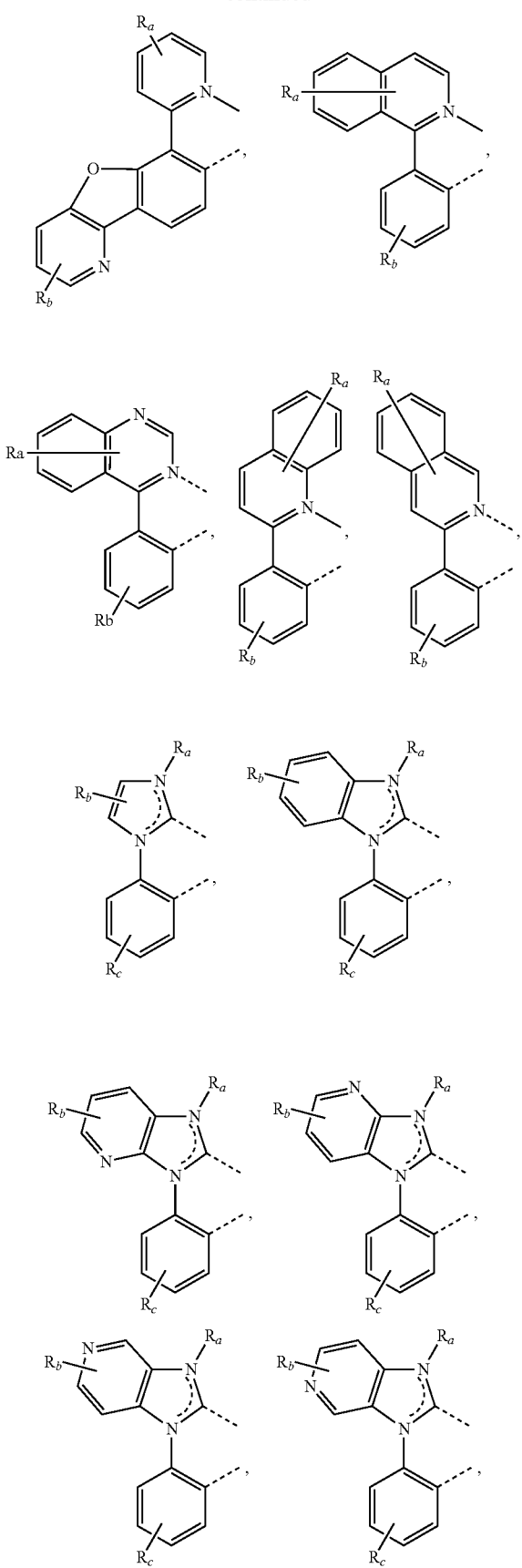

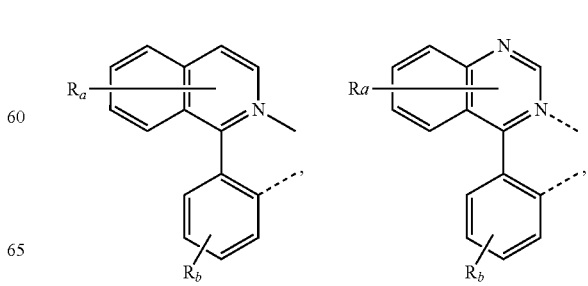

wherein $R_a$, $R_b$, $R_c$, and $R_d$ independently represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, $R_c$, and $R_d$ are optionally joined to form a ring or form a multidentate ligand; and wherein at least one of $R_a$, $R_b$, $R_c$, and $R_d$ includes at least one R.

In one embodiment of the first compound as defined above, M is Ir and the first compound has the formula of $Ir(L^1)_2(L^2)$. In the first compound having the formula of $Ir(L^1)_2(L^2)$, $L^1$ has the formula selected from the group consisting of:

-continued

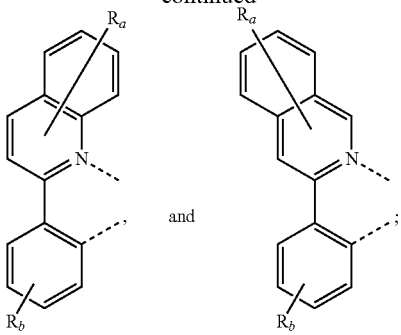

and
L² has the formula:

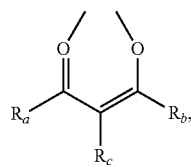

wherein $R_a$, $R_b$, and $R_c$ independently represent mono, di, tri, or tetra substitution, or no substitution;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, and $R_c$ are optionally joined to form a ring or form a multidentate ligand; and wherein at least one of $R_a$, $R_b$, and $R_c$ includes at least one R.

In another embodiment of the first compound as defined above, M is Ir and the first compound has the formula of $Ir(L^1)_2(L^2)$ where $L^1$ has the formula selected from the group consisting of:

L² has the formula:

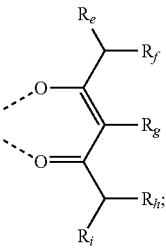

wherein $R_a$ and $R_b$ are as defined above and $R_e$, $R_f$, $R_h$, and $R_i$ are independently selected from group consisting of alkyl, cycloalkyl, aryl, and heteroaryl;

wherein at least one of $R_e$, $R_f$, $R_h$, and $R_i$ has at least two carbon atoms;

wherein $R_g$ is selected from group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of $R_a$ and $R_b$ includes at least one R.

In another embodiment of the first compound having the formula of $Ir(L^1)_2(L^2)$ as defined above, $L^1$ and $L^2$ are different and each are independently selected from the group consisting of:

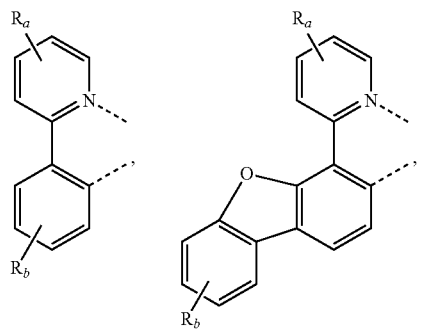

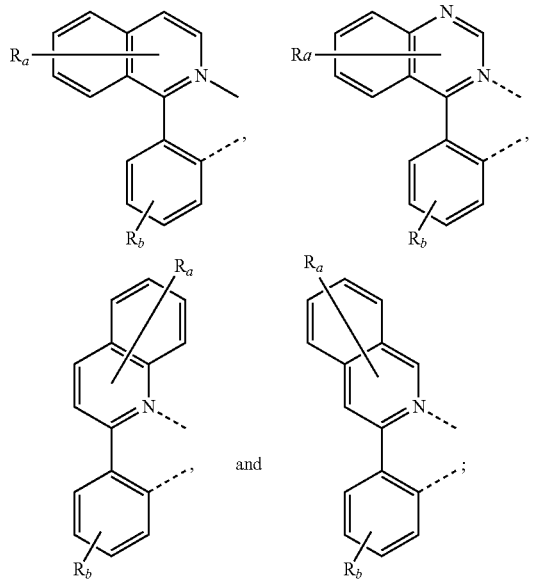

-continued

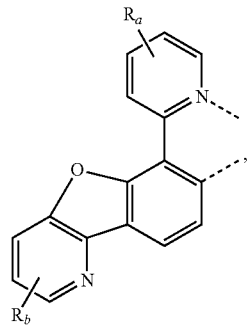

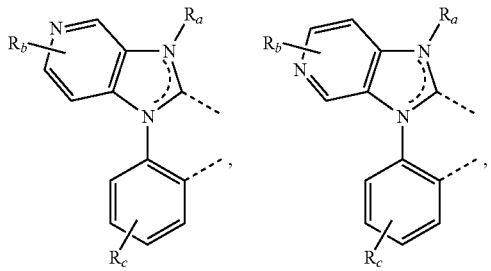

wherein at least one of $R_a$ and $R_b$ includes at least one R.

In another embodiment of the first compound having the formula of $Ir(L^1)_2(L^2)$, $L^1$ and $L^2$ are each independently selected from the group consisting of:

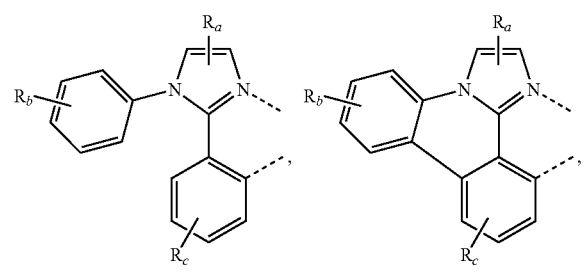

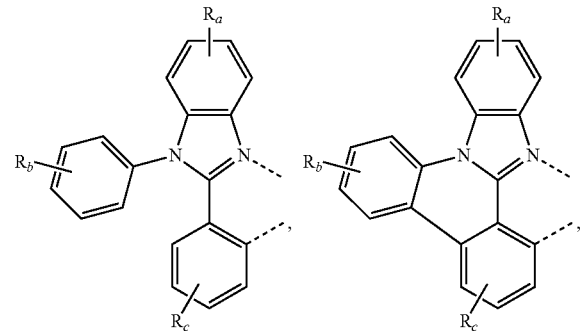

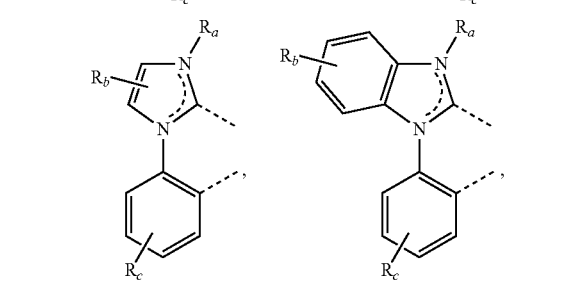

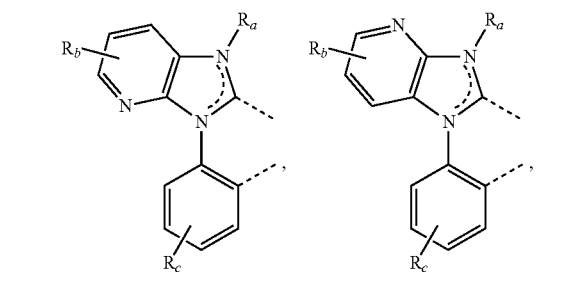

wherein at least one of $R_a$, $R_b$, and $R_c$ includes at least one R.

In the embodiment where the first compound has a structure according to the formula $M(L^1)_x(L^2)_y(L^3)_z$ defined above, the compound can have the formula of $Pt(L^1)_2$ or $Pt(L^1)(L^2)$. In the compound having the formula of $Pt(L^1)_2$, $L^1$ can be connected to the other $L^1$. In the compound having the formula $Pt(L^1)(L^2)$, $L^1$ can be connected to $L^2$ to form a tetradentate ligand. In one embodiment, at least one of $R_a$, $R_b$, $R_c$, and $R_d$ includes an alkyl or cycloalkyl group that includes CD, $CD_2$, or $CD_3$, wherein D is deuterium.

According to another aspect of the present disclosure, in the first compound having the formula of $M(L^1)_x(L^2)_y(L^3)_z$; $L^1$, $L^2$, and $L^3$ can be the same or different;

wherein x is 1, 2, or 3;

wherein y is 0, 1, or 2;

wherein z is 0, 1, or 2;

wherein x+y+z is the oxidation state of the metal M;

wherein $L^1$, $L^2$, and $L^3$ are each independently selected from the group consisting of $L_{A1}$ through $L_{A41}$, each represented by the formula

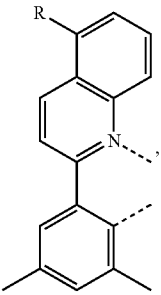

wherein
in $L_{A1}$, R = $R^{A1}$, in $L_{A2}$, R = $R^{A2}$,
in $L_{A3}$, R = $R^{A3}$, in $L_{A4}$, R = $R^{A4}$,
in $L_{A5}$, R = $R^{A5}$, in $L_{A6}$, R = $R^{A6}$,
in $L_{A7}$, R = $R^{A7}$, in $L_{A8}$, R = $R^{A8}$,
in $L_{A9}$, R = $R^{A9}$, in $L_{A10}$, R = $R^{A10}$,
in $L_{A11}$, R = $R^{A11}$, in $L_{A12}$, R = $R^{A12}$,
in $L_{A13}$, R = $R^{A13}$, in $L_{A14}$, R = $R^{A14}$,
in $L_{A15}$, R = $R^{A15}$, in $L_{A16}$, R = $R^{A16}$,
in $L_{A17}$, R = $R^{A17}$, in $L_{A18}$, R = $R^{A18}$,
in $L_{A19}$, R = $R^{A19}$, in $L_{A20}$, R = $R^{A20}$,
in $L_{A21}$, R = $R^{A21}$, in $L_{A22}$, R = $R^{A22}$,
in $L_{A23}$, R = $R^{A23}$, in $L_{A24}$, R = $R^{A24}$,
in $L_{A25}$, R = $R^{A25}$, in $L_{A26}$, R = $R^{A26}$,
in $L_{A27}$, R = $R^{A27}$, in $L_{A28}$, R = $R^{A28}$,
in $L_{A29}$, R = $R^{A29}$, in $L_{A30}$, R = $R^{A30}$,
in $L_{A31}$, R = $R^{A31}$, in $L_{A32}$, R = $R^{A32}$,
in $L_{A33}$, R = $R^{A33}$, in $L_{A34}$, R = $R^{A34}$,
in $L_{A35}$, R = $R^{A35}$, in $L_{A36}$, R = $R^{A36}$,
in $L_{A37}$, R = $R^{A37}$, in $L_{A38}$, R = $R^{A38}$,
in $L_{A39}$, R = $R^{A39}$, in $L_{A40}$, R = $R^{A40}$,
and in $L_{A41}$, R = $R^{A41}$;

$L_{A42}$ through $L_{A82}$, each represented by the formula

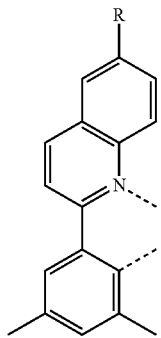

wherein
in $L_{A42}$, R = $R^{A1}$, in $L_{A43}$, R = $R^{A2}$,
in $L_{A44}$, R = $R^{A3}$, in $L_{A45}$, R = $R^{A4}$,
in $L_{A46}$, R = $R^{A5}$, in $L_{A47}$, R = $R^{A6}$,
in $L_{A48}$, R = $R^{A7}$, in $L_{A49}$, R = $R^{A8}$,
in $L_{A50}$, R = $R^{A9}$, in $L_{A51}$, R = $R^{A10}$,
in $L_{A52}$, R = $R^{A11}$, in $L_{A53}$, R = $R^{A12}$,
in $L_{A54}$, R = $R^{A13}$, in $L_{A55}$, R = $R^{A14}$,
in $L_{A56}$, R = $R^{A15}$, in $L_{A57}$, R = $R^{A16}$,
in $L_{A58}$, R = $R^{A17}$, in $L_{A59}$, R = $R^{A18}$,
in $L_{A60}$, R = $R^{A19}$, in $L_{A61}$, R = $R^{A20}$,
in $L_{A62}$, R = $R^{A21}$, in $L_{A63}$, R = $R^{A22}$,
in $L_{A64}$, R = $R^{A23}$, in $L_{A65}$, R = $R^{A24}$,
in $L_{A66}$, R = $R^{A25}$, in $L_{A67}$, R = $R^{A26}$,
in $L_{A68}$, R = $R^{A27}$, in $L_{A69}$, R = $R^{A28}$,
in $L_{A70}$, R = $R^{A29}$, in $L_{A71}$, R = $R^{A30}$,
in $L_{A72}$, R = $R^{A31}$, in $L_{A73}$, R = $R^{A32}$,
in $L_{A74}$, R = $R^{A33}$, in $L_{A75}$, R = $R^{A34}$,
in $L_{A76}$, R = $R^{A35}$, in $L_{A77}$, R = $R^{A36}$, in L$_{A78}$, R = R$^{A37}$, in L$_{A79}$, R = R$^{A38}$,
in L$_{A80}$, R = R$^{A39}$, in L$_{A81}$, R = R$^{A40}$,
and in L$_{A82}$, R = R$^{A41}$;;

L$_{A83}$ through L$_{A123}$, each represented by the formula

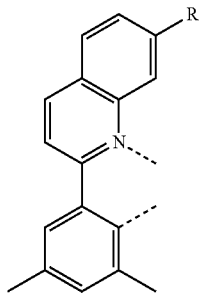

wherein
in L$_{A83}$, R = R$^{A1}$, in L$_{A84}$, R = R$^{A2}$,
in L$_{A85}$, R = R$^{A3}$, in L$_{A86}$, R = R$^{A4}$,
in L$_{A87}$, R = R$^{A5}$, in L$_{A88}$, R = R$^{A6}$,
in L$_{A89}$, R = R$^{A7}$, in L$_{A90}$, R = R$^{A8}$,
in L$_{A91}$, R = R$^{A9}$, in L$_{A92}$, R = R$^{A10}$,
in L$_{A93}$, R = R$^{A11}$, in L$_{A94}$, R = R$^{A12}$,
in L$_{A95}$, R = R$^{A13}$, in L$_{A96}$, R = R$^{A14}$,
in L$_{A97}$, R = R$^{A15}$, in L$_{A98}$, R = R$^{A16}$,
in L$_{A99}$, R = R$^{A17}$, in L$_{A100}$, R = R$^{A18}$,
in L$_{A101}$, R = R$^{A19}$, in L$_{A102}$, R = R$^{A20}$,
in L$_{A103}$, R = R$^{A21}$, in L$_{A104}$, R = R$^{A22}$,
in L$_{A105}$, R = R$^{A23}$, in L$_{A106}$, R = R$^{A24}$,
in L$_{A107}$, R = R$^{A25}$, in L$_{A108}$, R = R$^{A26}$,
in L$_{A109}$, R = R$^{A27}$, in L$_{A110}$, R = R$^{A28}$,
in L$_{A111}$, R = R$^{A29}$, in L$_{A112}$, R = R$^{A30}$,
in L$_{A113}$, R = R$^{A31}$, in L$_{A114}$, R = R$^{A32}$,
in L$_{A115}$, R = R$^{A33}$, in L$_{A116}$, R = R$^{A34}$,
in L$_{A117}$, R = R$^{A35}$, in L$_{A118}$, R = R$^{A36}$,
in L$_{A119}$, R = R$^{A37}$, in L$_{A120}$, R = R$^{A38}$,
in L$_{A121}$, R = R$^{A39}$, in L$_{A122}$, R = R$^{A40}$,
and in L$_{A123}$, R = R$^{A41}$;;

L$_{A124}$ through L$_{A164}$, each represented by the formula

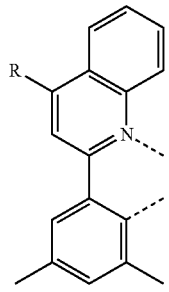

wherein
in L$_{A124}$, R = R$^{A1}$, in L$_{A125}$, R = R$^{A2}$,
in L$_{A126}$, R = R$^{A3}$, in L$_{A127}$, R = R$^{A4}$,
in L$_{A128}$, R = R$^{A5}$, in L$_{A129}$, R = R$^{A6}$,
in L$_{A130}$, R = R$^{A7}$, in L$_{A131}$, R = R$^{A8}$,
in L$_{A132}$, R = R$^{A9}$, in L$_{A133}$, R = R$^{A10}$,
in L$_{A134}$, R = R$^{A11}$, in L$_{A135}$, R = R$^{A12}$,
in L$_{A136}$, R = R$^{A13}$, in L$_{A137}$, R = R$^{A14}$,
in L$_{A138}$, R = R$^{A15}$, in L$_{A139}$, R = R$^{A16}$,
in L$_{A140}$, R = R$^{A17}$, in L$_{A141}$, R = R$^{A18}$,
in L$_{A142}$, R = R$^{A19}$, in L$_{A143}$, R = R$^{A20}$,
in L$_{A144}$, R = R$^{A21}$, in L$_{A145}$, R = R$^{A22}$,
in L$_{A146}$, R = R$^{A23}$, in L$_{A147}$, R = R$^{A24}$,
in L$_{A148}$, R = R$^{A25}$, in L$_{A149}$, R = R$^{A26}$,
in L$_{A150}$, R = R$^{A27}$, in L$_{A151}$, R = R$^{A28}$,
in L$_{A152}$, R = R$^{A29}$, in L$_{A153}$, R = R$^{A30}$,
in L$_{A154}$, R = R$^{A31}$, in L$_{A155}$, R = R$^{A32}$,
in L$_{A156}$, R = R$^{A33}$, in L$_{A157}$, R = R$^{A34}$,
in L$_{A158}$, R = R$^{A35}$, in L$_{A159}$, R = R$^{A36}$, in $L_{A160}$, R = $R^{437}$, in $L_{A161}$, R = $R^{438}$,
in $L_{A162}$, R = $R^{439}$, in $L_{A163}$, R = $R^{440}$,
and in $L_{A164}$, R = $R^{441}$,, $L_{A165}$ through $L_{A205}$, each
represented by the formula

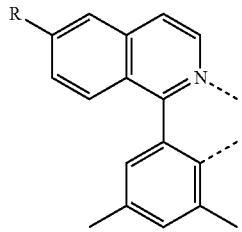

wherein
in $L_{A165}$, R = $R^{41}$, in $L_{A166}$, R = $R^{42}$,
in $L_{A167}$, R = $R^{43}$, in $L_{A168}$, R = $R^{44}$,
in $L_{A169}$, R = $R^{45}$, in $L_{A170}$, R = $R^{46}$,
in $L_{A171}$, R = $R^{47}$, in $L_{A172}$, R = $R^{48}$,
in $L_{A173}$, R = $R^{49}$, in $L_{A174}$, R = $R^{410}$,
in $L_{A175}$, R = $R^{411}$, in $L_{A176}$, R = $R^{412}$,
in $L_{A177}$, R = $R^{413}$, in $L_{A178}$, R = $R^{414}$,
in $L_{A179}$, R = $R^{415}$, in $L_{A180}$, R = $R^{416}$,
in $L_{A181}$, R = $R^{417}$, in $L_{A182}$, R = $R^{418}$,
in $L_{A183}$, R = $R^{419}$, in $L_{A184}$, R = $R^{420}$,
in $L_{A185}$, R = $R^{421}$, in $L_{A186}$, R = $R^{422}$,
in $L_{A187}$, R = $R^{423}$, in $L_{A188}$, R = $R^{424}$,
in $L_{A189}$, R = $R^{425}$, in $L_{A190}$, R = $R^{426}$,
in $L_{A191}$, R = $R^{427}$, in $L_{A192}$, R = $R^{428}$,
in $L_{A193}$, R = $R^{429}$, in $L_{A194}$, R = $R^{430}$,
in $L_{A195}$, R = $R^{431}$, in $L_{A196}$, R = $R^{432}$,
in $L_{A197}$, R = $R^{433}$, in $L_{A198}$, R = $R^{434}$,
in $L_{A199}$, R = $R^{435}$, in $L_{A200}$, R = $R^{436}$,
in $L_{A201}$, R = $R^{437}$, in $L_{A202}$, R = $R^{438}$,
in $L_{A203}$, R = $R^{439}$, in $L_{A204}$, R = $R^{440}$,
and in $L_{A205}$, R = $R^{441}$;, $L_{A206}$ through $L_{A246}$, each
represented by the formula

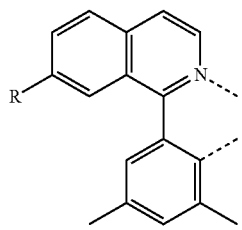

wherein
in $L_{A206}$, R = $R^{41}$, in $L_{A207}$, R = $R^{42}$,
in $L_{A208}$, R = $R^{43}$, in $L_{A209}$, R = $R^{44}$,
in $L_{A210}$, R = $R^{45}$, in $L_{A211}$, R = $R^{46}$,
in $L_{A212}$, R = $R^{47}$, in $L_{A213}$, R = $R^{48}$,
in $L_{A214}$, R = $R^{49}$, in $L_{A215}$, R = $R^{410}$,
in $L_{A216}$, R = $R^{411}$, in $L_{A217}$, R = $R^{412}$,
in $L_{A218}$, R = $R^{413}$, in $L_{A219}$, R = $R^{414}$,
in $L_{A220}$, R = $R^{415}$, in $L_{A221}$, R = $R^{416}$,
in $L_{A222}$, R = $R^{417}$, in $L_{A223}$, R = $R^{418}$,
in $L_{A224}$, R = $R^{419}$, in $L_{A225}$, R = $R^{420}$,
in $L_{A226}$, R = $R^{421}$, in $L_{A227}$, R = $R^{422}$,
in $L_{A228}$, R = $R^{423}$, in $L_{A229}$, R = $R^{424}$,
in $L_{A230}$, R = $R^{425}$, in $L_{A231}$, R = $R^{426}$,
in $L_{A232}$, R = $R^{427}$, in $L_{A233}$, R = $R^{428}$,
in $L_{A234}$, R = $R^{429}$, in $L_{A235}$, R = $R^{430}$,
in $L_{A236}$, R = $R^{431}$, in $L_{A237}$, R = $R^{432}$,
in $L_{A238}$, R = $R^{433}$, in $L_{A239}$, R = $R^{434}$,
in $L_{A240}$, R = $R^{435}$, in $L_{A241}$, R = $R^{436}$, -continued in $L_{A242}$, R = $R^{437}$, in $L_{A243}$, R = $R^{438}$,
in $L_{A244}$, R = $R^{439}$, in $L_{A245}$, R = $R^{440}$,
and in $L_{A246}$, R = $R^{A41}$;

$L_{A247}$ through $L_{A287}$, each
represented by the formula

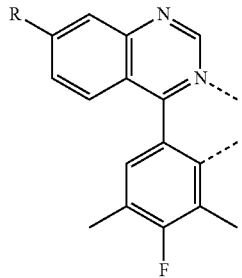

wherein
in $L_{A247}$, R = $R^{41}$, in $L_{A248}$, R = $R^{42}$,
in $L_{A249}$, R = $R^{43}$, in $L_{A250}$, R = $R^{44}$,
in $L_{A251}$, R = $R^{45}$, in $L_{A252}$, R = $R^{46}$,
in $L_{A253}$, R = $R^{47}$, in $L_{A254}$, R = $R^{48}$,
in $L_{A255}$, R = $R^{49}$, in $L_{A256}$, R = $R^{410}$,
in $L_{A257}$, R = $R^{411}$, in $L_{A258}$, R = $R^{412}$,
in $L_{A259}$, R = $R^{413}$, in $L_{A260}$, R = $R^{414}$,
in $L_{A261}$, R = $R^{415}$, in $L_{A262}$, R = $R^{416}$,
in $L_{A263}$, R = $R^{417}$, in $L_{A264}$, R = $R^{418}$,
in $L_{A265}$, R = $R^{419}$, in $L_{A266}$, R = $R^{420}$,
in $L_{A267}$, R = $R^{421}$, in $L_{A268}$, R = $R^{422}$,
in $L_{A269}$, R = $R^{423}$, in $L_{A270}$, R = $R^{424}$,
in $L_{A271}$, R = $R^{425}$, in $L_{A272}$, R = $R^{426}$,
in $L_{A273}$, R = $R^{427}$, in $L_{A274}$, R = $R^{428}$,
in $L_{A275}$, R = $R^{429}$, in $L_{A276}$, R = $R^{430}$,
in $L_{A277}$, R = $R^{431}$, in $L_{A278}$, R = $R^{432}$,
in $L_{A279}$, R = $R^{433}$, in $L_{A280}$, R = $R^{434}$,
in $L_{A281}$, R = $R^{435}$, in $L_{A282}$, R = $R^{436}$,
in $L_{A283}$, R = $R^{437}$, in $L_{A284}$, R = $R^{438}$,
in $L_{A285}$, R = $R^{439}$, in $L_{A286}$, R = $R^{440}$,
and in $L_{A287}$, R = $R^{A41}$;

$L_{A288}$ through $L_{A328}$, each
represented by the formula

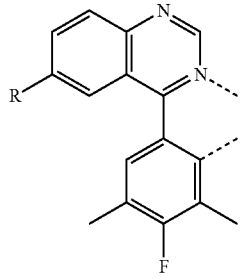

wherein
in $L_{A288}$, R = $R^{41}$, in $L_{A289}$, R = $R^{42}$,
in $L_{A290}$, R = $R^{43}$, in $L_{A291}$, R = $R^{44}$,
in $L_{A292}$, R = $R^{45}$, in $L_{A293}$, R = $R^{46}$,
in $L_{A294}$, R = $R^{47}$, in $L_{A295}$, R = $R^{48}$,
in $L_{A296}$, R = $R^{49}$, in $L_{A297}$, R = $R^{410}$,
in $L_{A298}$, R = $R^{411}$, in $L_{A299}$, R = $R^{412}$,
in $L_{A300}$, R = $R^{413}$, in $L_{A301}$, R = $R^{414}$,
in $L_{A302}$, R = $R^{415}$, in $L_{A303}$, R = $R^{416}$,
in $L_{A304}$, R = $R^{417}$, in $L_{A305}$, R = $R^{418}$,
in $L_{A306}$, R = $R^{419}$, in $L_{A307}$, R = $R^{420}$,
in $L_{A308}$, R = $R^{421}$, in $L_{A309}$, R = $R^{422}$,
in $L_{A310}$, R = $R^{423}$, in $L_{A311}$, R = $R^{424}$,
in $L_{A312}$, R = $R^{425}$, in $L_{A313}$, R = $R^{426}$,
in $L_{A314}$, R = $R^{427}$, in $L_{A315}$, R = $R^{428}$,
in $L_{A316}$, R = $R^{429}$, in $L_{A317}$, R = $R^{430}$,
in $L_{A318}$, R = $R^{431}$, in $L_{A319}$, R = $R^{432}$,
in $L_{A320}$, R = $R^{433}$, in $L_{A321}$, R = $R^{434}$, -continued in $L_{A322}$, R = $R^{A35}$, in $L_{A323}$, R = $R^{A36}$,
in $L_{A324}$, R = $R^{A37}$, in $L_{A325}$, R = $R^{A38}$,
in $L_{A326}$, R = $R^{A39}$, in $L_{A327}$, R = $R^{A40}$,
and in $L_{A328}$, R = $R^{A41}$;

$L_{A329}$ through $L_{A369}$, each represented by the formula

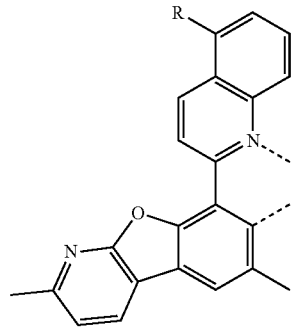

wherein
in $L_{A329}$, R = $R^{A1}$, in $L_{A330}$, R = $R^{A2}$,
in $L_{A331}$, R = $R^{A3}$, in $L_{A332}$, R = $R^{A4}$,
in $L_{A333}$, R = $R^{A5}$, in $L_{A334}$, R = $R^{A6}$,
in $L_{A335}$, R = $R^{A7}$, in $L_{A336}$, R = $R^{A8}$,
in $L_{A337}$, R = $R^{A9}$, in $L_{A338}$, R = $R^{A10}$,
in $L_{A339}$, R = $R^{A11}$, in $L_{A340}$, R = $R^{A12}$,
in $L_{A341}$, R = $R^{A13}$, in $L_{A342}$, R = $R^{A14}$,
in $L_{A343}$, R = $R^{A15}$, in $L_{A344}$, R = $R^{A16}$,
in $L_{A345}$, R = $R^{A17}$, in $L_{A346}$, R = $R^{A18}$,
in $L_{A347}$, R = $R^{A19}$, in $L_{A348}$, R = $R^{A20}$,
in $L_{A349}$, R = $R^{A21}$, in $L_{A350}$, R = $R^{A22}$,
in $L_{A351}$, R = $R^{A23}$, in $L_{A352}$, R = $R^{A24}$,
in $L_{A353}$, R = $R^{A25}$, in $L_{A354}$, R = $R^{A26}$,
in $L_{A355}$, R = $R^{A27}$, in $L_{A356}$, R = $R^{A28}$,
in $L_{A357}$, R = $R^{A29}$, in $L_{A358}$, R = $R^{A30}$,
in $L_{A359}$, R = $R^{A31}$, in $L_{A360}$, R = $R^{A32}$,
in $L_{A361}$, R = $R^{A33}$, in $L_{A362}$, R = $R^{A34}$,
in $L_{A363}$, R = $R^{A35}$, in $L_{A364}$, R = $R^{A36}$,
in $L_{A365}$, R = $R^{A37}$, in $L_{A366}$, R = $R^{A38}$,
in $L_{A367}$, R = $R^{A39}$, in $L_{A368}$, R = $R^{A40}$,
and in $L_{A369}$, R = $R^{A41}$;

$L_{A370}$ through $L_{A410}$, each represented by the formula

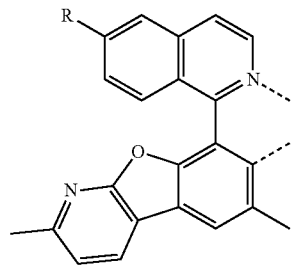

wherein
in $L_{A370}$, R = $R^{A1}$, in $L_{A371}$, R = $R^{A2}$,
in $L_{A372}$, R = $R^{A3}$, in $L_{A373}$, R = $R^{A4}$,
in $L_{A374}$, R = $R^{A5}$, in $L_{A375}$, R = $R^{A6}$,
in $L_{A376}$, R = $R^{A7}$, in $L_{A377}$, R = $R^{A8}$,
in $L_{A378}$, R = $R^{A9}$, in $L_{A379}$, R = $R^{A10}$,
in $L_{A380}$, R = $R^{A11}$, in $L_{A381}$, R = $R^{A12}$,
in $L_{A382}$, R = $R^{A13}$, in $L_{A383}$, R = $R^{A14}$,
in $L_{A384}$, R = $R^{A15}$, in $L_{A385}$, R = $R^{A16}$,
in $L_{A386}$, R = $R^{A17}$, in $L_{A387}$, R = $R^{A18}$,
in $L_{A388}$, R = $R^{A19}$, in $L_{A389}$, R = $R^{A20}$,
in $L_{A390}$, R = $R^{A21}$, in $L_{A391}$, R = $R^{A22}$,
in $L_{A392}$, R = $R^{A23}$, in $L_{A393}$, R = $R^{A24}$,
in $L_{A394}$, R = $R^{A25}$, in $L_{A395}$, R = $R^{A26}$,
in $L_{A396}$, R = $R^{A27}$, in $L_{A397}$, R = $R^{A28}$,
in $L_{A398}$, R = $R^{A29}$, in $L_{A399}$, R = $R^{A30}$,
in $L_{A400}$, R = $R^{A31}$, in $L_{A401}$, R = $R^{A32}$,
in $L_{A402}$, R = $R^{A33}$, in $L_{A403}$, R = $R^{A34}$, in $L_{A404}$, R = $R^{A35}$, in $L_{A405}$, R = $R^{A36}$, in $L_{A406}$, R = $R^{A37}$, in $L_{A407}$, R = $R^{A38}$, in $L_{A408}$, R = $R^{A39}$, in $L_{A409}$, R = $R^{A40}$, and in $L_{A410}$, R = $R^{A41}$;, and $L_{A411}$ through $L_{A451}$, each represented by the formula

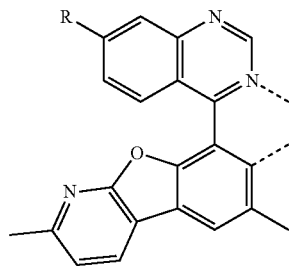

wherein
in $L_{A411}$, R = $R^{A1}$, in $L_{A412}$, R = $R^{A2}$,
in $L_{A413}$, R = $R^{A3}$, in $L_{A414}$, R = $R^{A4}$,
in $L_{A415}$, R = $R^{A5}$, in $L_{A416}$, R = $R^{A6}$,
in $L_{A417}$, R = $R^{A7}$, in $L_{A418}$, R = $R^{A8}$,
in $L_{A419}$, R = $R^{A9}$, in $L_{A420}$, R = $R^{A10}$,
in $L_{A421}$, R = $R^{A11}$, in $L_{A422}$, R = $R^{A12}$,
in $L_{A423}$, R = $R^{A13}$, in $L_{A424}$, R = $R^{A14}$,
in $L_{A425}$, R = $R^{A15}$, in $L_{A426}$, R = $R^{A16}$,
in $L_{A427}$, R = $R^{A17}$, in $L_{A428}$, R = $R^{A18}$,
in $L_{A429}$, R = $R^{A19}$, in $L_{A430}$, R = $R^{A20}$,
in $L_{A431}$, R = $R^{A21}$, in $L_{A432}$, R = $R^{A22}$,
in $L_{A433}$, R = $R^{A23}$, in $L_{A434}$, R = $R^{A24}$,
in $L_{A435}$, R = $R^{A25}$, in $L_{A436}$, R = $R^{A26}$,
in $L_{A437}$, R = $R^{A27}$, in $L_{A438}$, R = $R^{A28}$,
in $L_{A439}$, R = $R^{A29}$, in $L_{A440}$, R = $R^{A30}$,
in $L_{A441}$, R = $R^{A31}$, in $L_{A442}$, R = $R^{A32}$,
in $L_{A443}$, R = $R^{A33}$, in $L_{A444}$, R = $R^{A34}$,
in $L_{A445}$, R = $R^{A35}$, in $L_{A446}$, R = $R^{A36}$,
in $L_{A447}$, R = $R^{A37}$, in $L_{A448}$, R = $R^{A38}$,
in $L_{A449}$, R = $R^{A39}$, in $L_{A450}$, R = $R^{A40}$,
and in $L_{A451}$, R = $R^{A41}$;;

wherein, $R^{A1}$ through $R^{A41}$ have the formulas:

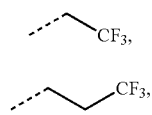 $R^{A1}$

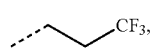 $R^{A2}$

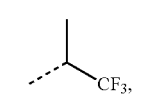 $R^{A3}$

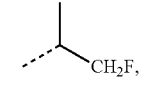 $R^{A4}$

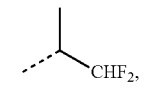 $R^{A5}$

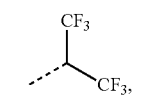 $R^{A6}$

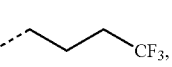 $R^{A7}$

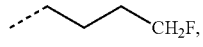 $R^{A8}$

 $R^{A9}$

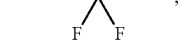 $R^{A10}$

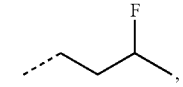 $R^{A11}$

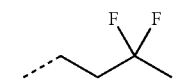 $R^{A12}$

 $R^{A13}$

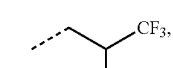 $R^{A14}$

-continued
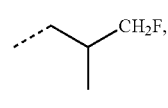 R^{A415}
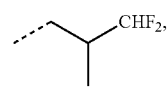 R^{A416}
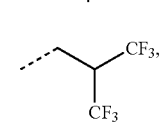 R^{A417}
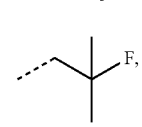 R^{A418}
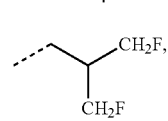 R^{A419}
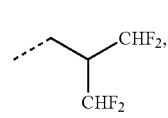 R^{A420}
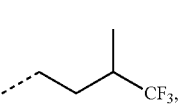 R^{A421}
 R^{A422}
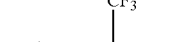 R^{A423}
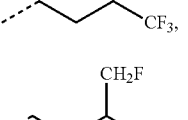 R^{A424}
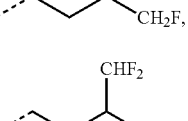 R^{A425}
 R^{A426}
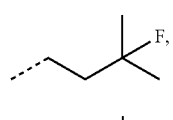 R^{A427}
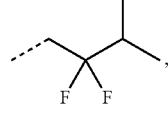 R^{A428}
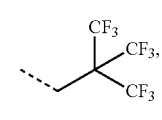 R^{A429}
-continued
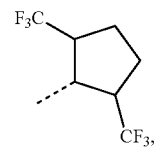 R^{A430}
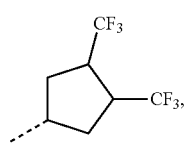 R^{A431}
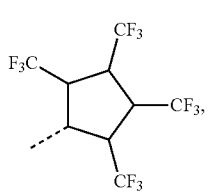 R^{A432}
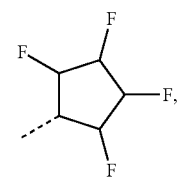 R^{A433}
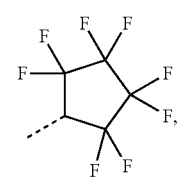 R^{A434}
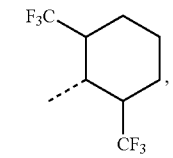 R^{A435}
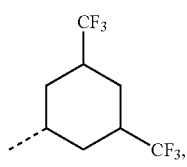 R^{A436}
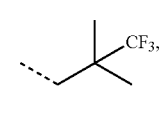
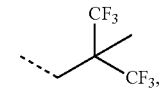
R^{A437}

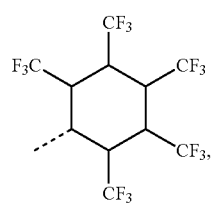 $R^{A38}$
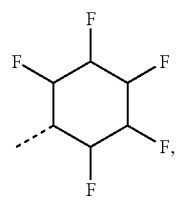 $R^{A39}$
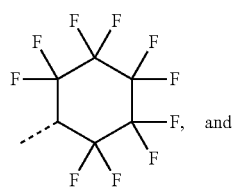 $R^{A40}$, and
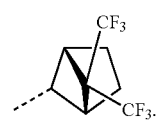 $R^{A41}$.
In one embodiment, where the first compound has a structure according to the formula of $Ir(L^1)_2(L^2)$, $L^1$ is selected from the group consisting of $L_{A1}$ through $L_{A450}$, and $L_{A451}$, and $L^2$ is selected from the group consisting of
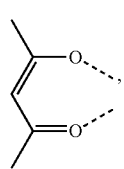 $L_{B1}$
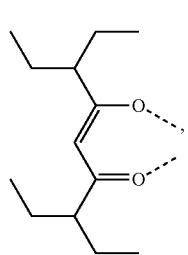 $L_{B2}$
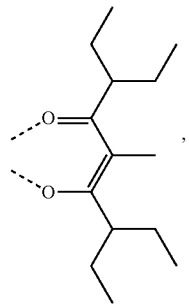 $L_{B3}$
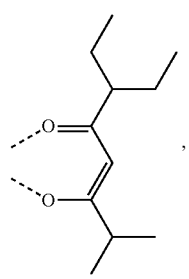 $L_{B4}$
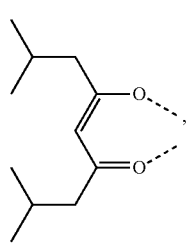 $L_{B5}$
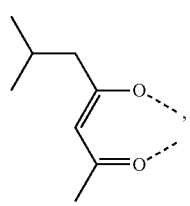 $L_{B6}$
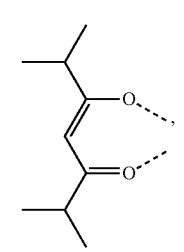 $L_{B7}$
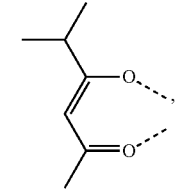 $L_{B8}$ $L_{B9}$ 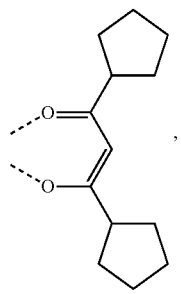

$L_{B10}$ 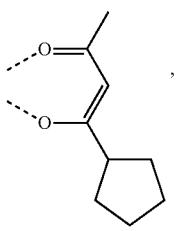

$L_{B11}$ 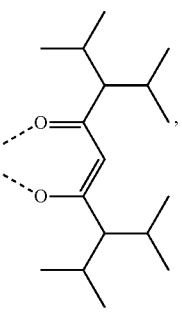

$L_{B12}$ 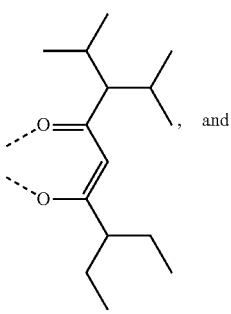, and $L_{B13}$ 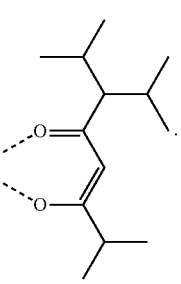.

In the above structures, the dash line represents the bond between the current group and the next group to which it attaches. For example, in $L_{A1}$, dash lines represent the bonds between the M and the ligand; in $R^{A1}$, dash line represents the bond between R and the aromatic ring.

In another embodiment, the first compound is selected from the group consisting of Compound 1 through Compound 5,863, wherein each of Compound x, where x=451j+k−451, k is an integer from 1 to 451, and j is an integer from 1 to 13, has the formula $Ir(L_{Ak})_2(L_{Bj})$. $L_{A1}$ through $L_{A451}$ and $L_{B1}$ through $L_{B13}$ are as defined above.

The examples of the first compound disclosed herein are metal complexes based on ligands containing 1-phenylisoquinoline, 2-phenylquinoline, 8-(quinolin-2-yl)benzofuro[2,3-b]pyridine, 8-(isoquinolin-1-yl)benzofuro[2,3-b]pyridine, 4-(4-fluorophenyl)quinazoline, or 2-phenylpyridine, etc. Each of the ligands contain at least one alkylated side chain which contains at least one fluorine atom that is not benzylic. The presence of these side chains provide a fine tuning of the color of the metal complex mostly as a slight red shift. The shorter the spacer in between the aromatic unit and the fluorine atom, the greater the red shift in the final complex will be. Good efficiencies were observed from these compounds. More importantly, it was unexpectedly discovered that the inventive compounds showed much better lifetime than compounds with fluorine at the benzylic position. Previous compounds with trifluoromethyl substitution and perfluoro alkyl substitution have shown very poor device stability.

According to another aspect, a first device comprising a first organic light emitting device is disclosed. The first organic light emitting device comprises: an anode; a cathode; and an organic layer, disposed between the anode and the cathode. The organic layer comprises the first compound as disclosed herein. The first compound incorporated into the first device can be any one or more of the embodiments and variations of the first compound disclosed herein. For example, the first compound is capable of functioning as a phosphorescent emitter at room temperature and wherein the first compound has at least one aromatic ring and at least one substituent R, wherein each of the at least one substituent R is independently selected from the group consisting of partially fluorinated alkyl, partially fluorinated cycloalkyl, and combinations thereof; wherein each of the at least one substituent R is directly bonded to one of the aromatic rings; and wherein in each of the at least one substituent R, C having an F attached thereto is separated by at least one carbon atom from the aromatic ring.

According to an embodiment, the first device is selected from the group consisting of a consumer product, an electronic component module, an organic light emitting device, and a lighting panel.

In the first device, the organic layer is an emissive layer and the compound is an emissive dopant.

In one embodiment of the first device, the organic layer further comprises a host; wherein the host comprises a triphenylene containing benzo-fused thiophene or benzo-fused furan; wherein any substituent in the host material is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C—

$C_nH_{2n+1}$, $Ar_1$, $Ar_1$-$Ar_2$, $C_nH_{2n}$—$Ar_1$, or no substitution; wherein n is from 1 to 10; and wherein $Ar_1$ and $Ar_2$ are independently selected from the group consisting of benzene, biphenyl, naphthalene, triphenylene, carbazole, and heteroaromatic analogs thereof.

The host in the first device can comprise at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

The host can be selected from the group consisting of:

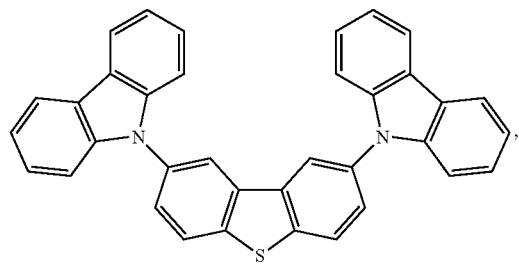

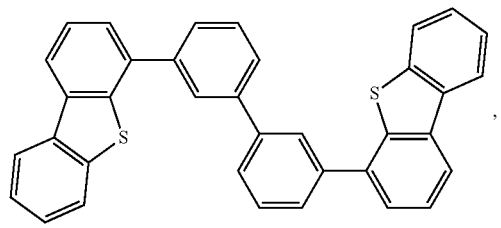

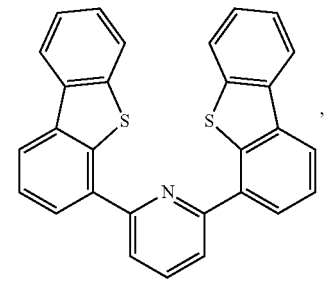

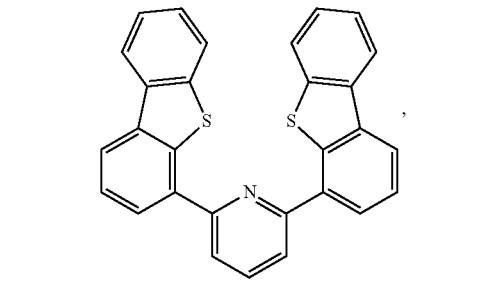

-continued

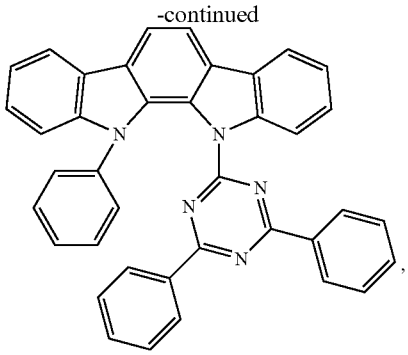

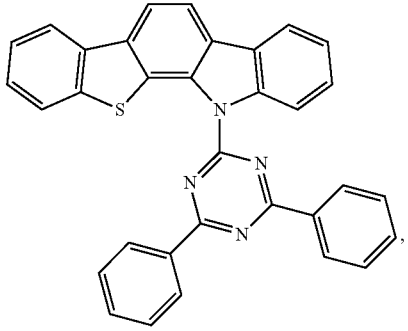

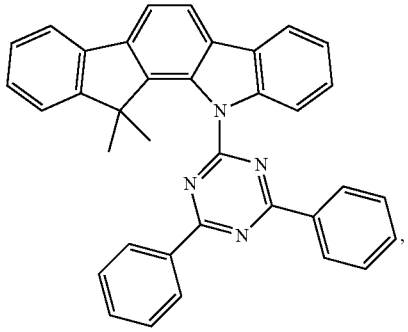

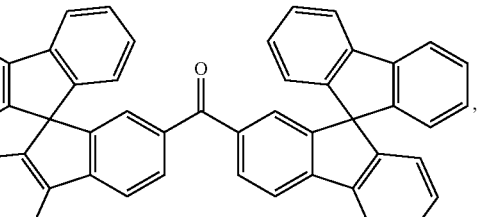

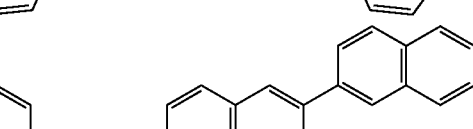

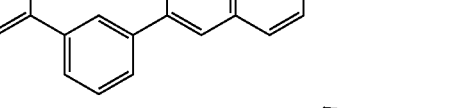

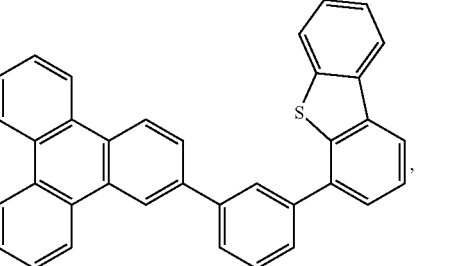

-continued

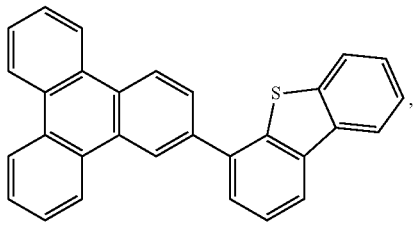

and combinations thereof.

The first device of claim 25, wherein the host material comprises a metal complex.

In yet another aspect of the present disclosure, a formulation that comprises the compound having at least one non-conjugated substituent R selected from the group consisting of $C_nH_{2n+1-m}F_m$ and $C_qH_{2q-1-m}F_m$, wherein R is directly bonded to an aromatic ring. n is an integer greater than 1, q is an integer greater than 2, and m is an integer greater than 0, wherein C having F attaching to is separated by at least one carbon atom from the aromatic ring is disclosed. The formulation can also include one or more components selected from the group consisting of a solvent, a host, a hole injection material, hole transport material, and an electron transport layer material, disclosed herein.

MATERIALS SYNTHESIS

All reactions were carried out under nitrogen protections unless specified otherwise. All solvents for reactions are anhydrous and used as received from commercial sources.

Synthesis Of Comparative Compound 1

Synthesis of (2-amino-6-(trifluoromethyl)phenyl)methanol

2-amino-6-(trifluoromethyl)benzoic acid (20 g, 97 mmol) was dissolved in tetrahydrofuran (120 mL) in a 3-neck RB flask equipped with an addition funnel and a condenser. The solution was cooled in an ice-water bath. LiAlH$_4$ (83 mL, 166 mmol) (2M solution in THF) was then added dropwise. After all of the LiAlH$_4$ solution was added, the reaction mixture was allowed to warm to room temperature and stirred at room temperature overnight. The reaction was then quenched by adding 10 mL of Water, then 10 mL of 15% NaOH and then 25 mL of Water. The salts were filtered off and the solvents were evaporated under vacuum. The product was used as is (18 g, 97% yield).

Synthesis of 2-(3,5-dimethylphenyl)-5-(trifluoromethyl)quinoline

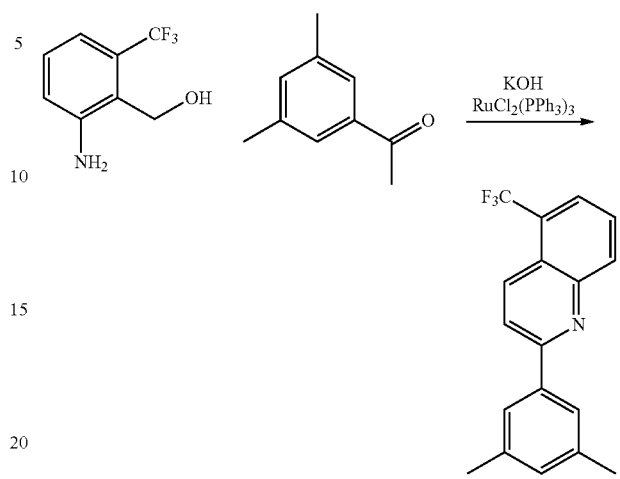

A mixture of (2-amino-6-(trifluoromethyl)phenyl)methanol (18 g, 94 mmol), 1-(3,5-dimethylphenyl)ethanone (19.5 ml, 130 mmol), powdered potassium hydroxide (0.90 g, 16.0 mmol), and RuCl$_2$(PPh$_3$)$_3$ (0.45 g, 0.47 mmol) in toluene (310 ml) was refluxed overnight. Upon cooling to room temperature, the mixture was washed with water and extracted with ethyl acetate (3 times). The crude material was coated on celite and purified by CC starting with 5% EA in Heptanes. The product obtained was recrystallized from methanol to afford 2-(3,5-dimethylphenyl)-5-(trifluoromethyl)quinoline (10 g, 35% yield) as yellow crystals.

Synthesis of Ir(III) Dimer

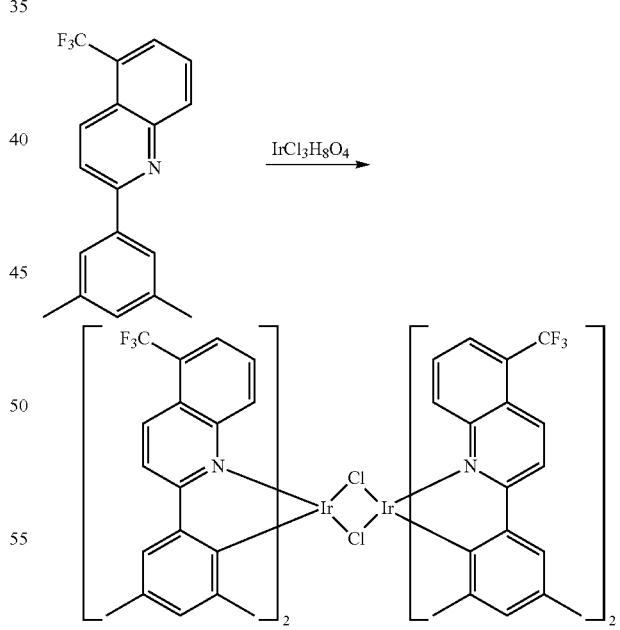

2-(3,5-dimethylphenyl)-5-(trifluoromethyl)quinoline (3.00 g, 9.96 mmol) was solubilized in ethoxyethanol (30 mL) and water (10 mL) and degassed with nitrogen for 30 minutes. Iridium chloride (0.92 g, 2.49 mmol) was then added to the solution and the reaction was refluxed under nitrogen for 24 hours. After cooling down to room temperature, the solid was filtered, washed with methanol and dried to give Ir(III) Dimer (1.0 g, 49% yield) as a brown powder.

Synthesis of Comparative Compound 1

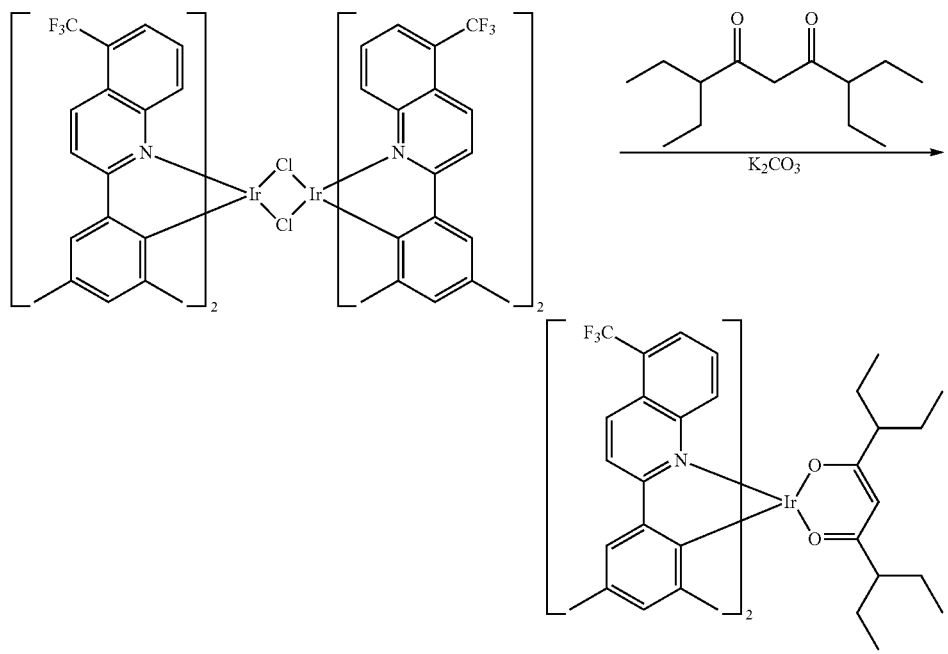

The Ir(III) Dimer (1.08 g, 0.65 mmol) and 3,7-diethyl-nonane-4,6-dione (1.38 g, 6.52 mmol) were diluted in ethoxyethanol (22 mL) and the mixture was degassed by bubbling nitrogen gas for 15 minutes. $K_2CO_3$ (0.90 g, 6.52 mmol) was then added and the reaction was stirred at room temperature overnight. The mixture was diluted with dichloromethane ("DCM"), filtered through a pad of Celite, and washed with DCM. The crude material was purified by column chromatography (silica pre-treated with triethylamine (TEA)) using Heptanes/DCM 80/20 solvent system. The collected pure fractions were triturated from methanol and the solids were recrystallized from dichloromethane/methanol to afford the Comparative Compound 1 (0.85 g, 65% yield) as a dark red powder.

Synthesis of Compound 453

Synthesis of 2-(3,5-dimethylphenyl)-5-(3,3,3-trifluoropropyl)quinoline

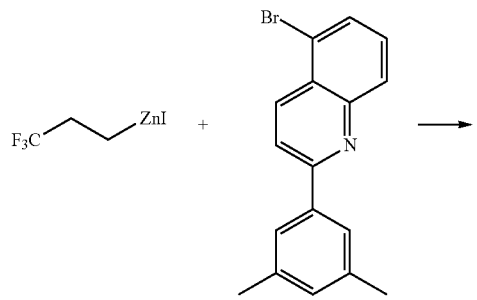

-continued

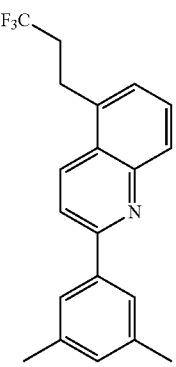

5-bromo-2-(3,5-dimethylphenyl)quinoline (1.15 g, 3.68 mmol), Palladium(II) acetate (0.017 g, 0.074 mmol), and CPhos (0.064 g, 0.147 mmol) were charged into a flask and diluted with 100 mL of tetrahydrofuran. This mixture was degassed with nitrogen followed by the addition of (3,3,3-trifluoropropyl)zinc(II) iodide (1.07 g, 3.68 mmol) via syringe. The reaction mixture was stirred at room temperature overnight. The reaction mixture was quenched with aqueous ammonium chloride then was extracted 2×200 mL of ethyl acetate, and dried over sodium sulfate. The crude material was coated on Celite and purified by column chromatography using a 20% DCM in Heptanes solvent system. The product was recrystallized in heptanes to afford 0.90 g of the target compound (81% yield).

Synthesis of Ir(III) Dimer

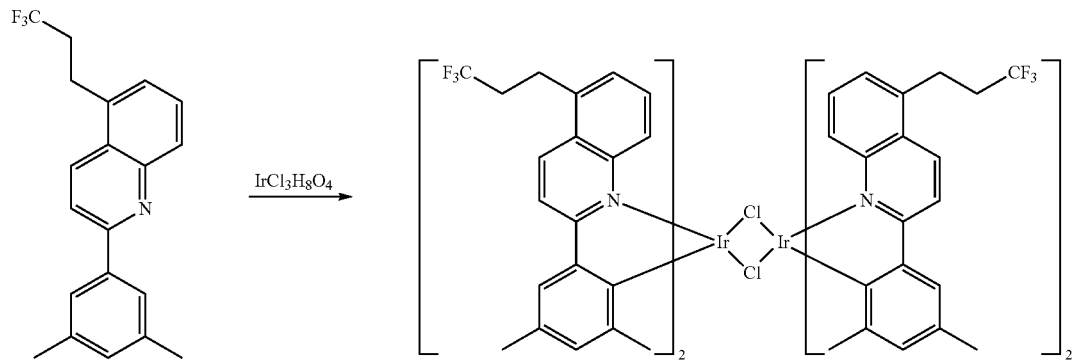

2-(3,5-dimethylphenyl)-5-(3,3,3-trifluoropropyl)quinoline (1.80 g, 5.47 mmol) was solubilized in ethoxyethanol (15 mL) and Water (5 mL) and degassed with nitrogen for 30 minutes. Iridium Chloride (0.54 g, 1.46 mmol) was then added to the solution and the reaction was refluxed under nitrogen for 24 hours. After cooling down to room temperature, the solid was filtered, washed with methanol and dried to give Ir(III) Dimer (0.95 g, 74% yield) as a brown powder.

Synthesis of Compound 453

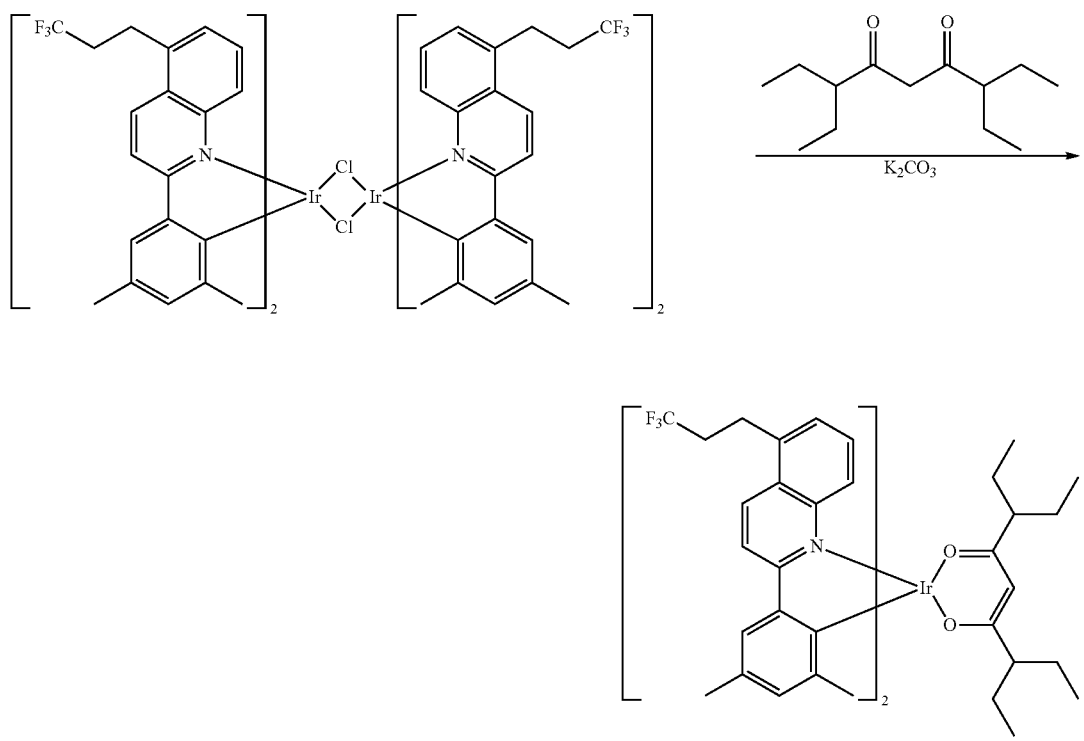

The Ir(III) Dimer (0.95 g, 0.537 mmol) and 3,7-diethylnonane-4,6-dione (1.14 g, 5.37 mmol) were diluted in ethoxyethanol (15 mL) and the mixture was degassed by bubbling nitrogen gas for 15 minutes. K$_2$CO$_3$ (0.74 g, 5.37 mmol) was then added and the reaction was stirred at room temperature overnight. The mixture was diluted with DCM, filtered through a pad of Celite, and washed with DCM. The crude material was purified by column chromatography (silica pre-treated with TEA) using Heptanes/DCM (100/0 to 97/3) solvent system. The collected pure fractions were triturated from methanol and the solids were recrystallized from dichloromethane/methanol to afford Compound 453 (0.83 g, 73% yield) as a dark red powder.

Synthesis of Compound 781

Synthesis of 2,6-dimethyl-8-(5-(3,3,3-trifluoropropyl)quinolin-2-yl)benzofuro[2,3-b]pyridine

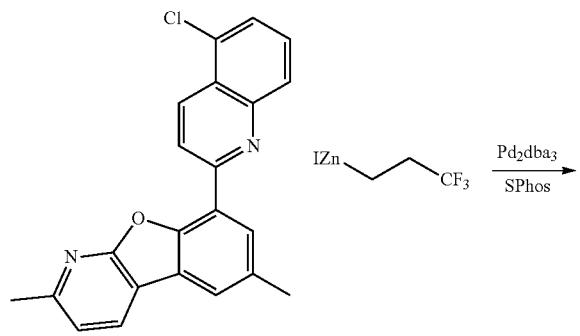

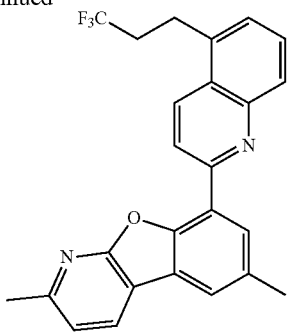

8-(5-chloroquinolin-2-yl)-2,6-dimethylbenzofuro[2,3-b]pyridine (3.40 g, 9.48 mmol), 2'-(dicyclohexylphosphino)-N2,N2,N6,N6-tetramethyl-[1,1'-biphenyl]-2,6-diamine (0.33 g, 0.76 mmol) and diacetoxypalladium (0.09 g, 0.38 mmol) were charged into a flask and diluted with THF (150 mL). This mixture was degassed by bubbling nitrogen followed by the addition of (3,3,3-trifluoropropyl)zinc(II) iodide (40 mL, 11.8 mmol) via syringe. This mixture was stirred at room temperature overnight. Upon completion of the reaction, it was quenched with aqueous ammonium chloride then was extracted two times with 200 mL ethyl acetate. These extracts were dried over magnesium sulfate then were filtered and concentrated under vacuum. The crude residue was purified by column chromatography using 20/80 Ethyl Acetate/Heptanes. The combined fractions were triturated in Heptanes to afford 2,6-dimethyl-8-(5-(3,3,3-trifluoropropyl)quinolin-2-yl)benzofuro[2,3-b]pyridine (2.55 g, 64% yield) as an off-white powder.

Synthesis of Ir(III) Dimer

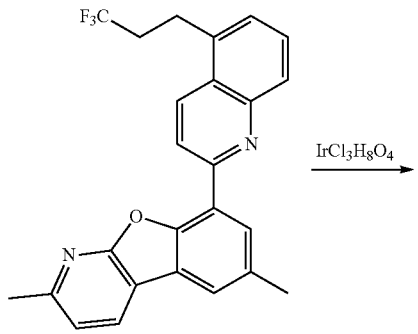

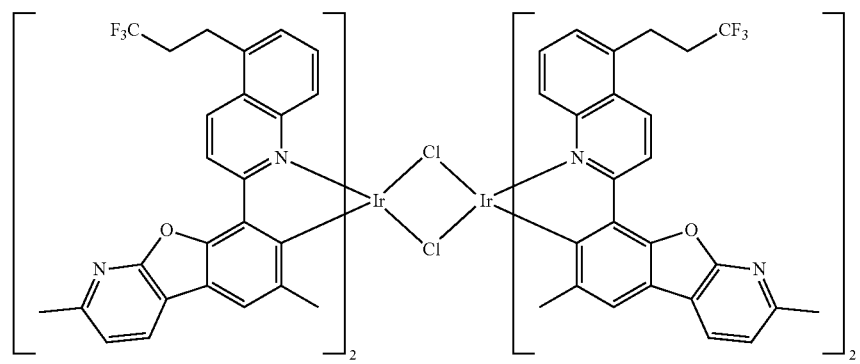

2,6-dimethyl-8-(5-(3,3,3-trifluoropropyl)quinolin-2-yl)benzofuro[2,3-b]pyridine (2.55 g, 6.07 mmol) was solubilized in 2-ethoxyethanol (19 mL) and water (6 mL) and degassed by bubbling nitrogen for 30 minutes. Iridium Chloride (0.56 g, 1.52 mmol) was then added to the solution (some ligand had precipitated) and the reaction was refluxed under nitrogen for 24 hours. After cooling down to room temperature, the solid was filtered, washed with methanol and dried to give Ir(III) Dimer (1.10 g, 68% yield) as a red powder.

Synthesis of Compound 781

Synthesis of Compound 699

Synthesis of 2-(4-fluoro-3,5-dimethylphenyl)-4,4,5,5-tetramethyl-1,3,2-dioxaborolane

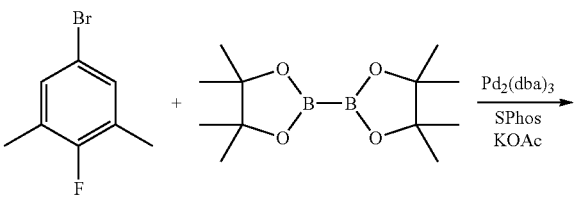

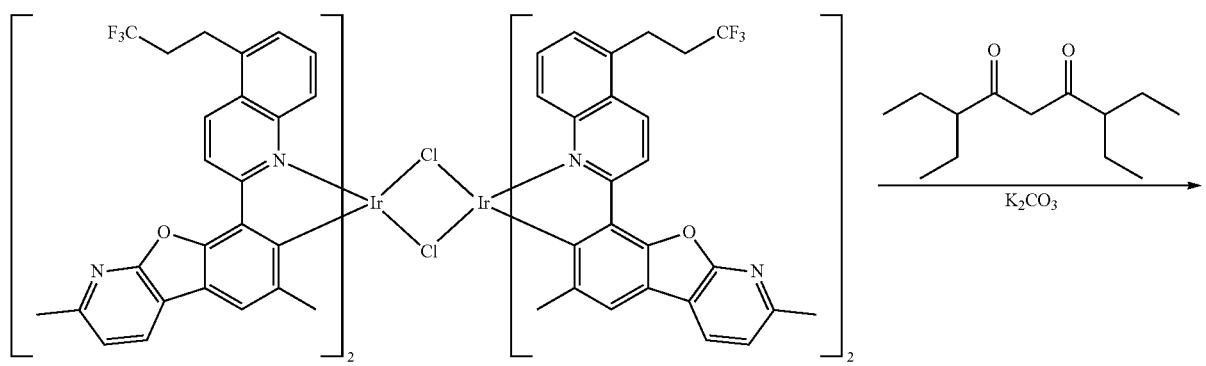

The Ir(III) Dimer (1.00 g, 0.47 mmol) and 3,7-diethyl-nonane-4,6-dione (0.91 g, 4.26 mmol) were diluted in 2-Ethoxyethanol (14 mL) and the mixture was degassed by bubbling nitrogen gas for 15 minutes. K₂CO₃ (0.59 g, 4.26 mmol) was then added and the reaction was stirred at room temperature overnight. The mixture was diluted with dichloromethane, filtered through a pad of Celite, and washed with DCM. The crude material was purified by column chromatography (silica pre-treated with TEA) using Heptanes/dichloromethane 80/20 solvent system. The combined fractions were triturated from methanol and the solids were recrystallized from dichloromethane/methanol once. The title product was obtained as a red powder (0.8 g, 76% yield).

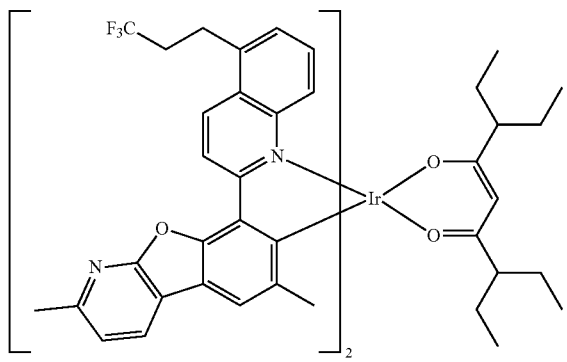

-continued

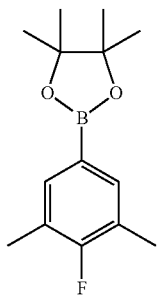

5-bromo-2-fluoro-1,3-dimethylbenzene (20 g, 100 mmol), 4,4,4',4',5,5,5',5'-octamethyl-2,2'-bi(1,3,2-dioxaborolane) (51 g, 200 mmol), Pd$_2$(dba)$_3$ (1.83 g, 2.00 mmol), dicyclohexyl(2',6'-dimethoxy-[1,1'-biphenyl]-2-yl)phosphine (SPhos) (3.28 g, 8.00 mmol), potassium acetate (24.5 g, 250 mmol) and dioxane (600 mL) were combined in a three neck round bottom flask. A condenser was attached then the system was evacuated and purged with nitrogen three times. The reaction was heated to reflux overnight. Upon completion, the reaction was filtered through celite and washed with ethyl acetate. The filtrate was concentrated down to a dark red oil which was dissolved in 400 mL heptane and loaded on to a silica gel plug in a sintered filter funnel. The silica gel was washed with 2 L heptane portion then one 1 L of 98/2 heptane/ethyl acetate to recover most of the product and remove the bispinocolate. These portions were combined and concentrated down to 30 g of yellow oil which was purified with silica gel using heptane to 95/5 heptane/ethyl acetate solvent system. Fractions containing the desired product were combined and concentrated down to 17.5 g of a light yellow solid for a 70% yield.

Synthesis of 7-chloro-4-(4-fluoro-3,5-dimethylphenyl)quinazoline 4,7-dichloroquinazoline (4.0 g, 20.1 mmol), 2-(4-fluoro-3,5-dimethylphenyl)-4,4,5,5-tetramethyl-1,3,2-dioxaborolane (5.53 g, 22.1 mmol), sodium carbonate (5.33 g, 50.2 mmol), palladium tetrakis (0.70 g, 0.60 mmol), dimethoxyethane ("DME") (160 mL), and water (40 mL) were combined in a three neck round bottom flask. A condenser was attached then the system was evacuated and purged with nitrogen three times. The reaction was heated to a vigorous reflux overnight. The reaction was diluted with ethyl acetate, water and brine. The aqueous was partitioned off and the organic was washed once with brine, dried with sodium sulfate, filtered then concentrated down to a yellow solid. The yellow solid was purified with silica gel using DCM to 85/15 DCM/ethyl acetate solvent system to get 4.1 g of light yellow solid for a 71% yield.

Synthesis of 4-(4-fluoro-3,5-dimethylphenyl)-7-(3,3,3-trifluoropropyl)quinazoline

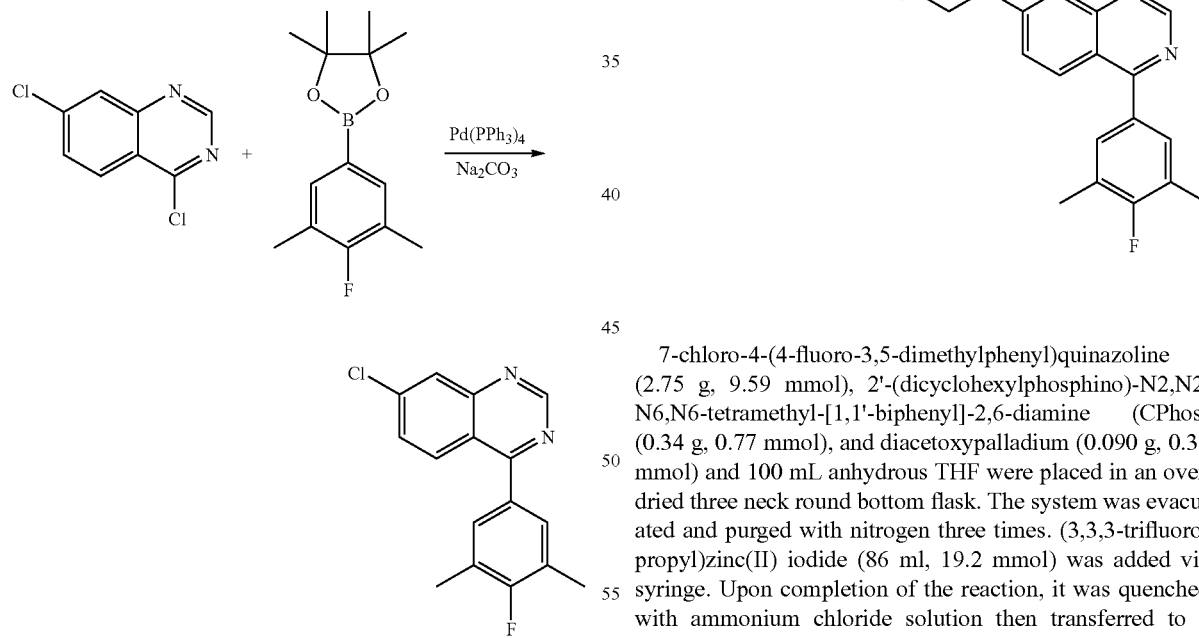

7-chloro-4-(4-fluoro-3,5-dimethylphenyl)quinazoline (2.75 g, 9.59 mmol), 2'-(dicyclohexylphosphino)-N2,N2,N6,N6-tetramethyl-[1,1'-biphenyl]-2,6-diamine (CPhos) (0.34 g, 0.77 mmol), and diacetoxypalladium (0.090 g, 0.38 mmol) and 100 mL anhydrous THF were placed in an oven dried three neck round bottom flask. The system was evacuated and purged with nitrogen three times. (3,3,3-trifluoropropyl)zinc(II) iodide (86 ml, 19.2 mmol) was added via syringe. Upon completion of the reaction, it was quenched with ammonium chloride solution then transferred to a separatory funnel with ethyl acetate. The aqueous was partitioned off, then the organics were washed once with brine, dried with sodium sulfate, filtered and concentrated down. The crude solid was purified with silica gel using DCM to 90/10 DCM/ethyl acetate solvent system to get 3.3 g of a brownish-red solid. The 3.3 g solid was purified using C18 cartridges using 80/20 to 85/15 acetonitrile/water solvent system. The combined fractions were concentrated down then dried in the vacuum oven overnight to get 2.36 g of a white solid for a 71% yield.

Synthesis of Ir(III) Dimer

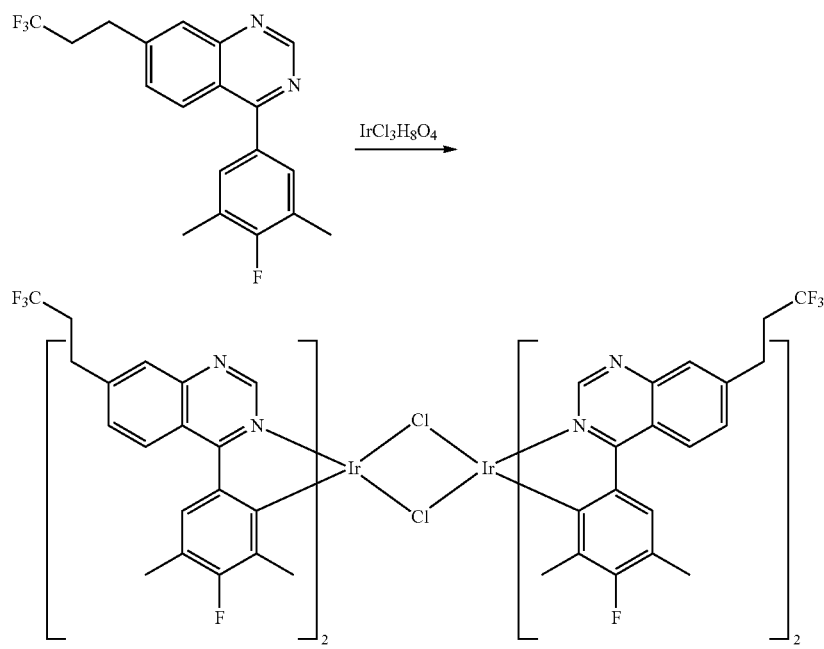

4-(4-fluoro-3,5-dimethylphenyl)-7-(3,3,3-trifluoropropyl)quinazoline (2.56 g, 7.34 mmol) was inserted in a RBF and was solubilized in ethoxythanol (23 mL) and water (8 mL). The mixture was degassed by bubbling nitrogen gas for 15 minutes and then iridium chloride (0.68 g, 1.84 mmol) was inserted and the reaction was heated at 105° C. for 24 hours. The reaction was cooled fown to room temperature, diluted with 10 mL of MeOH, filtered and washed with MeOH. The Ir(III) Dimer (1.50 g, 89% yield) was afforded as an orange powder.

Synthesis of Compound 681

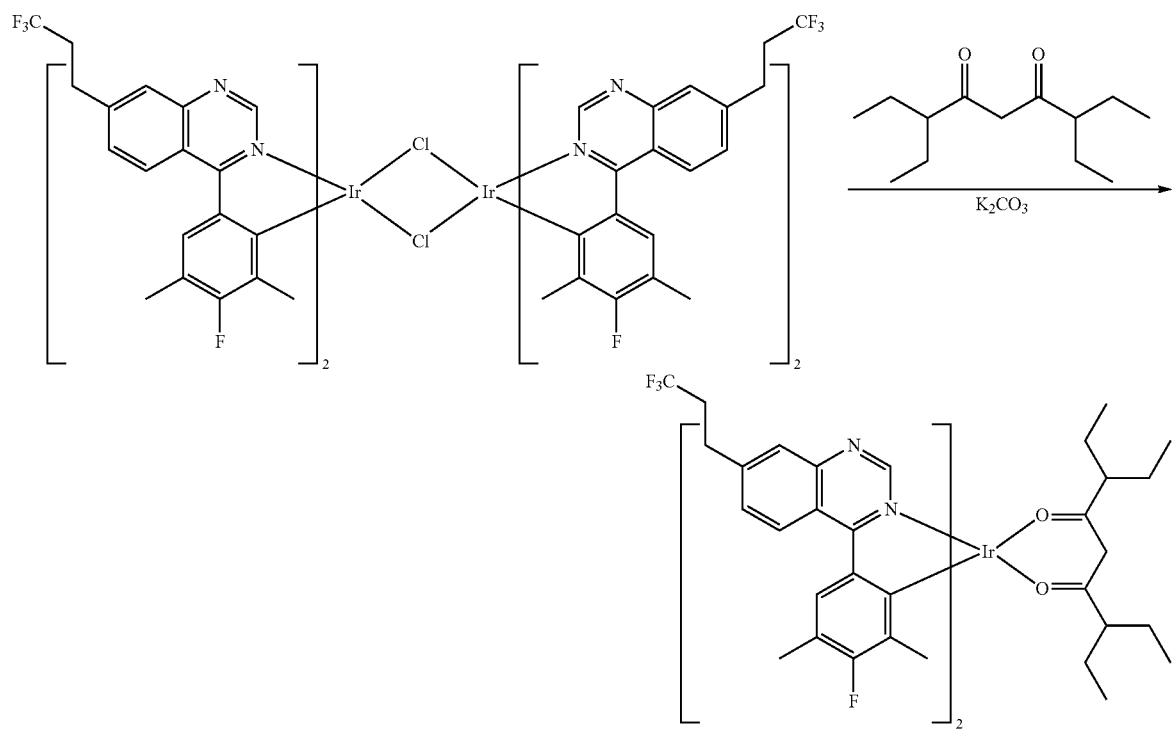

The dimer (1.50 g, 0.81 mmol), 3,7-diethylnonane-4,6-dione (1.73 g, 8.13 mmol), and 2-ethoxyethanol (50 ml) were combined round bottom flask. Nitrogen was bubbled directly into the suspension for 15 min. Potassium carbonate (1.12 g, 8.13 mmol) was added and the reaction was run at room temperature overnight. Upon completion, the reaction was filtered through celite using DCM until the red color came off. The solution was concentrated down to a dark red oily solid, taken up in DCM and adsorbed on to celite. The sample was purified with silica gel to give 0.24 g of dark red solid for a 13% yield.

Synthesis of Compound 22

Synthesis of (4,4,4-trifluoro-3-(trifluoromethyl)butyl)zinc(II) iodide

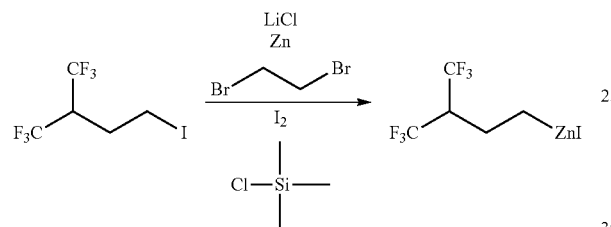

Lithium chloride (1.87 g, 44.1 mmol) was charged into a reaction flask. The flask was evacuated and heated using a heat gun for 10 minutes. The flask was cooled to room temperature and zinc (2.88 g, 44.1 mmol) was added to the flask. The flask was again evacuated and heated using a heat gun for 10 minutes. The flask was cooled to room temperature and THF (80 mL) was syringed into the reaction followed by 1,2-dibromoethane (0.42 mL, 4.90 mmol). This mixture was stirred for 30 minutes in an oil bath set at 60° C. The mixture was cooled to room temperature followed by the addition of chlorotrimethylsilane (0.12 ml, 0.98 mmol) and diiodine (0.25 g, 0.98 mmol) dissolved in 4 mL of THF. The mixture was again stirred for 30 minutes in an oil bath set at 60° C. The mixture was again cooled to room temperature. 1,1,1-trifluoro-4-iodo-2-(trifluoromethyl)butane (7.50 g, 24.5 mmol) was then injected into the reaction mixture via syringe. The heterogeneous reaction mixture was stirred and heated in an oil bath set at 50° C. overnight. The reaction mixture was cooled to room temperature and stirring was stopped. The product was used as is.

Synthesis of 2-(3,5-dimethylphenyl)-5-(4,4,4-trifluoro-3-(trifluoromethyl)butyl)quinoline

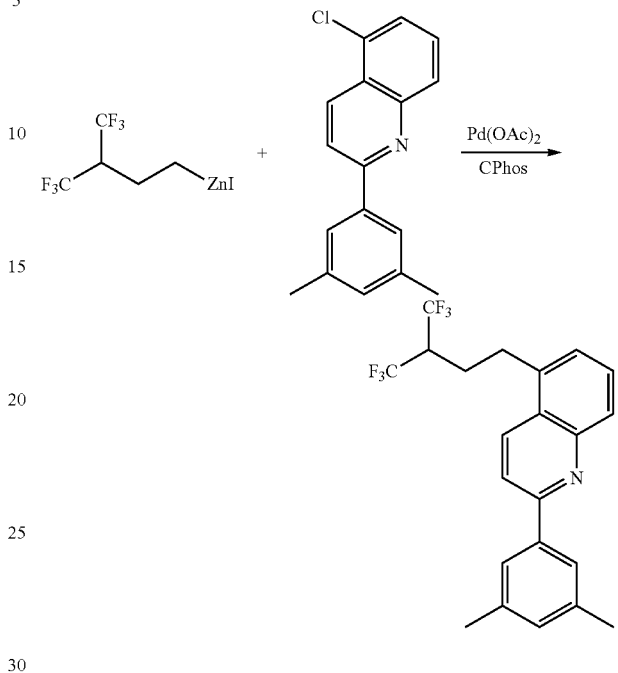

8-(5-chloroquinolin-2-yl)-2,6-dimethylbenzofuro[2,3-b]pyridine (3.40 g, 9.48 mmol), 2'-(dicyclohexylphosphino)-N2,N2,N6,N6-tetramethyl-[1,1'-biphenyl]-2,6-diamine (CPhos) (0.33 g, 0.76 mmol) and diacetoxypalladium (0.09 g, 0.38 mmol) were diluted with THF (190 mL). This mixture was degassed by bubbling nitrogen gas for 15 minutes followed by the addition of (3,3,3-trifluoropropyl)zinc(II) iodide (35 mL, 10.4 mmol) via syringe. This mixture was stirred at room temperature overnight. Upon completion of the reaction, the mixture was quenched with aqueous ammonium chloride then was extracted with 2×200 mL ethyl acetate. These extracts were dried over magnesium sulfate then were filtered and concentrated under vacuum. The crude material was purified via column chromatography using Heptanes/EA (95/5 to 90/10) solvent system. The product was triturated with methanol and then recrystallized from Heptanes to afford 2-(3,5-dimethylphenyl)-5-(4,4,4-trifluoro-3-(trifluoromethyl)butyl)quinoline (2.5 g, 51% yield) as a white solid.

Synthesis of Ir(III) Dimer

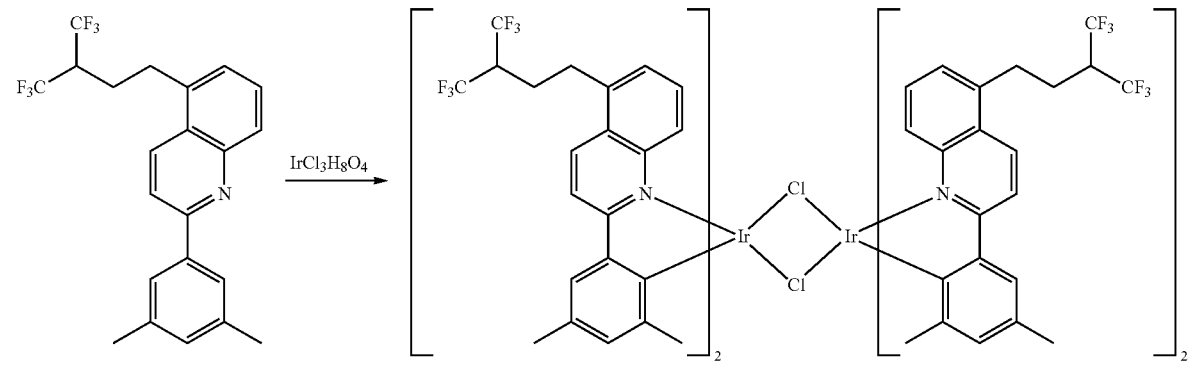

2-(3,5-dimethylphenyl)-5-(4,4,4-trifluoro-3-(trifluoromethyl)butyl)quinoline (2.48 g, 6.02 mmol) was inserted in a round-bottom flask and was solubilized in Ethoxythanol (24 mL) and Water (8 mL). The mixture was degassed by bubbling nitrogen gas for 15 minutes and then Iridium Chloride (0.72 g, 1.94 mmol) was inserted and the reaction was heated at 105° C. for 24 hours. The reaction was cooled down to room temperature, diluted with 10 mL of MeOH, filtered and washed with MeOH to afford the Ir(III) Dimer (1.2 g, 59% yield)

Synthesis of Compound 22

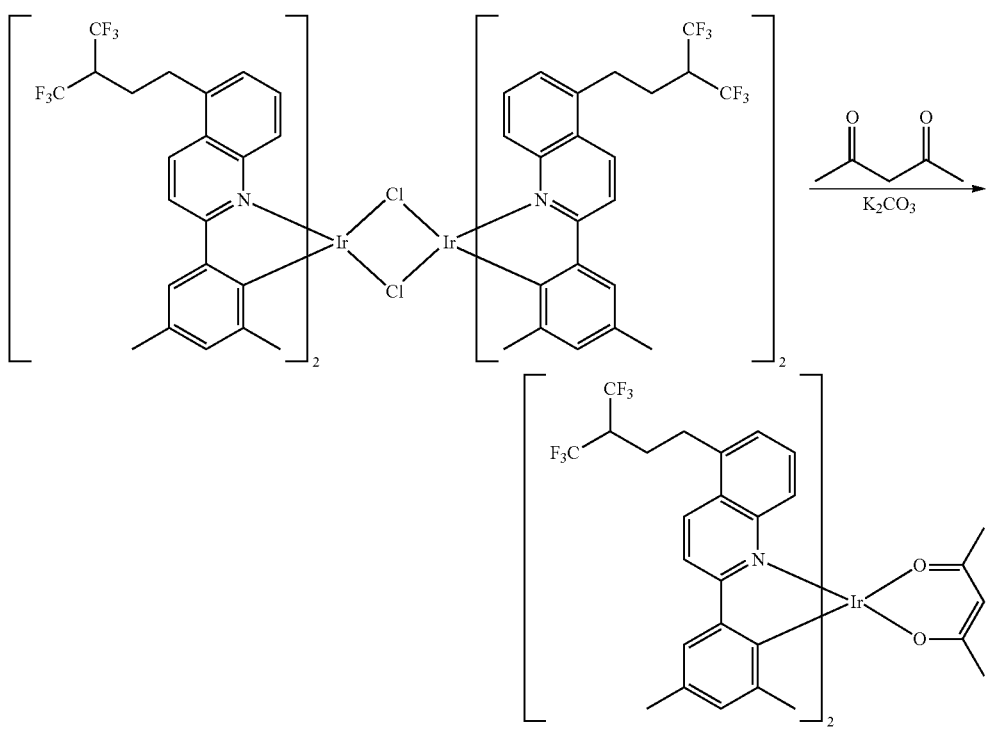

The Ir(III) Dimer (0.50 g, 0.24 mmol) was solubilized in Ethoxyethanol (8 mL) and pentane-2,4-dione (0.25 mL, 2.39 mmol) was added. The mixture was degassed by bubbling nitrogen gas for 15 minutes and $K_2CO_3$ (0.33 g, 2.39 mmol) was then added and the reaction was stirred at room temperature overnight. Upon completion of the reaction, the mixture was diluted with DCM, filtered through celite and washed with DCM. The crude product was coated on Celite and purified via column chromatography (TEA pretreated) using Heptanes/DCM (95/5) solvent system. The product was recrystallized several times (5 times) from MeOH/DCM, EtOH/DCM, and THF/i-PrOH to afford 0.18 g (34% yield) of the target compound.

Synthesis of Compound 473

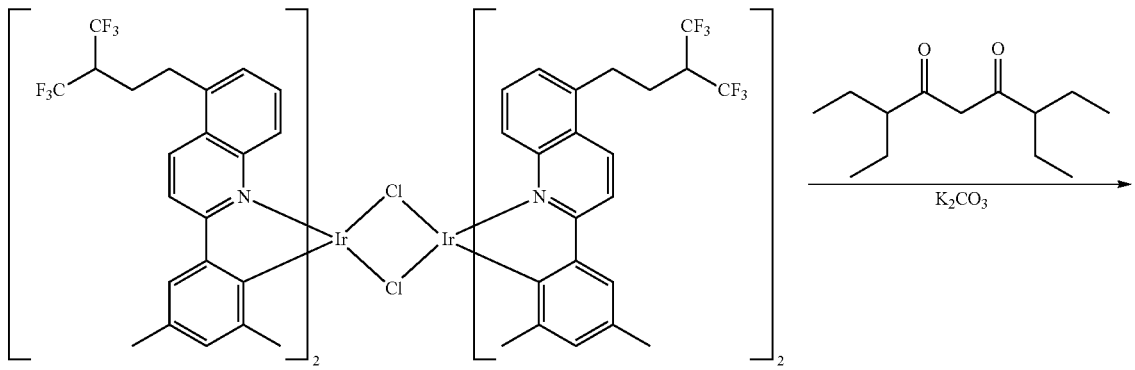

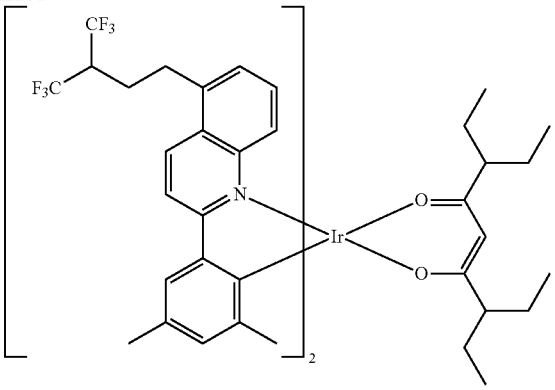

The Ir(III) Dimer (0.70 g, 0.33 mmol) was solubilized in Ethoxyethanol (15 mL) and 3,7-diethylnonane-4,6-dione (0.71 g, 3.34 mmol) was added. The mixture was degassed by bubbling nitrogen gas for 15 minutes and K$_2$CO$_3$ (0.46 g, 3.34 mmol) was then added and the reaction was stirred at room temperature overnight. Upon completion of the reaction, the mixture was diluted with DCM, filtered through celite and washed with DCM. The crude product was coated on Celite and purified via column chromatography (TEA pretreated) using Heptanes/DCM (95/5 to 90/10) solvent system. The product was triturated from methanol to afford 0.21 g (26% yield) of the dopant.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

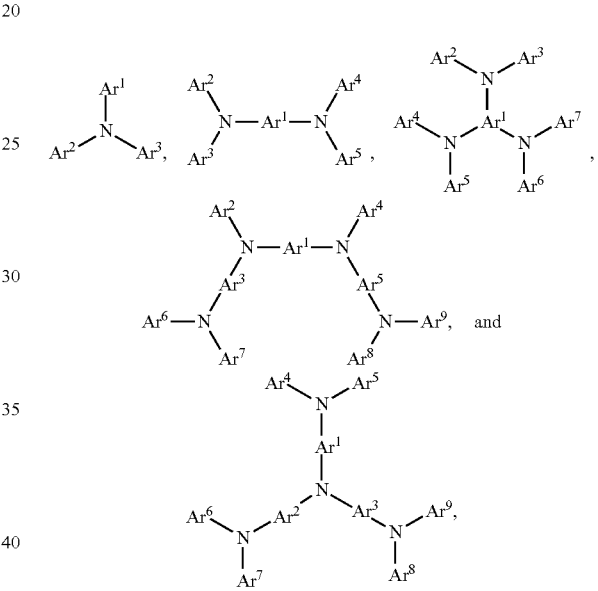

Each of Ar$^1$ to Ar$^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

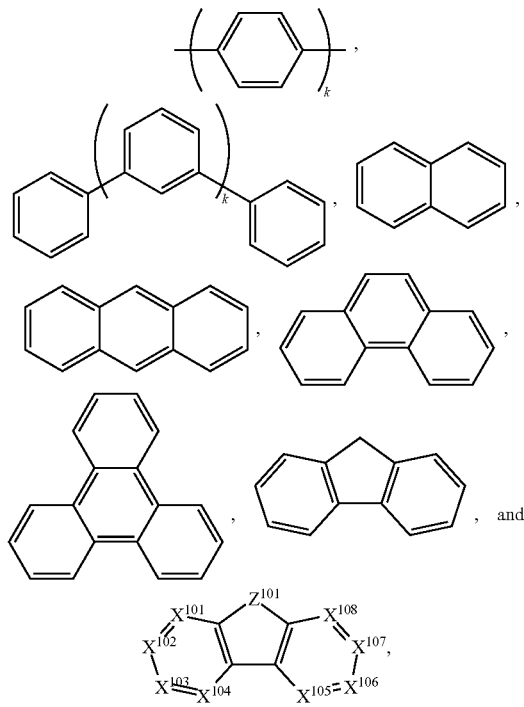

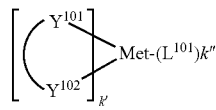

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

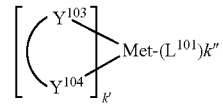

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

$$\left[ \begin{array}{c} Y^{103} \\ Y^{104} \end{array} \right]_{k'} \text{Met-}(L^{101})_{k''}$$

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

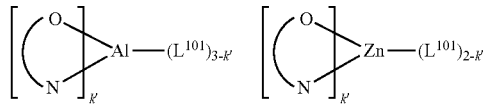

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

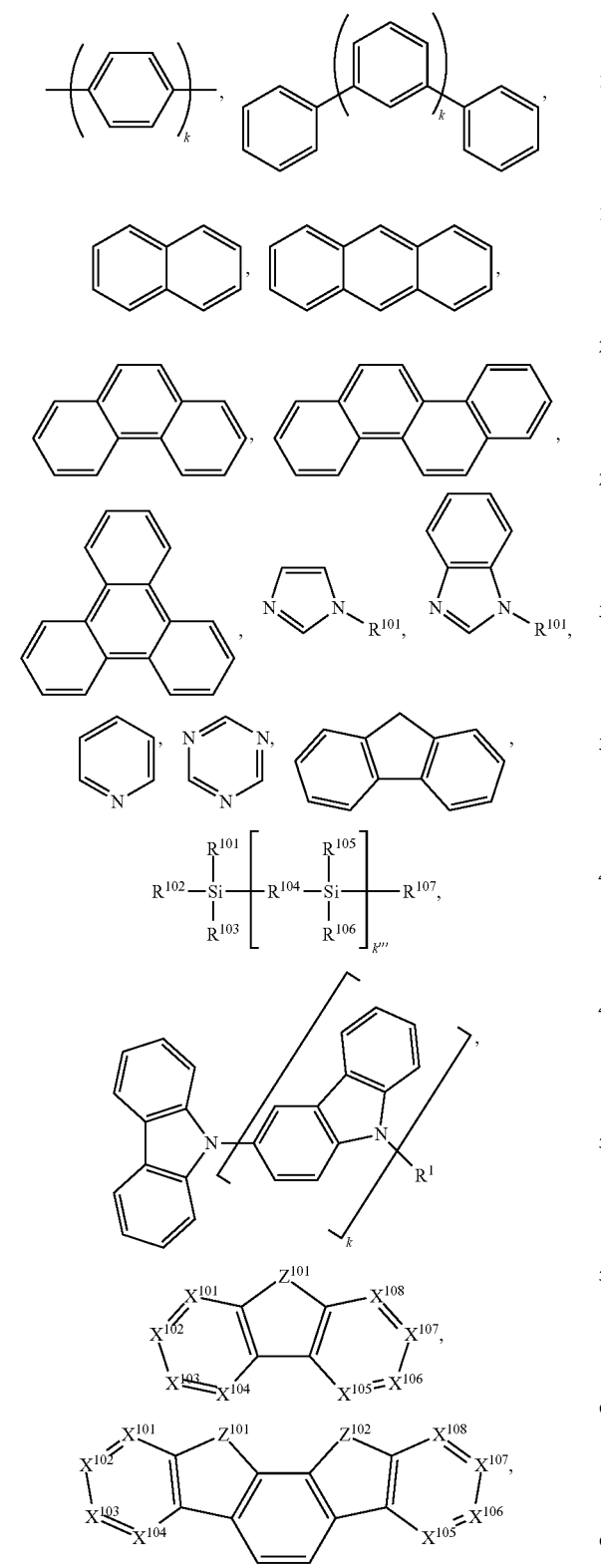

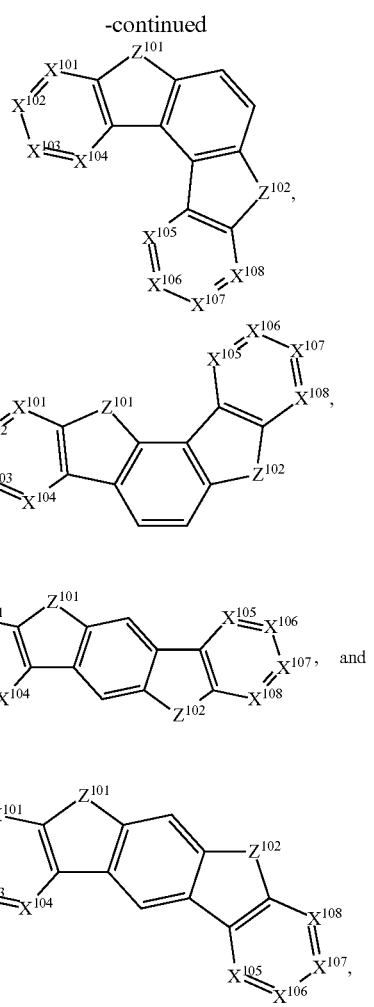

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

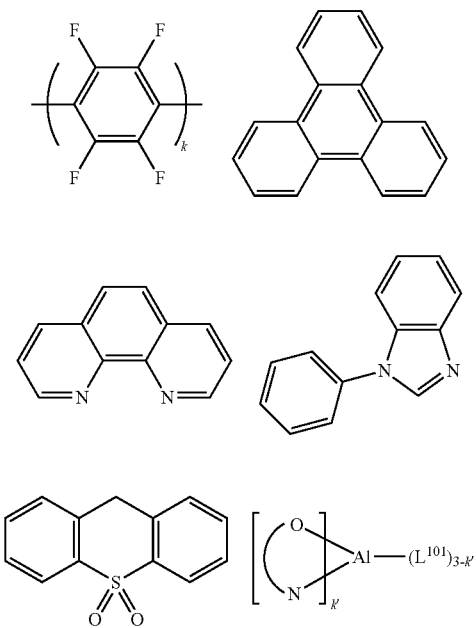

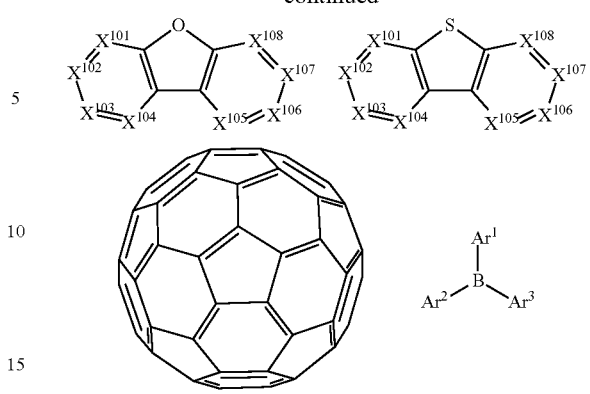

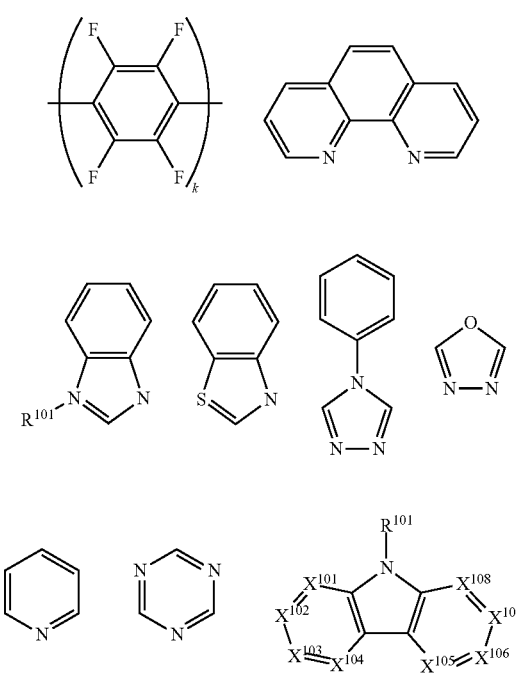

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

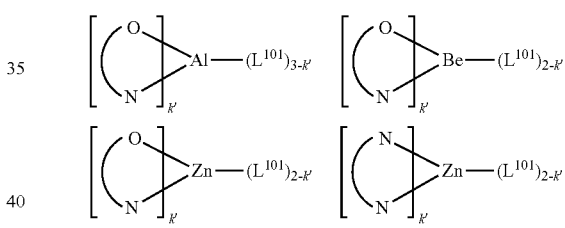

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A
| MATERIAL | EXAMPLES OF MATERIAL | PUBLICATIONS |
|---|---|---|
| Hole injection materials | | |
| Phthalocyanine and porphryin compounds | 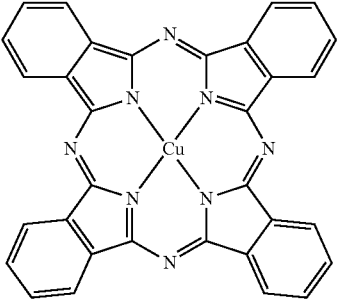 | Appl. Phys. Lett. 69, 2160 (1996) |
| Starburst triarylamines | 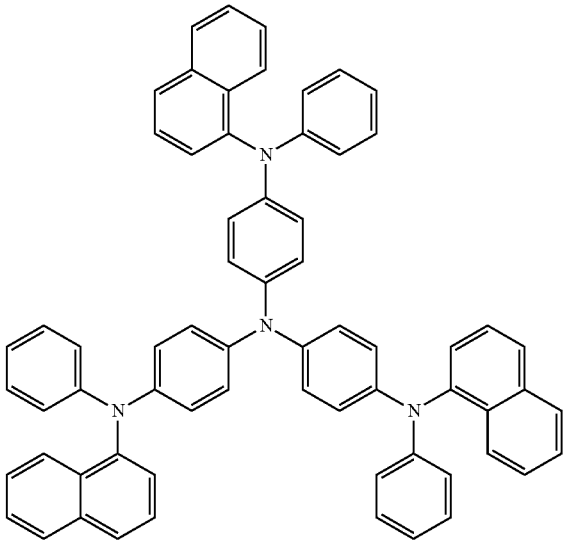 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 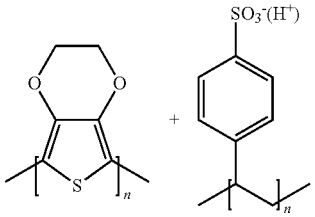 | Synth. Met. 87, 171 (1997) WO2007002683 |
| Phosphonic acid and silane SAMs | 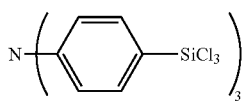 | US20030162053 |

TABLE A-continued
| MATERIAL | EXAMPLES OF MATERIAL | PUBLICATIONS |
|---|---|---|
| Triarylamine or polythiophene polymers with conductivity dopants | 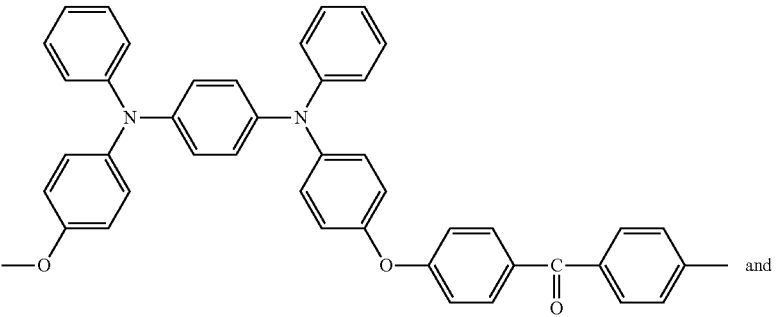 and 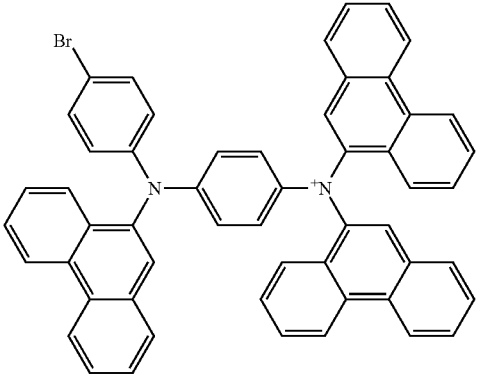 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 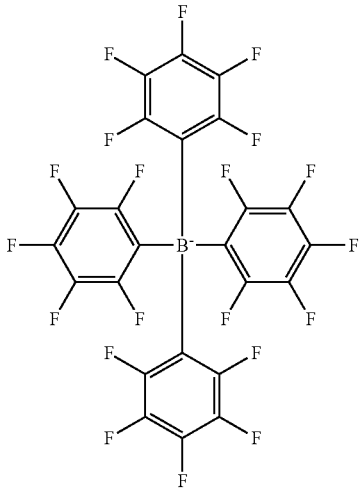 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 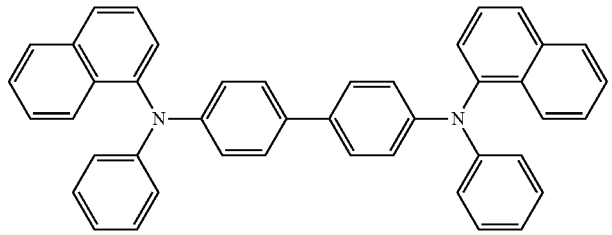 + $MoO_x$ | US20050123751 SID Symposium Digest, 37, 923 (2006) WO2009018009 |

TABLE A-continued
| MATERIAL | EXAMPLES OF MATERIAL | PUBLICATIONS |
|---|---|---|
| n-type semiconducting organic complexes | 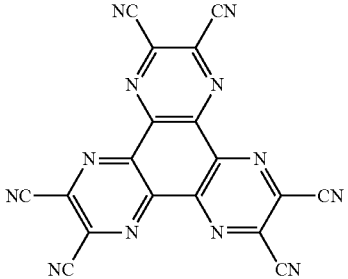 [SMILES: N#Cc1nc2c3nc(C#N)c(C#N)nc3c3nc(C#N)c(C#N)nc3c2nc1C#N] | US20020158242 |
| Metal organometallic complexes | 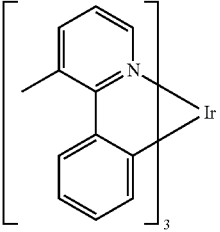 | US20060240279 |
| Cross-linkable compounds | 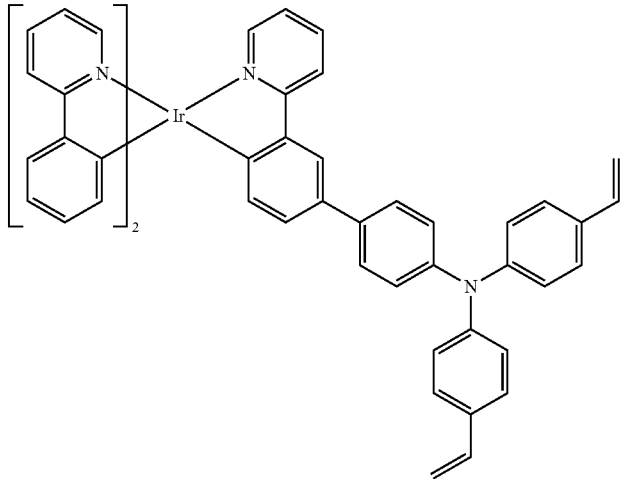 | US20080220265 |
| Polythiophene based polymers and copolymers | 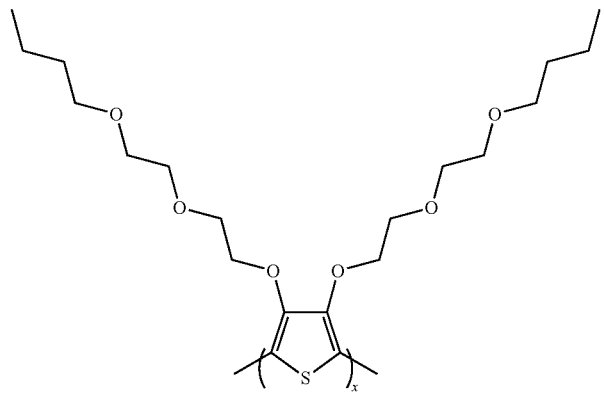 | WO 2011075644<br>EP2350216 |

TABLE A-continued
| MATERIAL | EXAMPLES OF MATERIAL | PUBLICATIONS |
|---|---|---|
| Hole transporting materials | | |
| Triarylamines (e.g., TPD, α-NPD) | 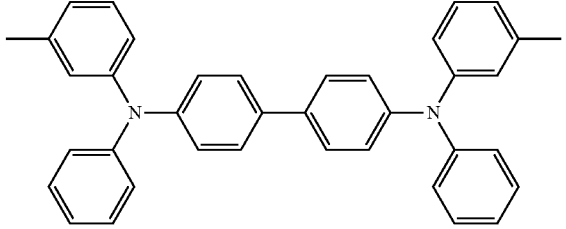 | Appl. Phys. Lett. 51, 913 (1987) |
| | 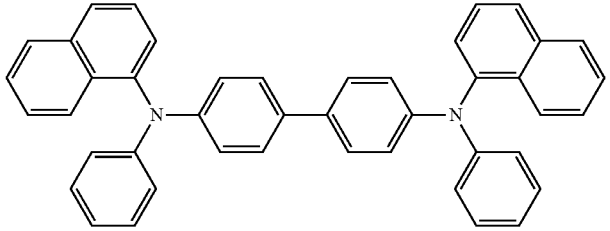 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 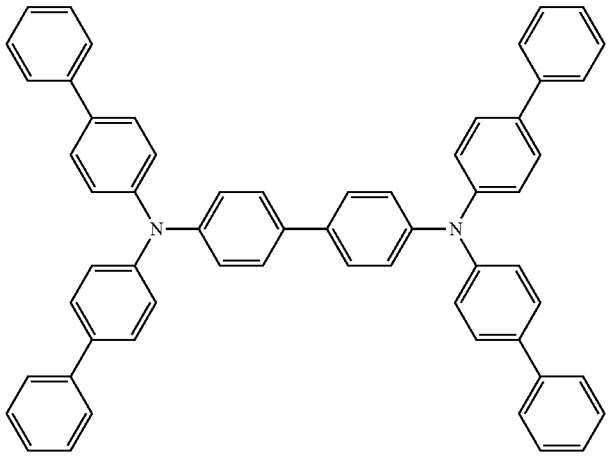 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 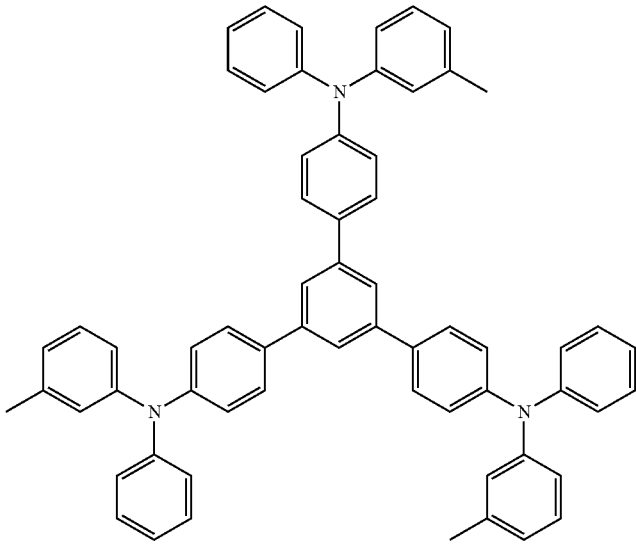 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |

TABLE A-continued
| MATERIAL | EXAMPLES OF MATERIAL | PUBLICATIONS |
| --- | --- | --- |
| Triarylamine with (di)benzothiophene/ (di)benzofuran | 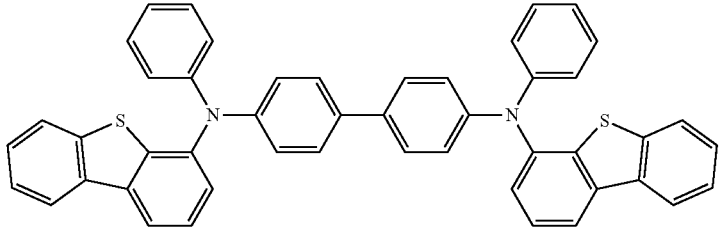 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 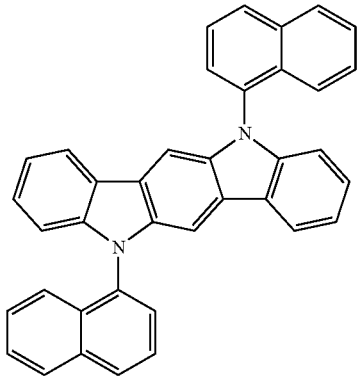 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 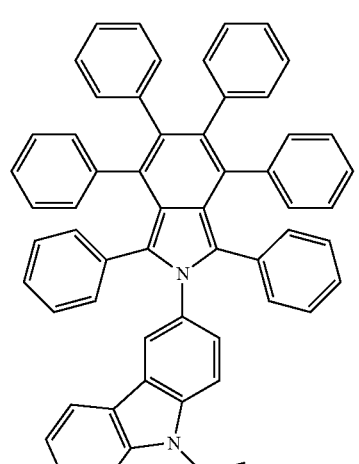 | Chem. Mater. 15, 3148 (2003) |

TABLE A-continued

| MATERIAL | EXAMPLES OF MATERIAL | PUBLICATIONS |
|---|---|---|
| Metal carbene complexes | | US20080018221 |

Phosphorescent OLED host materials

Red hosts

| | | |
|---|---|---|
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |
| | | WO2006072002 |

TABLE A-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |

| MATERIAL | EXAMPLES OF MATERIAL | PUBLICATIONS |
|---|---|---|
| | 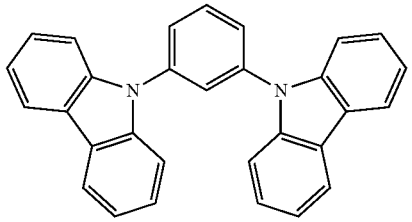 [SMILES: c1cc(-n2c3ccccc3c3ccccc32)cc(-n2c3ccccc3c3ccccc32)c1] | US20030175553 |
| | 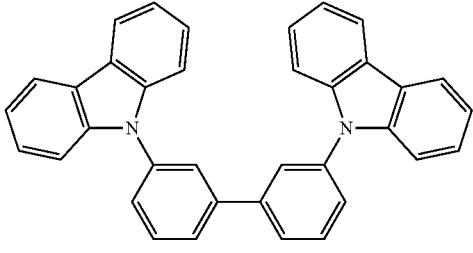 [SMILES: c1cc(-c2cccc(-n3c4ccccc4c4ccccc43)c2)cc(-n2c3ccccc3c3ccccc32)c1] | WO2001039234 |
| Aryltriphenylene compounds | 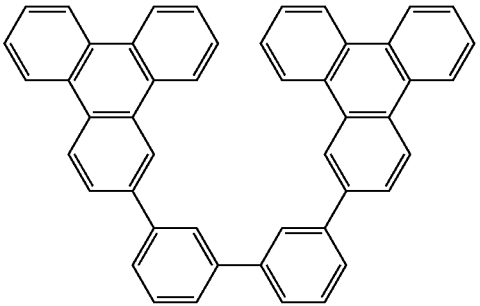 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 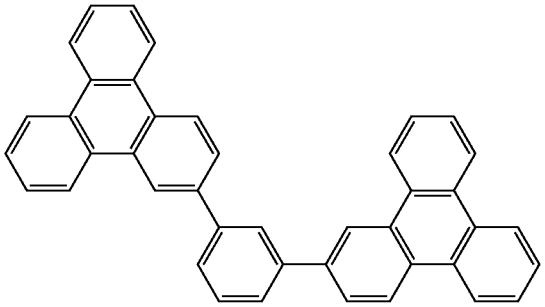 [SMILES: c1cc(-c2ccc3c4ccccc4c4ccccc4c3c2)cc(-c2ccc3c4ccccc4c4ccccc4c3c2)c1] | US20060280965 |
| | 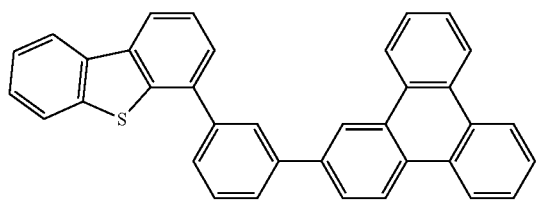 [SMILES: c1cc(-c2ccc3c4ccccc4c4ccccc4c3c2)cc(-c2cccc3c2sc2ccccc23)c1] | WO2009021126 |

TABLE A-continued
| MATERIAL | EXAMPLES OF MATERIAL | PUBLICATIONS |
|---|---|---|
| Poly-fused heteroaryl compounds | 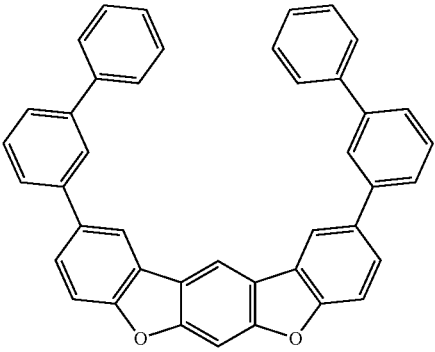 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 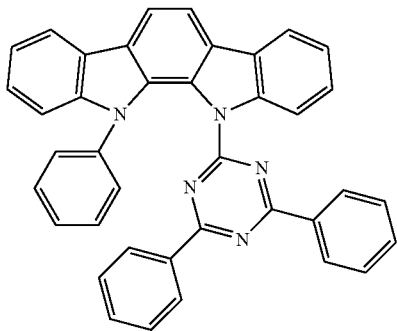 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 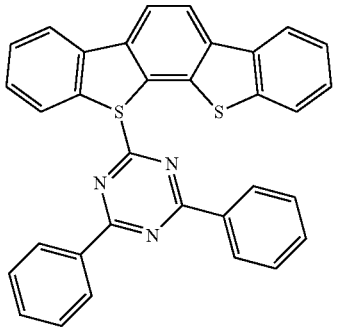 | WO2010107244 |
| Aza-carbazole/<br>DBT/DBF | 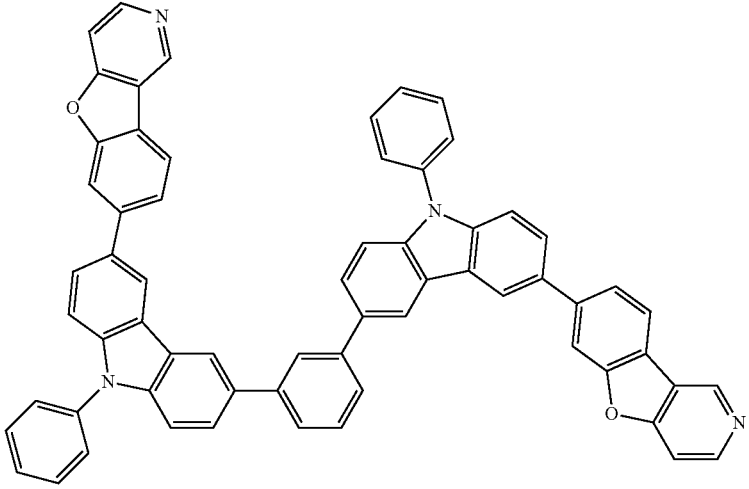 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE A-continued
| MATERIAL | EXAMPLES OF MATERIAL | PUBLICATIONS |
|---|---|---|
| | 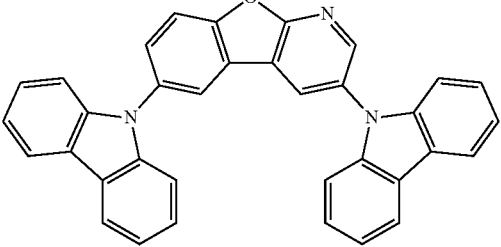 | US20100187984 |
| Polymers (e.g., PVK) | 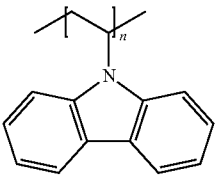 | Appl. Phys. Lett. 77, 2280 (2000) |
| Spirofluorene compounds | 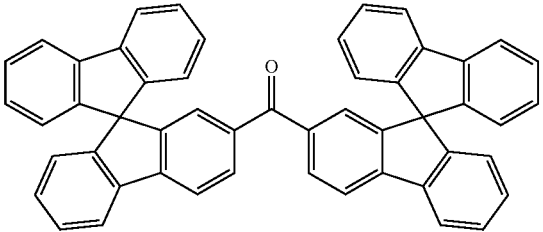 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 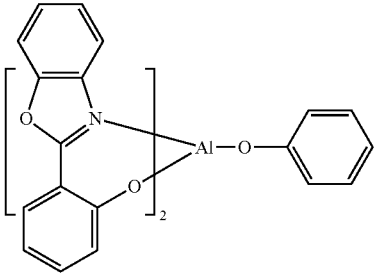 | WO2005089025 |
| | 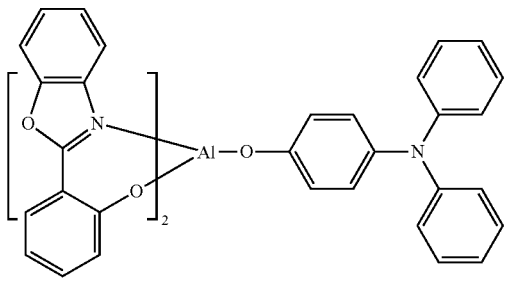 | WO2006132173 |
| | 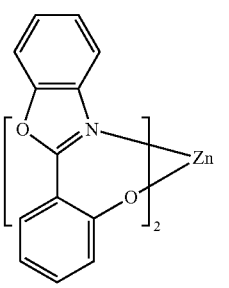 | JP200511610 |

TABLE A-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |

TABLE A-continued

| MATERIAL | EXAMPLES OF MATERIAL | PUBLICATIONS |
|---|---|---|
|  |  | WO2004107822 |
| Tetraphenylene complexes |  | US20050112407 |
| Metal phenoxypyridine compounds |  | WO2005030900 |
| Metal coordination complexes (e.g., Zn, Al with N^N ligands) |  | US20040137268, US20040137267 |

Blue hosts

| Arylcarbazoles |  | Appl. Phys. Lett, 82, 2422 (2003) |
|---|---|---|

| MATERIAL | EXAMPLES OF MATERIAL | PUBLICATIONS |
|---|---|---|
| | 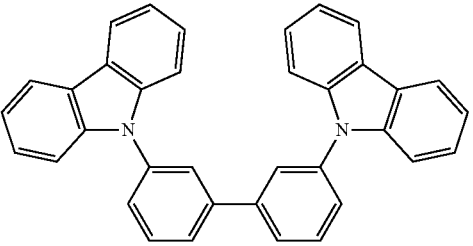 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran- carbazole compounds | 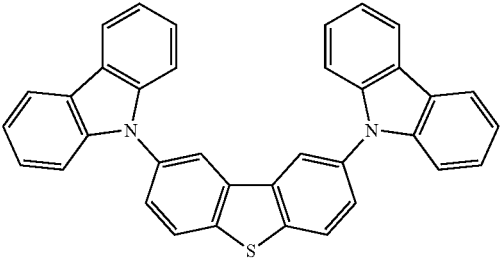 [SMILES: c1ccc2c(c1)c1ccccc1n2-c1ccc2sc3ccc(-n4c5ccccc5c5ccccc54)cc3c2c1] | WO2006114966, US20090167162 |
| | 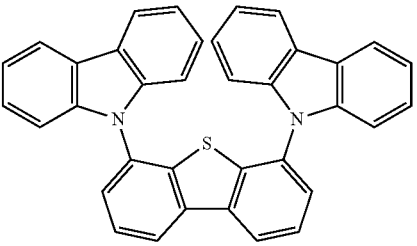 [SMILES: c1cc(-n2c3ccccc3c3ccccc32)c2sc3c(-n4c5ccccc5c5ccccc54)cccc3c2c1] | US20090167162 |
| | 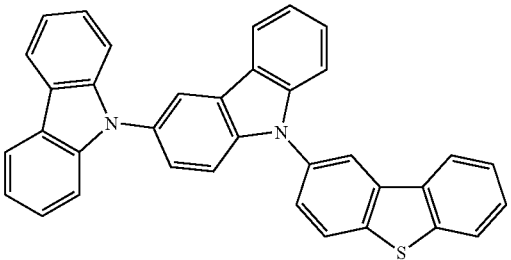 [SMILES: c1ccc2c(c1)sc1ccc(-n3c4ccccc4c4cc(-n5c6ccccc6c6ccccc65)ccc43)cc12] | WO2009086028 |
| | 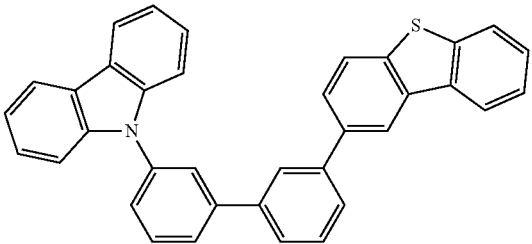 [SMILES: c1cc(-c2cccc(-n3c4ccccc4c4ccccc43)c2)cc(-c2ccc3sc4ccccc4c3c2)c1] | US20090030202, US20090017330 |
| | 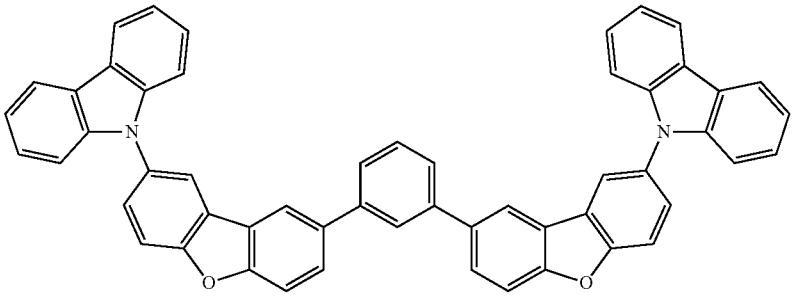 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE A-continued
| MATERIAL | EXAMPLES OF MATERIAL | PUBLICATIONS |
| --- | --- | --- |
| Silicon aryl compounds | 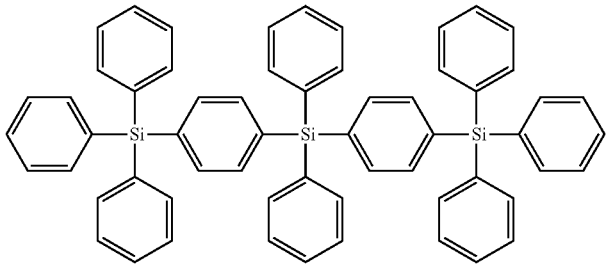 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 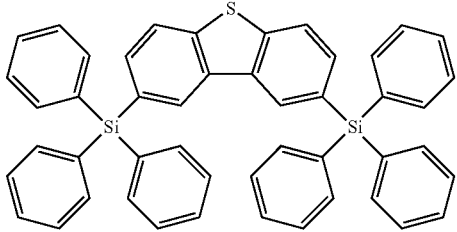 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 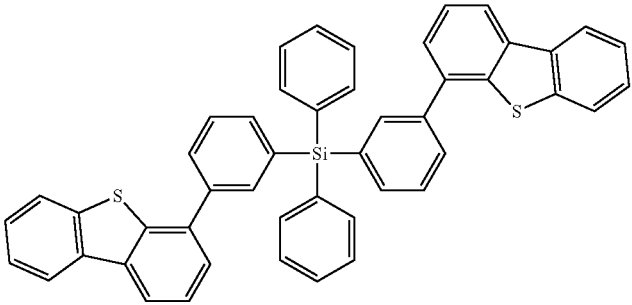 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 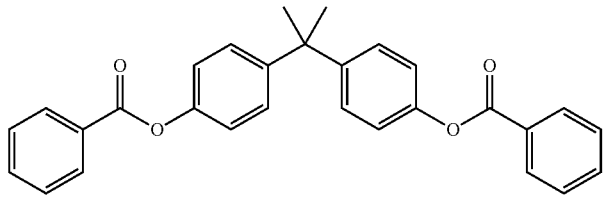 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 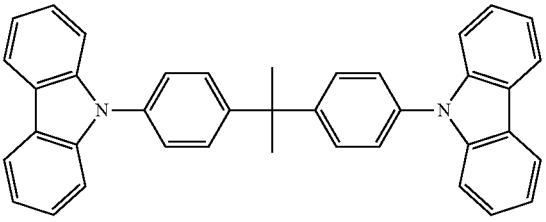 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 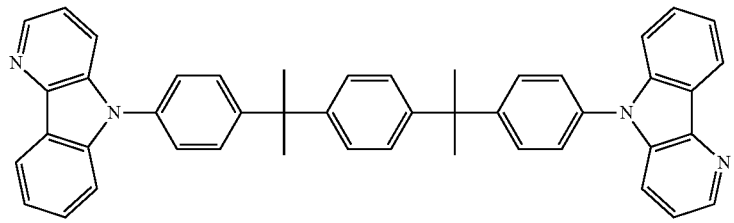 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE A-continued

| MATERIAL | EXAMPLES OF MATERIAL | PUBLICATIONS |
|---|---|---|
| High triplet metal organometallic complex | | U.S. Pat. No. 7,154,114 |

Phosphorescent dopants
Red dopants

| MATERIAL | EXAMPLES OF MATERIAL | PUBLICATIONS |
|---|---|---|
| Heavy metal porphyrins (e.g., PtOEP) | | Nature 395, 151 (1998) |
| Iridium (III) organometallic complexes | | Appl. Phys. Lett. 78, 1622 (2001) |
| | | US20030072964 |
| | | US20030072964 |

TABLE A-continued
| MATERIAL | EXAMPLES OF MATERIAL | PUBLICATIONS |
|---|---|---|
| | 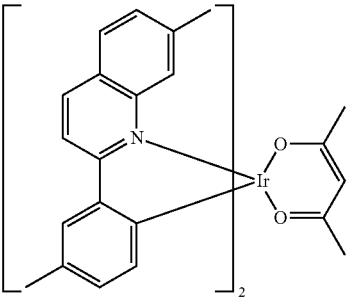 | US20060202194 |
| | 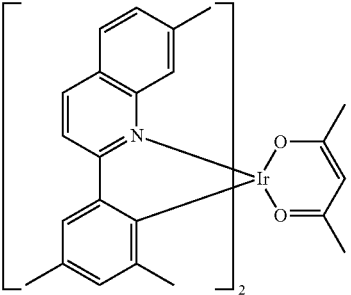 | US20060202194 |
| | 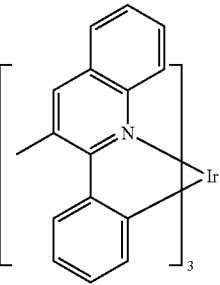 | US20070087321 |
| | 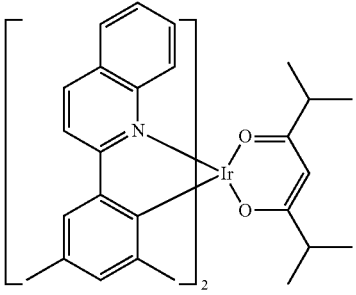 | US20080261076<br>US20100090591 |

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| | | U.S. Pat. No. 7,232,618 |

TABLE A-continued
| MATERIAL | EXAMPLES OF MATERIAL | PUBLICATIONS |
|---|---|---|
| Platinum (II) organometallic complexes | 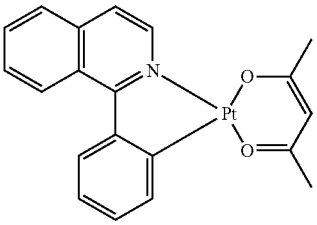 | WO2003040257 |
| | 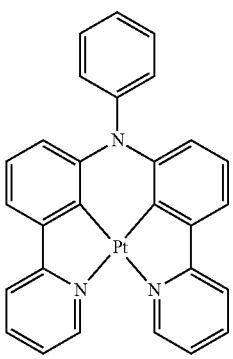 | US20070103060 |
| Osmium (III) complexes | 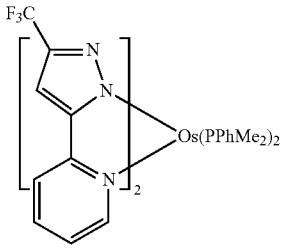 | Chem. Mater. 17, 3532 (2005) |
| Ruthenium (II) complexes | 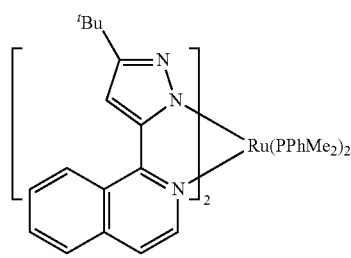 | Adv. Mater. 17, 1059 (2005) |
| Rhenium (I), (II), and (III) complexes | 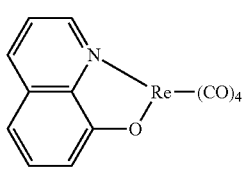 | US20050244673 |

TABLE A-continued
| MATERIAL | EXAMPLES OF MATERIAL | PUBLICATIONS |
|---|---|---|
| | Green dopants | |
| Iridium (III) organometallic complexes | 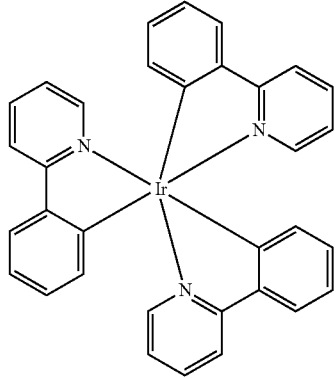<br>and its derivatives | Inorg. Chem. 40, 1704 (2001) |
| | 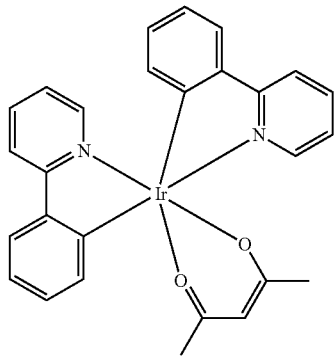 | US20020034656 |
| | 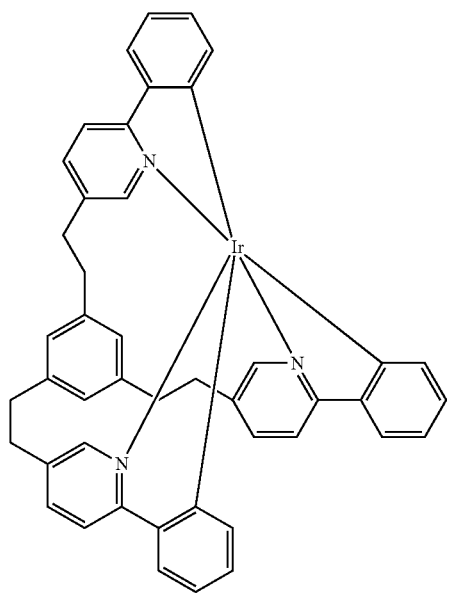 | U.S. Pat. No. 7,332,232 |

TABLE A-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE A-continued

| MATERIAL | EXAMPLES OF MATERIAL | PUBLICATIONS |
|---|---|---|
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

TABLE A-continued

| MATERIAL | EXAMPLES OF MATERIAL | PUBLICATIONS |
|---|---|---|
| | | US 20060008670<br>JP2007123392 |
| | | WO2010086089,<br>WO2011044988 |
| | | Adv. Mater. 16,<br>2003 (2004) |
| | | Angew. Chem.<br>Int. Ed.<br>2006, 45, 7800 |
| | | WO2009050290 |
| | | US20090165846 |

TABLE A-continued

| MATERIAL | EXAMPLES OF MATERIAL | PUBLICATIONS |
|---|---|---|
| | | US20080015355 |
| | | US20010015432 |
| | | US20100295032 |
| Monomer for polymeric metal organometallic compounds | | U.S. Pat. No. 7,250,226, U.S. Pat. No. 7,396,598 |
| Pt (II) organometallic complexes, including polydentated ligands | | Appl. Phys. Lett. 86, 153505 (2005) |

TABLE A-continued
| MATERIAL | EXAMPLES OF MATERIAL | PUBLICATIONS |
|---|---|---|
| | 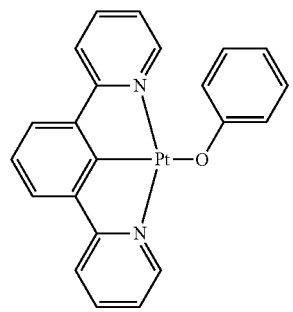 | Appl. Phys. Lett. 86, 153505 (2005) |
| | 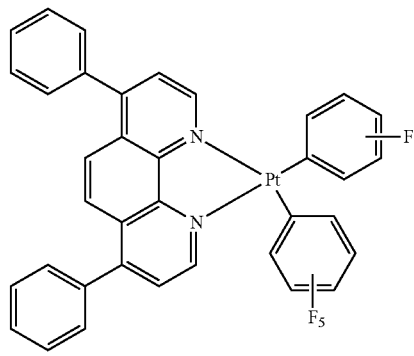 | Chem. Lett. 34, 592 (2005) |
| | 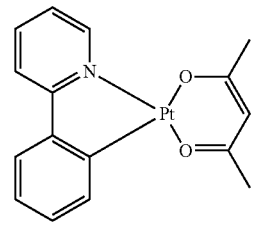 | WO2002015645 |
| | 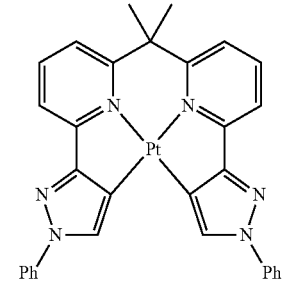 | US20060263635 |
| | 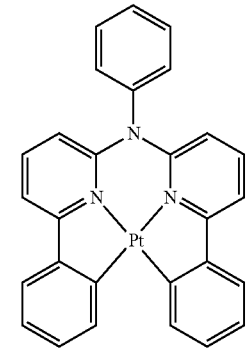 | US20060182992<br>US20070103060 |

TABLE A-continued
| MATERIAL | EXAMPLES OF MATERIAL | PUBLICATIONS |
|---|---|---|
| Cu complexes | 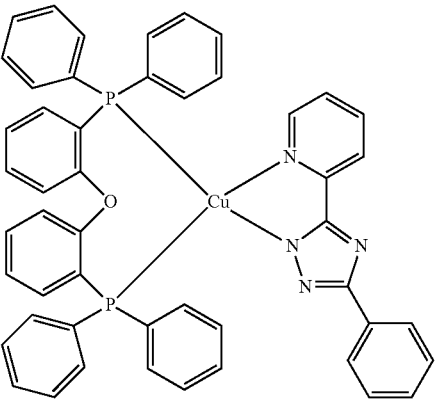 | WO2009000673 |
| | 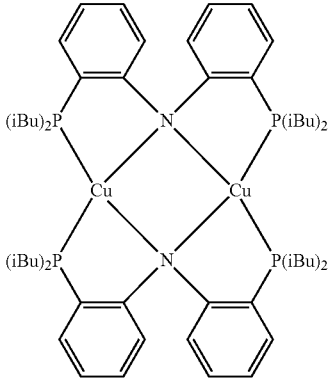 | US20070111026 |
| Gold complexes | 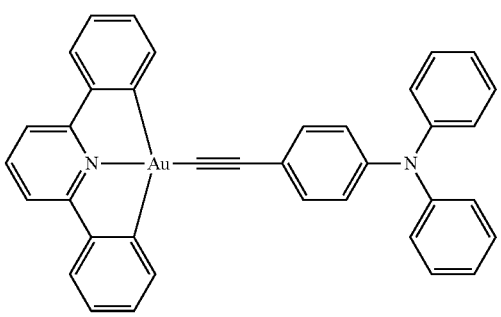 | Chem. Commun. 2906 (2005) |
| Rhenium (III) complexes | 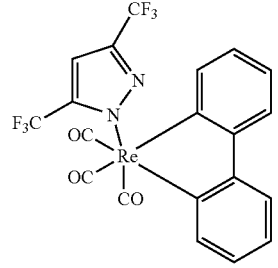 | Inorg. Chem. 42, 1248 (2003) |

TABLE A-continued

| MATERIAL | EXAMPLES OF MATERIAL | PUBLICATIONS |
| --- | --- | --- |
| Osmium (II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE A-continued
| MATERIAL | EXAMPLES OF MATERIAL | PUBLICATIONS |
|---|---|---|
| Blue dopants | | |
| Iridium (III) organometallic complexes | 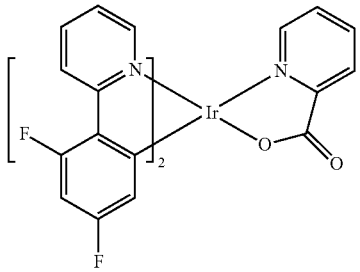 | WO2002002714 |
| | 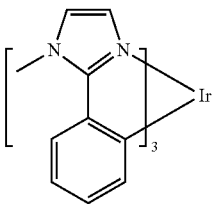 | WO2006009024 |
| | 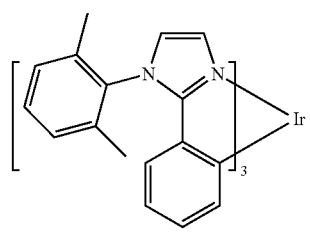 | US20060251923<br>US20110057559<br>US20110204333 |
| | 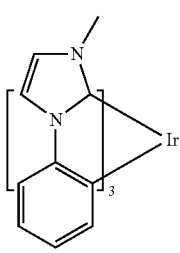 | U.S. Pat. No. 7,393,599,<br>WO2006056418,<br>US20050260441,<br>WO2005019373 |
| | 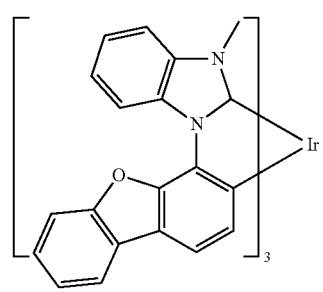 | U.S. Pat. No. 7,534,505 |
| | 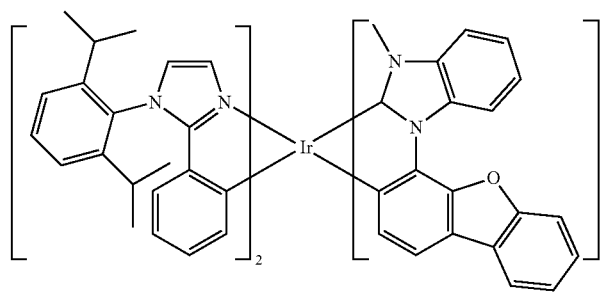 | WO2011051404 |

TABLE A-continued
| MATERIAL | EXAMPLES OF MATERIAL | PUBLICATIONS |
|---|---|---|
| | 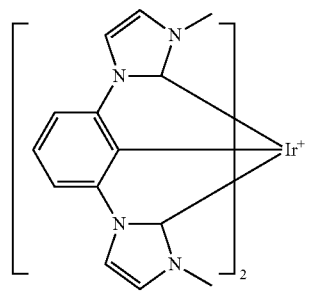 | U.S. Pat. No. 7,445,855 |
| | 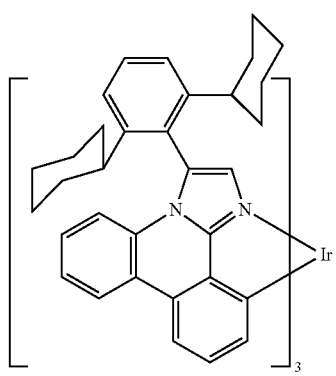 | US20070190359, US20080297033 US20100148663 |
| | 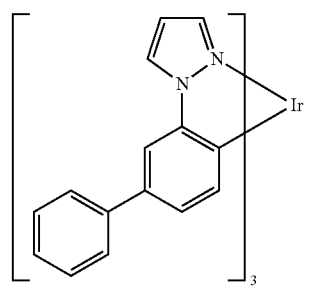 | U.S. Pat. No. 7,338,722 |
| | 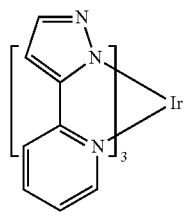 | US20020134984 |
| | 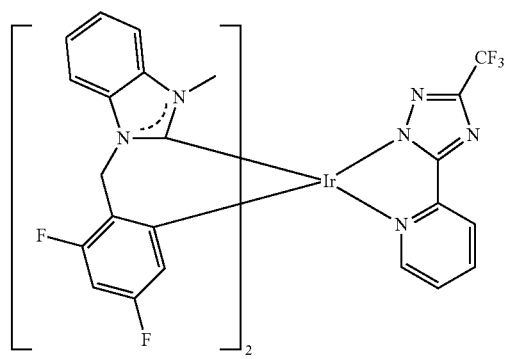 | Angew. Chem. Int. Ed. 47, 4542 (2008) |

TABLE A-continued

| MATERIAL | EXAMPLES OF MATERIAL | PUBLICATIONS |
| --- | --- | --- |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE A-continued
| MATERIAL | EXAMPLES OF MATERIAL | PUBLICATIONS |
|---|---|---|
| | 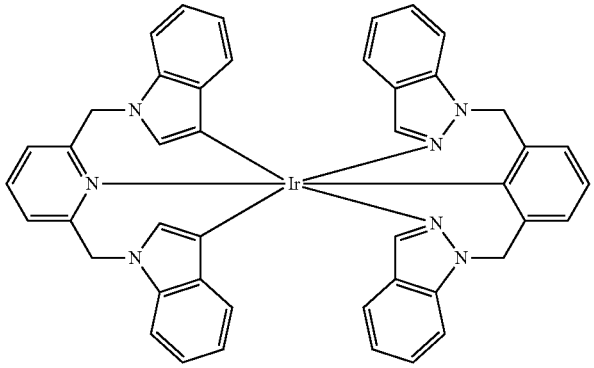 | WO2006082742 |
| Osmium (II) complexes | 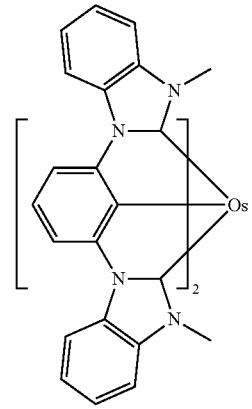 | U.S. Pat. No. 7,279,704 |
| | 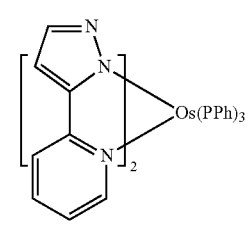 | Organometallics 23, 3745 (2004) |
| Gold complexes | 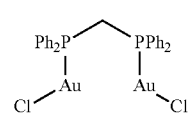 | Appl. Phys. Lett. 74, 1361 (1999) |
| Platinum (II) complexes | 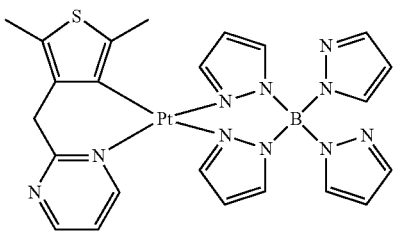 | WO2006098120, WO2006103874 |

… TABLE A-continued

| MATERIAL | EXAMPLES OF MATERIAL | PUBLICATIONS |
| --- | --- | --- |
| Pt tetradentate complexes with at least one metal-carbene bond | 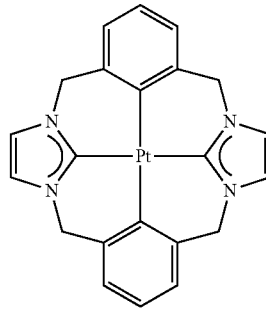 | U.S. Pat. No. 7,655,323 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | 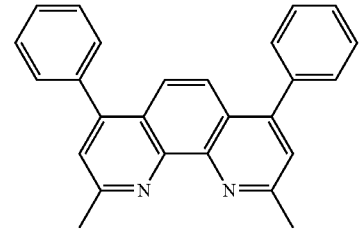 [SMILES: Cc1cc(-c2ccccc2)c2ccc3c(-c4ccccc4)cc(C)nc3c2n1] | Appl. Phys. Lett. 75, 4 (1999) |
|  | 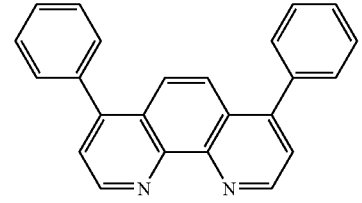 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 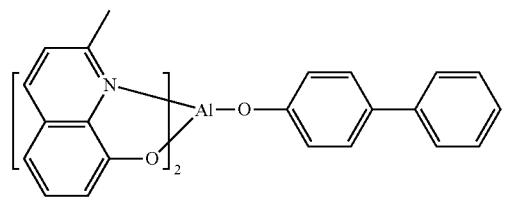 | Appl. Phys. Lett. 81, 162 (2002) |
| 5-member ring electron deficient heterocycles such as triazole, oxadiazole, imidazole, benzoimidazole | 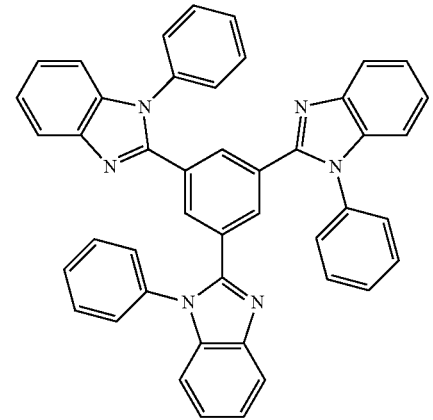 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued
| MATERIAL | EXAMPLES OF MATERIAL | PUBLICATIONS |
|---|---|---|
| Triphenylene compounds | 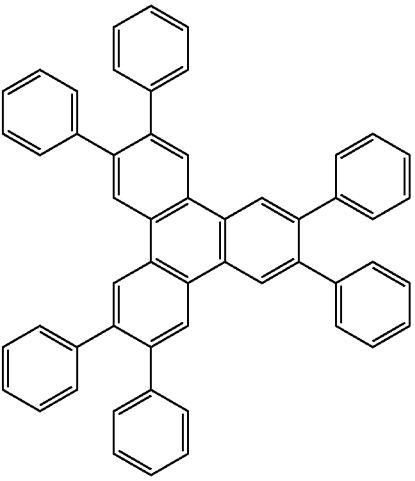 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 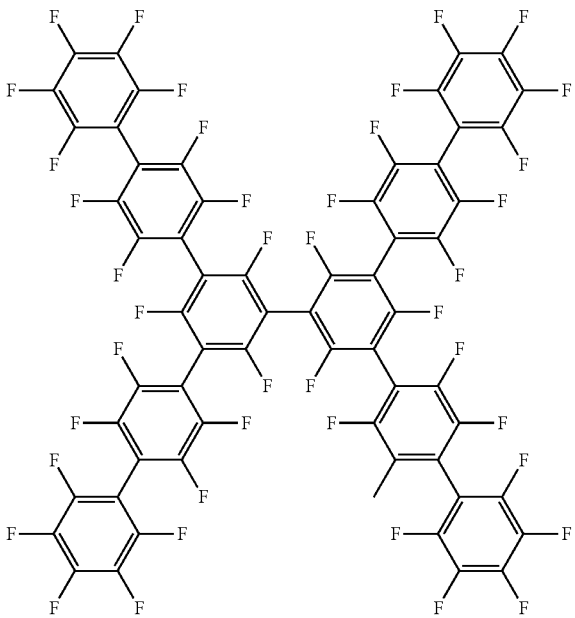 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 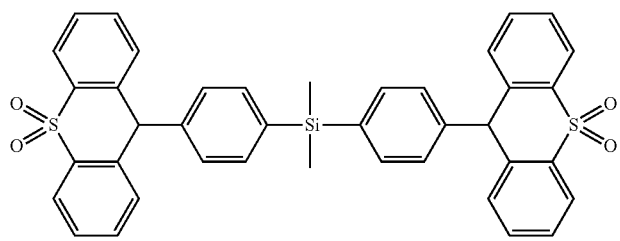 | WO2008132085 |
| Silylated five-membered nitrogen, oxygen, sulfur or phosphorus dibenzoheterocycles | 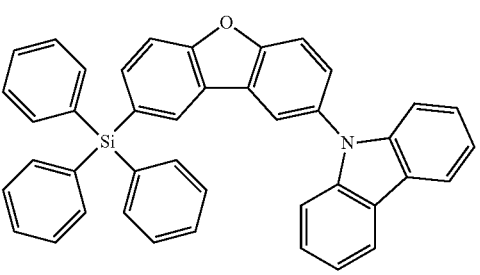 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE A-continued
| MATERIAL | EXAMPLES OF MATERIAL | PUBLICATIONS |
|---|---|---|
| Aza-carbazoles | 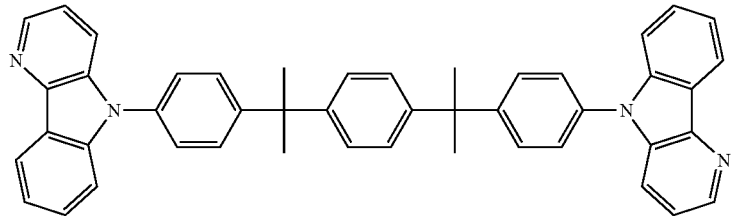 | US20060121308 |
| Electron transporting materials | | |
| Anthracene-benzoimidazole compounds | 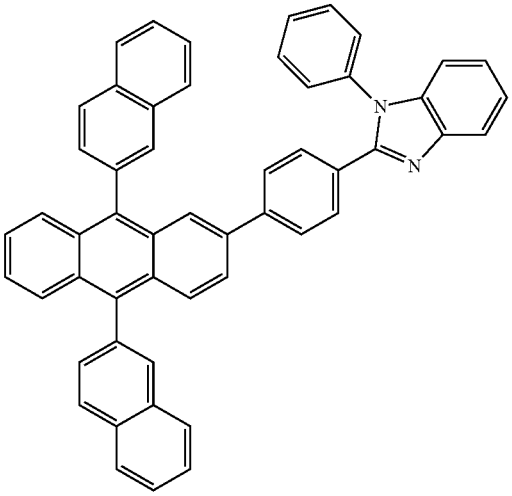 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 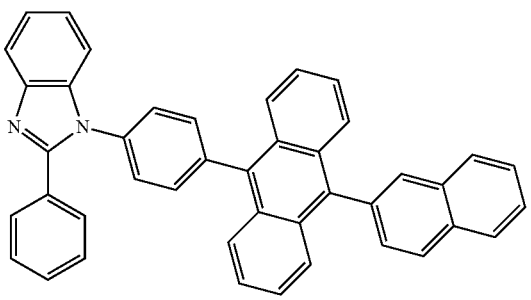 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 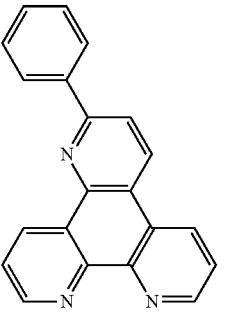 [SMILES: c1ccc(-c2ccc3c4cccnc4c4ncccc4c3n2)cc1] | US20090115316 |

TABLE A-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., Alq₃, Zrq₄) | | Appl. Phys. Lett. 51, 913 (1987) U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE A-continued
| MATERIAL | EXAMPLES OF MATERIAL | PUBLICATIONS |
|---|---|---|
| | 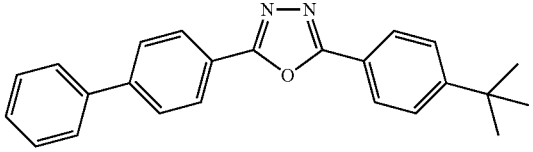 [SMILES: CC(C)(C)c1ccc(-c2nnc(-c3ccc(-c4ccccc4)cc3)o2)cc1] | Appl. Phys. Lett. 55, 1489 (1989) |
| | 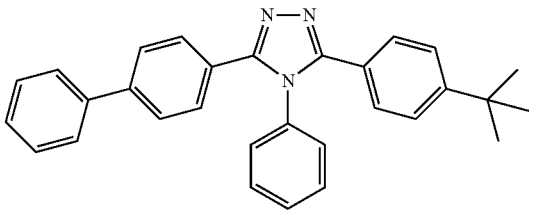 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 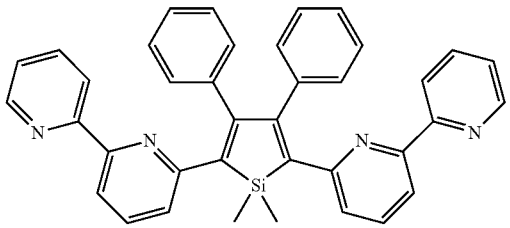 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 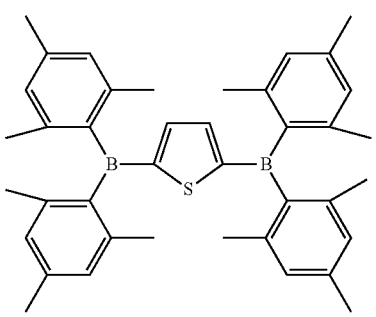 | J. Am. Chem. Soc. 120, 9714 (1998) |
| Fluorinated aromatic compounds | 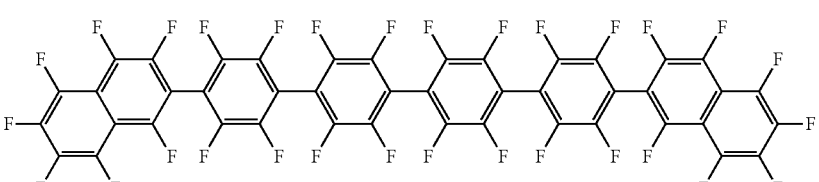 | J. Am. Chem. Soc. 122, 1832 (2000) |
| Fullerene (e.g., C60) | 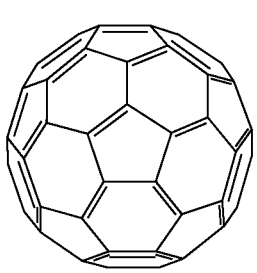 | US20090101870 |

TABLE A-continued

| MATERIAL | EXAMPLES OF MATERIAL | PUBLICATIONS |
|---|---|---|
| Triazine complexes | | US20040036077 |
| Zn (N^N) complexes | | U.S. Pat. No. 6,528,187 |

EXPERIMENTAL

Device Examples

All example devices were fabricated by high vacuum ($<10^{-7}$ Torr) thermal evaporation. The anode electrode was 1200 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package. The organic stack of the device examples consisted of sequentially, from the ITO surface, 100 Å of LG101 (purchased from LG chem) as the hole injection layer (HIL); 400 Å of 4,4'-bis[N-(1-naphthyl)-N-phenylamino]biphenyl (NPD) as the hole transporting layer (HTL); 300 Å of an emissive layer (EML) containing Compound H as a host (79%), a stability dopant (SD) (18%), and Compound 453, Compound 781, or Compound 699 as an emitter; 100 Å of Compound H as a blocking layer; and 450 Å of $Alq_3$ (tris-8-hydroxyquinoline aluminum) as the ETL. The emitter was selected to provide the desired color and the stability dopant (SD) was mixed with the electron-transporting host and the emitter to help transport positive charge in the emissive layer. The Comparative Example device was fabricated similarly to the device examples except that Comparative Compound 1 was used as the emitter in the EML. Table 1 shows the composition of the EML in the device, while the device results and data are summarized in Table 2. As used herein, NPD, compound H, SD, and $AlQ_3$ have the following structures:

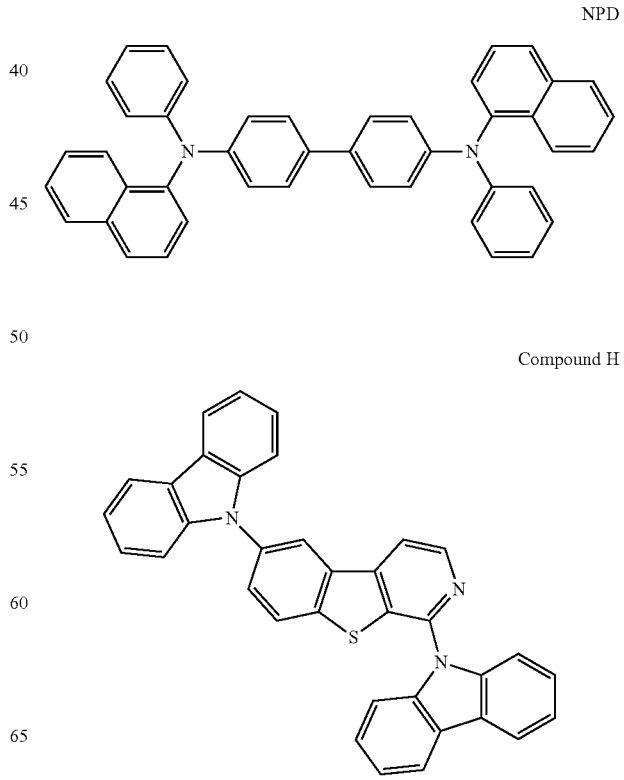

NPD

Compound H

-continued

SD

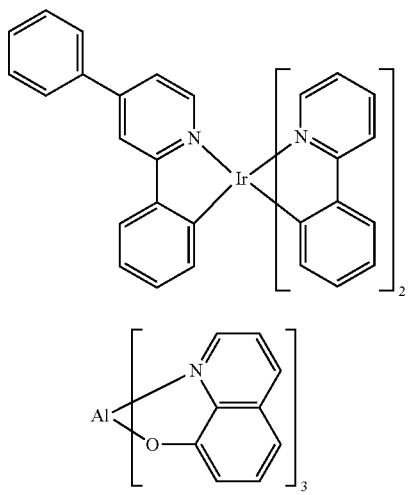

AlQ₃

Comparative Examples

Comparative Compound 1 used in the experiments has the following structure

Compartive Compound 1

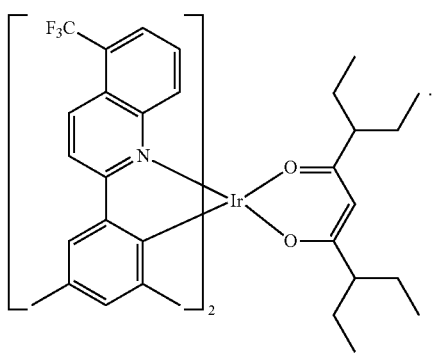

Inventive Compounds

Representative inventive compounds Compound 453, Compound 781, Compound 699, Compound 22, and Compound 473 used in the experiments have the following structures:

Compound 453

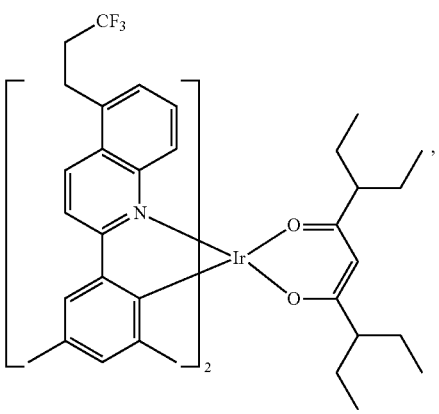

-continued

Compound 781

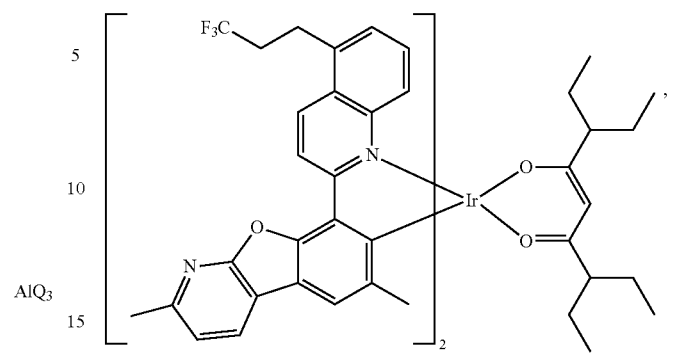

Compound 699

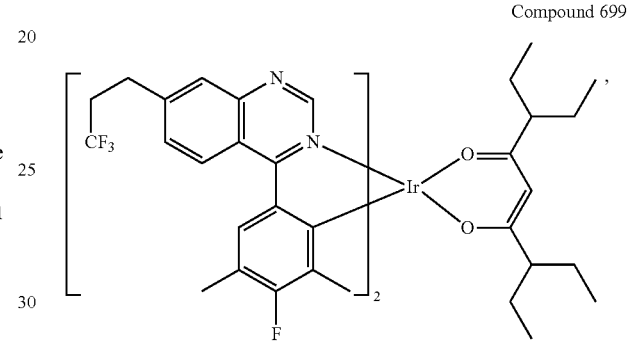

Compound 22

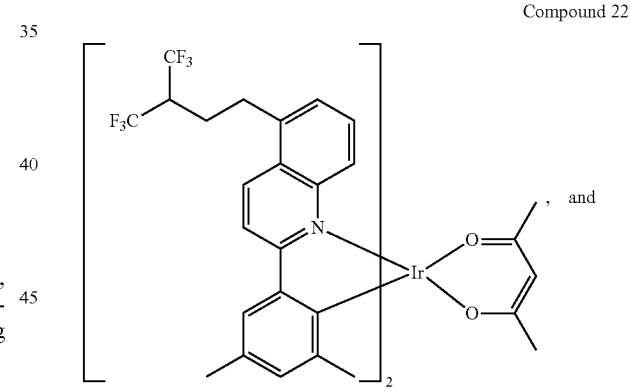

, and

Compound 473

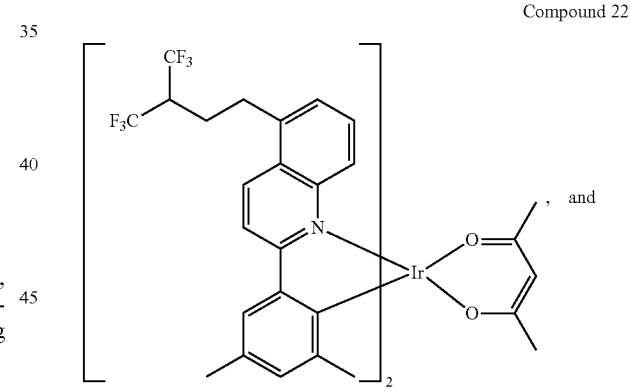

.

Table 1 below lists the compounds used as the emitter dopants in the EML layer of the experimental devices.

TABLE 1

| Example | Emitter |
| --- | --- |
| Inventive Device Example 1 | Compound 453 |
| Inventive Device Example 2 | Compound 781 |
| Inventive Device Example 3 | Compound 699 |
| Inventive Device Example 4 | Compound 22 |
| Inventive Device Example 5 | Compound 473 |
| Comparative Device example 1 | Comparative compound 1 |

Table 2 below provides the device performance data for Inventive Device Examples 1, 2, 3, 4 and 5 and Comparative Device example 1.

TABLE 2

| | 1931 CIE | | λ max | EQE at 1,000 nits | $LT_{95\%}$ at 1,000 nits |
| --- | --- | --- | --- | --- | --- |
| | X | y | [nm] | [cd/A] | [h] |
| Inventive Device Example 1 | 0.65 | 0.35 | 620 | 1.74 | 8.55 |
| Inventive Device Example 2 | 0.64 | 0.36 | 614 | 1.74 | 9.09 |
| Inventive Device Example 3 | 0.66 | 0.34 | 618 | 1.82 | 5.73 |
| Inventive Device Example 4 | 0.65 | 0.35 | 627 | 1.64 | 1.53 |
| Inventive Device Example 5 | 0.65 | 0.35 | 624 | 1.80 | 1.54 |
| Comparative example 1 | 0.66 | 0.34 | 644 | 1.00 | 1.00 |

Table 2 summarizes the performance of the experimental devices. The 1931 CIE values were measured at 10 mA/cm². The luminous efficiency was measured at 1000 cd/m². The EQE, and $LT_{95\%}$ of comparative example 1 were set at a value of 1.00. The values obtained from the inventive examples are relative to that of the comparative example. All of the Inventive Device Examples exhibit higher external quantum efficiencies (EQE) than the Comparative example 1 (1.74, 1.74, 1.82, 1.64, 1.80 vs. 1.00). The lifetime represented by $LT_{95\%}$ at 1,000 nits of the inventive compounds Compound 453, 781, 699, 22, and 473 (Inventive Device Examples 1, 2, 3, 4, and 5) were also more stable than that of the Comparative Compound 1 (Comparative example 1) (8.55, 9.09, 5.73, 1.53, 1.54 vs. 1.00).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A composition comprising a first compound having the formula of $M(L^1)_x(L^2)_y(L^3)_z$;
   wherein M is selected from the group consisting of Ir, Rh, Re, Ru, Os, Pt, Au, and Cu;
   wherein $L^1$, $L^2$, and $L^3$ can be the same or different;
   wherein x is 1, 2, or 3;
   wherein y is 0, 1, or 2;
   wherein z is 0, 1, or 2;
   wherein x+y+z is the oxidation state of the metal M;
   wherein $L^1$, $L^2$, and $L^3$ are each independently selected from the group consisting of:

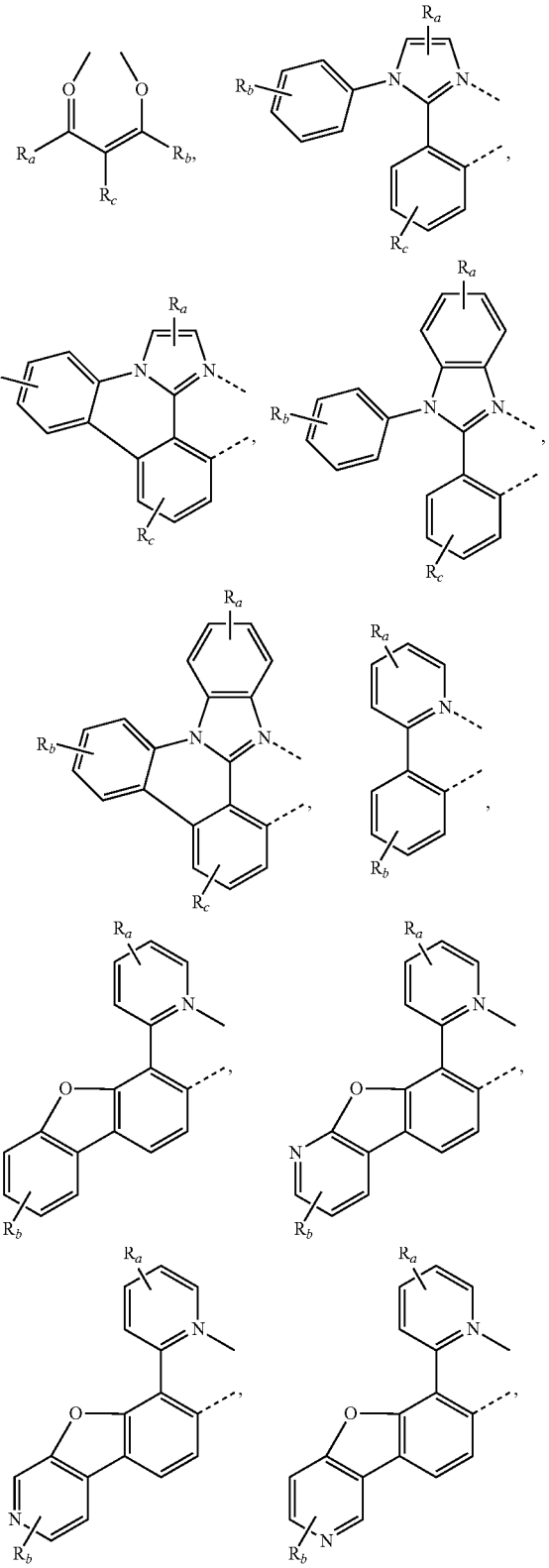

-continued

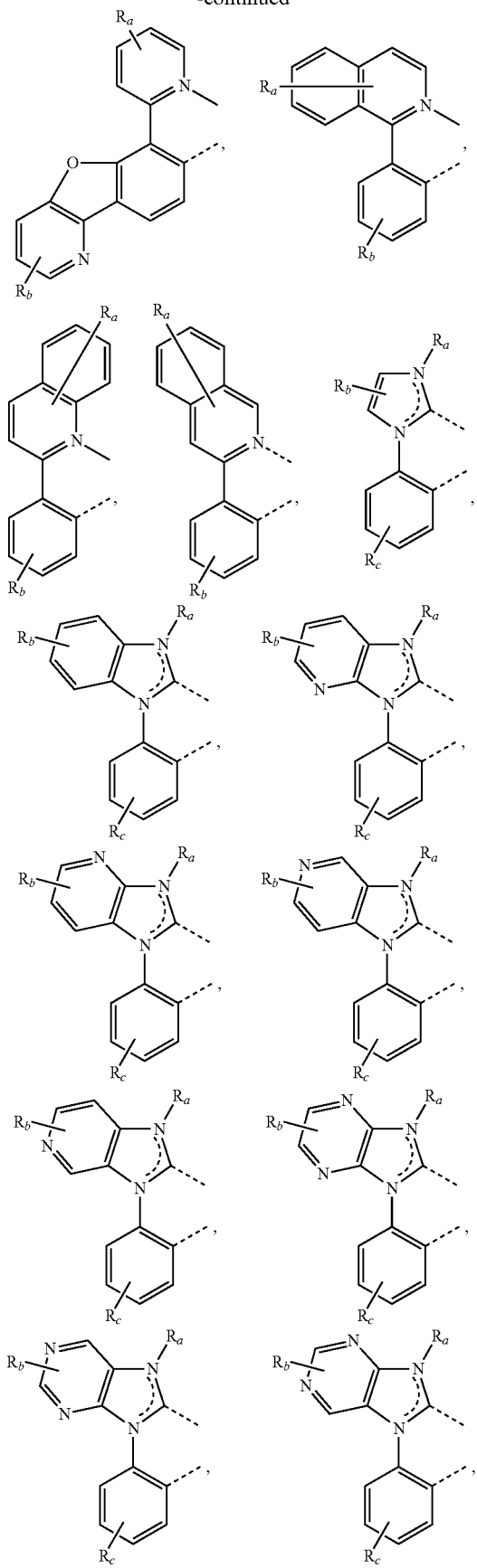

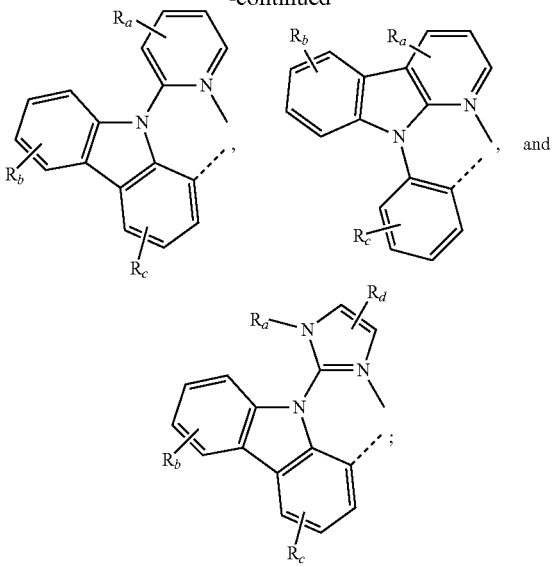

wherein $R_a$, $R_b$, $R_c$, and $R_d$ independently represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, $R_c$, and $R_d$ are optionally joined to form a ring or form a multi-dentate ligand;

wherein at least one of the $R_a$, $R_b$, $R_c$, and $R_d$ includes at least one R, wherein R is selected from the group consisting of partially fluorinated alkyl, partially fluorinated cycloalkyl, and combinations thereof;

wherein each of the at least one R is directly bonded to an aromatic ring;

wherein in each of the at least one R, C having an F attached thereto is separated by at least one carbon atom from the aromatic ring; and wherein when one of $L^1$, $L^2$, and $L^3$ is

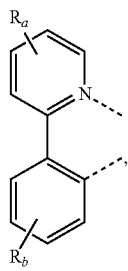

then at least one of the other $L^1$, $L^2$, and $L^3$ is different.

2. The composition of claim 1, wherein the first compound is capable of emitting light from a triplet excited state to a ground singlet state at room temperature.

3. The composition of claim 1, wherein the first compound is a metal coordination complex having a metal-carbon bond.

4. The composition of claim 1, wherein C having an F attached thereto is separated by at least two carbon atoms from the aromatic ring.

5. The composition of claim 1, wherein C having an F attached thereto is separated by at least three carbon atoms from the aromatic ring.

6. The composition of claim 1, wherein each of the at least one R contains at least one $CF_3$ group.

7. The composition of claim 1, wherein the first compound has the formula of $Ir(L^1)_2(L^2)$, wherein $L^1$ has the formula selected from the group consisting of:

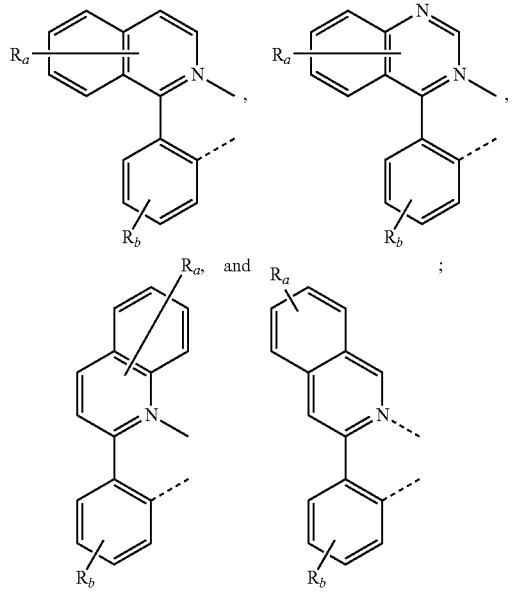

and
wherein $L^2$ has the formula:

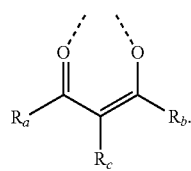

8. The composition of claim 7, wherein $L^2$ has the formula:

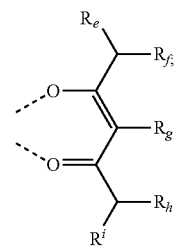

wherein $R_e$, $R_f$, $R_h$, and $R_i$ are independently selected from group consisting of alkyl, cycloalkyl, aryl, and heteroaryl;
wherein at least one of $R_e$, $R_f$, $R_h$, and $R_i$ has at least two carbon atoms;

wherein $R_g$ is selected from group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

9. The composition of claim 1, wherein $L^1$ and $L^2$ are different and each independently selected from the group consisting of:

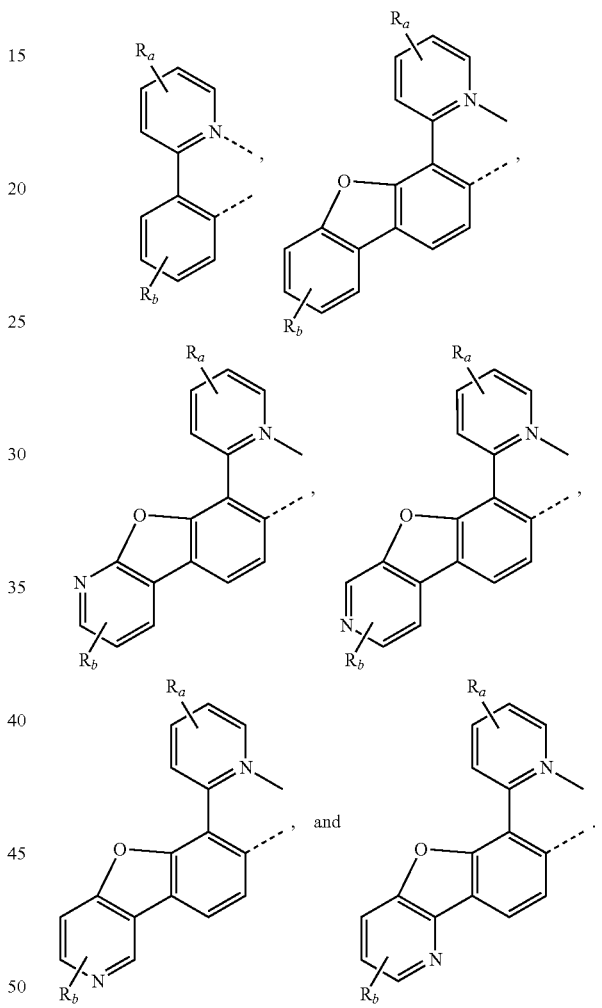

10. The composition of claim 1, wherein $L^1$ and $L^2$ are each independently selected from the group consisting of:

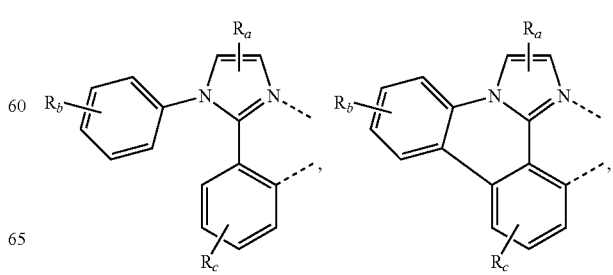

-continued

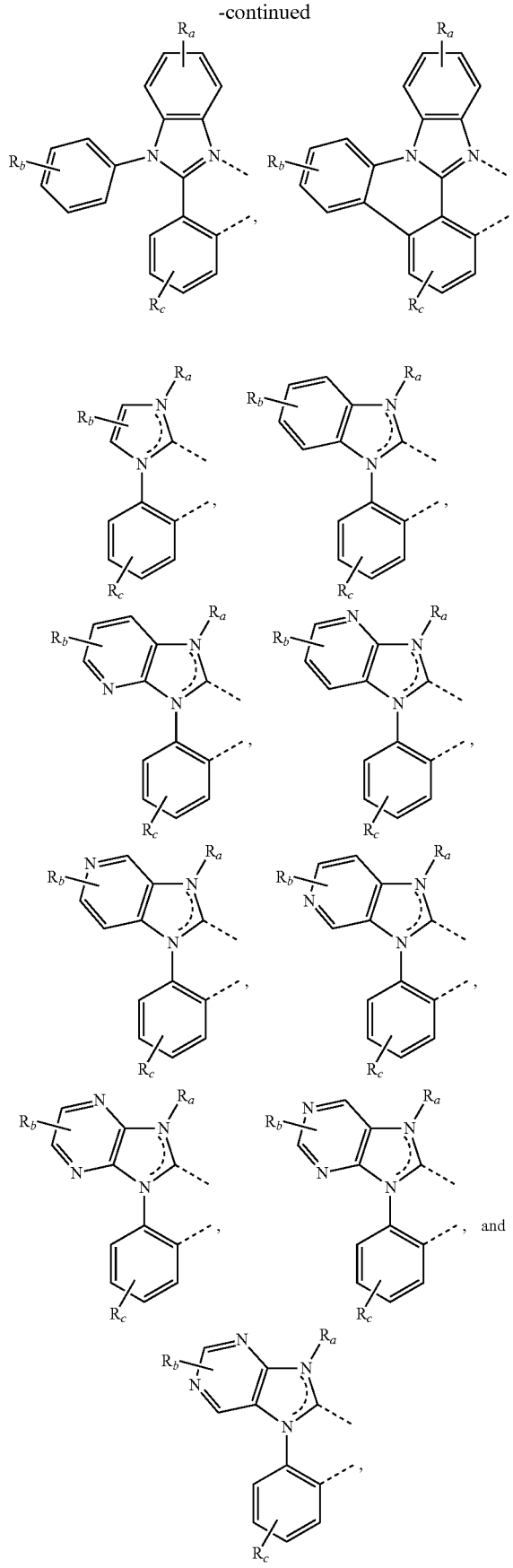

11. The composition of claim 1, wherein the first compound has the formula of Pt(L$^1$)$_2$ or Pt(L$^1$)(L$^2$).

12. The composition of claim 1, wherein at least one of R$_a$, R$_b$, R$_c$, and R$_d$ includes an alkyl or cycloalkyl group that includes CD, CD$_2$, or CD$_3$, wherein D is deuterium.

13. The composition of claim 1, wherein L$^1$, L$^2$, and L$^3$ are each independently selected from the group consisting of:

L$_{A1}$ through L$_{A41}$, each represented by the formula

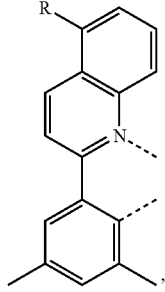

wherein
in L$_{A1}$, R = R$^{A1}$, in L$_{A2}$, R = R$^{A2}$,
in L$_{A3}$, R = R$^{A3}$, in L$_{A4}$, R = R$^{A4}$,
in L$_{A5}$, R = R$^{A5}$, in L$_{A6}$, R = R$^{A6}$,
in L$_{A7}$, R = R$^{A7}$, in L$_{A8}$, R = R$^{A8}$,
in L$_{A9}$, R = R$^{A9}$, in L$_{A10}$, R = R$^{A10}$,
in L$_{A11}$, R = R$^{A11}$, in L$_{A12}$, R = R$^{A12}$,
in L$_{A13}$, R = R$^{A13}$, in L$_{A14}$, R = R$^{A14}$,
in L$_{A15}$, R = R$^{A15}$, in L$_{A16}$, R = R$^{A16}$,
in L$_{A17}$, R = R$^{A17}$, in L$_{A18}$, R = R$^{A18}$,
in L$_{A19}$, R = R$^{A19}$, in L$_{A20}$, R = R$^{A20}$,
in L$_{A21}$, R = R$^{A21}$, in L$_{A22}$, R = R$^{A22}$,
in L$_{A23}$, R = R$^{A23}$, in L$_{A24}$, R = R$^{A24}$,
in L$_{A25}$, R = R$^{A25}$, in L$_{A26}$, R = R$^{A26}$,
in L$_{A27}$, R = R$^{A27}$, in L$_{A28}$, R = R$^{A28}$,
in L$_{A29}$, R = R$^{A29}$, in L$_{A30}$, R = R$^{A30}$,
in L$_{A31}$, R = R$^{A31}$, in L$_{A32}$, R = R$^{A32}$,
in L$_{A33}$, R = R$^{A33}$, in L$_{A34}$, R = R$^{A34}$,
in L$_{A35}$, R = R$^{A35}$, in L$_{A36}$, R = R$^{A36}$,
in L$_{A37}$, R = R$^{A37}$, in L$_{A38}$, R = R$^{A38}$,
in L$_{A39}$, R = R$^{A39}$, in L$_{A40}$, R = R$^{A40}$,
and in L$_{A41}$, R = R$^{A41}$;,
L$_{A42}$ through L$_{A82}$, each represented by the formula

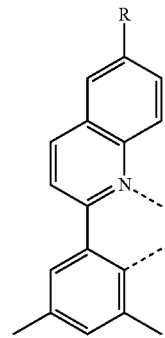

wherein
in L$_{A42}$, R = R$^{A1}$, in L$_{A43}$, R = R$^{A2}$,
in L$_{A44}$, R = R$^{A3}$, in L$_{A45}$, R = R$^{A4}$,
in L$_{A46}$, R = R$^{A5}$, in L$_{A47}$, R = R$^{A6}$,
in L$_{A48}$, R = R$^{A7}$, in L$_{A49}$, R = R$^{A8}$,
in L$_{A50}$, R = R$^{A9}$, in L$_{A51}$, R = R$^{A10}$,
in L$_{A52}$, R = R$^{A11}$, in L$_{A53}$, R = R$^{A12}$,
in L$_{A54}$, R = R$^{A13}$, in L$_{A55}$, R = R$^{A14}$,
in L$_{A56}$, R = R$^{A15}$, in L$_{A57}$, R = R$^{A16}$,
in L$_{A58}$, R = R$^{A17}$, in L$_{A59}$, R = R$^{A18}$,
in L$_{A60}$, R = R$^{A19}$, in L$_{A61}$, R = R$^{A20}$, in $L_{462}$, R = $R^{421}$, in $L_{463}$, R = $R^{422}$,
in $L_{464}$, R = $R^{423}$, in $L_{465}$, R = $R^{424}$,
in $L_{466}$, R = $R^{425}$, in $L_{467}$, R = $R^{426}$,
in $L_{468}$, R = $R^{427}$, in $L_{469}$, R = $R^{428}$,
in $L_{470}$, R = $R^{429}$, in $L_{471}$, R = $R^{430}$,
in $L_{472}$, R = $R^{431}$, in $L_{473}$, R = $R^{432}$,
in $L_{474}$, R = $R^{433}$, in $L_{475}$, R = $R^{434}$,
in $L_{476}$, R = $R^{435}$, in $L_{477}$, R = $R^{436}$,
in $L_{478}$, R = $R^{437}$, in $L_{479}$, R = $R^{438}$,
in $L_{480}$, R = $R^{439}$, in $L_{481}$, R = $R^{440}$,
and in $L_{482}$, R = $R^{441}$;;
$L_{483}$ through $L_{4123}$, each represented by the formula

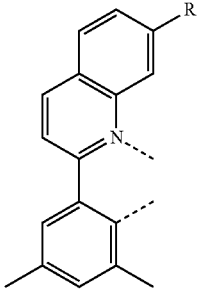

wherein
in $L_{483}$, R = $R^{41}$, in $L_{484}$, R = $R^{42}$,
in $L_{485}$, R = $R^{43}$, in $L_{486}$, R = $R^{44}$,
in $L_{487}$, R = $R^{45}$, in $L_{488}$, R = $R^{46}$,
in $L_{489}$, R = $R^{47}$, in $L_{490}$, R = $R^{48}$,
in $L_{491}$, R = $R^{49}$, in $L_{492}$, R = $R^{410}$,
in $L_{493}$, R = $R^{411}$, in $L_{494}$, R = $R^{412}$,
in $L_{495}$, R = $R^{413}$, in $L_{496}$, R = $R^{414}$,
in $L_{497}$, R = $R^{415}$, in $L_{498}$, R = $R^{416}$,
in $L_{499}$, R = $R^{417}$, in $L_{4100}$, R = $R^{418}$,
in $L_{4101}$, R = $R^{419}$, in $L_{4102}$, R = $R^{420}$,
in $L_{4103}$, R = $R^{421}$, in $L_{4104}$, R = $R^{422}$,
in $L_{4105}$, R = $R^{423}$, in $L_{4106}$, R = $R^{424}$,
in $L_{4107}$, R = $R^{425}$, in $L_{4108}$, R = $R^{426}$,
in $L_{4109}$, R = $R^{427}$, in $L_{4110}$, R = $R^{428}$,
in $L_{4111}$, R = $R^{429}$, in $L_{4112}$, R = $R^{430}$,
in $L_{4113}$, R = $R^{431}$, in $L_{4114}$, R = $R^{432}$,
in $L_{4115}$, R = $R^{433}$, in $L_{4116}$, R = $R^{434}$,
in $L_{4117}$, R = $R^{435}$, in $L_{4118}$, R = $R^{436}$,
in $L_{4119}$, R = $R^{437}$, in $L_{4120}$, R = $R^{438}$,
in $L_{4121}$, R = $R^{439}$, in $L_{4122}$, R = $R^{440}$,
and in $L_{4123}$, R = $R^{441}$;;
$L_{4124}$ through $L_{4164}$, each represented by the formula

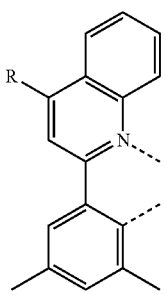

wherein
in $L_{4124}$, R = $R^{41}$, in $L_{4125}$, R = $R^{42}$,
in $L_{4126}$, R = $R^{43}$, in $L_{4127}$, R = $R^{44}$,
in $L_{4128}$, R = $R^{45}$, in $L_{4129}$, R = $R^{46}$,
in $L_{4130}$, R = $R^{47}$, in $L_{4131}$, R = $R^{48}$,
in $L_{4132}$, R = $R^{49}$, in $L_{4133}$, R = $R^{410}$,
in $L_{4134}$, R = $R^{411}$, in $L_{4135}$, R = $R^{412}$,
in $L_{4136}$, R = $R^{413}$, in $L_{4137}$, R = $R^{414}$,
in $L_{4138}$, R = $R^{415}$, in $L_{4139}$, R = $R^{416}$,
in $L_{4140}$, R = $R^{417}$, in $L_{4141}$, R = $R^{418}$,
in $L_{4142}$, R = $R^{419}$, in $L_{4143}$, R = $R^{420}$,
in $L_{4144}$, R = $R^{421}$, in $L_{4145}$, R = $R^{422}$,
in $L_{4146}$, R = $R^{423}$, in $L_{4147}$, R = $R^{424}$,
in $L_{4148}$, R = $R^{425}$, in $L_{4149}$, R = $R^{426}$,
in $L_{4150}$, R = $R^{427}$, in $L_{4151}$, R = $R^{428}$,
in $L_{4152}$, R = $R^{429}$, in $L_{4153}$, R = $R^{430}$,
in $L_{4154}$, R = $R^{431}$, in $L_{4155}$, R = $R^{432}$,
in $L_{4156}$, R = $R^{433}$, in $L_{4157}$, R = $R^{434}$,
in $L_{4158}$, R = $R^{435}$, in $L_{4159}$, R = $R^{436}$,
in $L_{4160}$, R = $R^{437}$, in $L_{4161}$, R = $R^{438}$,
in $L_{4162}$, R = $R^{439}$, in $L_{4163}$, R = $R^{440}$,
and in $L_{4164}$, R = $R^{441}$;;
$L_{4165}$ through $L_{4205}$, each represented by the formula

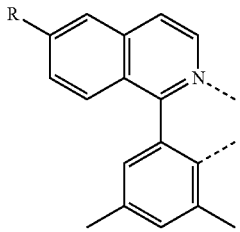

wherein
in $L_{4165}$, R = $R^{41}$, in $L_{4166}$, R = $R^{42}$,
in $L_{4167}$, R = $R^{43}$, in $L_{4168}$, R = $R^{44}$,
in $L_{4169}$, R = $R^{45}$, in $L_{4170}$, R = $R^{46}$,
in $L_{4171}$, R = $R^{47}$, in $L_{4172}$, R = $R^{48}$,
in $L_{4173}$, R = $R^{49}$, in $L_{4174}$, R = $R^{410}$,
in $L_{4175}$, R = $R^{411}$, in $L_{4176}$, R = $R^{412}$,
in $L_{4177}$, R = $R^{413}$, in $L_{4178}$, R = $R^{414}$,
in $L_{4179}$, R = $R^{415}$, in $L_{4180}$, R = $R^{416}$,
in $L_{4181}$, R = $R^{417}$, in $L_{4182}$, R = $R^{418}$,
in $L_{4183}$, R = $R^{419}$, in $L_{4184}$, R = $R^{420}$,
in $L_{4185}$, R = $R^{421}$, in $L_{4186}$, R = $R^{422}$,
in $L_{4187}$, R = $R^{423}$, in $L_{4188}$, R = $R^{424}$,
in $L_{4189}$, R = $R^{425}$, in $L_{4190}$, R = $R^{426}$,
in $L_{4191}$, R = $R^{427}$, in $L_{4192}$, R = $R^{428}$,
in $L_{4193}$, R = $R^{429}$, in $L_{4194}$, R = $R^{430}$,
in $L_{4195}$, R = $R^{431}$, in $L_{4196}$, R = $R^{432}$,
in $L_{4197}$, R = $R^{433}$, in $L_{4198}$, R = $R^{434}$,
in $L_{4199}$, R = $R^{435}$, in $L_{4200}$, R = $R^{436}$,
in $L_{4201}$, R = $R^{437}$, in $L_{4202}$, R = $R^{438}$,
in $L_{4203}$, R = $R^{439}$, in $L_{4204}$, R = $R^{440}$,
and in $L_{4205}$, R = $R^{441}$;;
$L_{4206}$ through $L_{4246}$, each represented by the formula

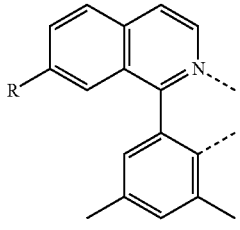

wherein
in $L_{4206}$, R = $R^{41}$, in $L_{4207}$, R = $R^{42}$,
in $L_{4208}$, R = $R^{43}$, in $L_{4209}$, R = $R^{44}$,
in $L_{4210}$, R = $R^{45}$, in $L_{4211}$, R = $R^{46}$,
in $L_{4212}$, R = $R^{47}$, in $L_{4213}$, R = $R^{48}$,
in $L_{4214}$, R = $R^{49}$, in $L_{4215}$, R = $R^{410}$,
in $L_{4216}$, R = $R^{411}$, in $L_{4217}$, R = $R^{412}$,
in $L_{4218}$, R = $R^{413}$, in $L_{4219}$, R = $R^{414}$,
in $L_{4220}$, R = $R^{415}$, in $L_{4221}$, R = $R^{416}$,
in $L_{4222}$, R = $R^{417}$, in $L_{4223}$, R = $R^{418}$,
in $L_{4224}$, R = $R^{419}$, in $L_{4225}$, R = $R^{420}$,
in $L_{4226}$, R = $R^{421}$, in $L_{4227}$, R = $R^{422}$,
in $L_{4228}$, R = $R^{423}$, in $L_{4229}$, R = $R^{424}$,
in $L_{4230}$, R = $R^{425}$, in $L_{4231}$, R = $R^{426}$,
in $L_{4232}$, R = $R^{427}$, in $L_{4233}$, R = $R^{428}$,
in $L_{4234}$, R = $R^{429}$, in $L_{4235}$, R = $R^{430}$,
in $L_{4236}$, R = $R^{431}$, in $L_{4237}$, R = $R^{432}$, in L<sub>A238</sub>, R = R<sup>433</sup>, in L<sub>A239</sub>, R = R<sup>434</sup>,
in L<sub>A240</sub>, R = R<sup>435</sup>, in L<sub>A241</sub>, R = R<sup>436</sup>,
in L<sub>A242</sub>, R = R<sup>437</sup>, in L<sub>A243</sub>, R = R<sup>438</sup>,
in L<sub>A244</sub>, R = R<sup>439</sup>, in L<sub>A245</sub>, R = R<sup>440</sup>,
and in L<sub>A246</sub>, R = R<sup>441</sup>;;

L<sub>A247</sub> through L<sub>A287</sub>, each
represented by the formula

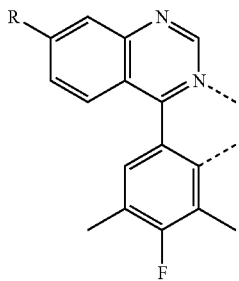

wherein
in L<sub>A247</sub>, R = R<sup>41</sup>, in L<sub>A248</sub>, R = R<sup>42</sup>,
in L<sub>A249</sub>, R = R<sup>43</sup>, in L<sub>A250</sub>, R = R<sup>44</sup>,
in L<sub>A251</sub>, R = R<sup>45</sup>, in L<sub>A252</sub>, R = R<sup>46</sup>,
in L<sub>A253</sub>, R = R<sup>47</sup>, in L<sub>A254</sub>, R = R<sup>48</sup>,
in L<sub>A255</sub>, R = R<sup>49</sup>, in L<sub>A256</sub>, R = R<sup>410</sup>,
in L<sub>A257</sub>, R = R<sup>411</sup>, in L<sub>A258</sub>, R = R<sup>412</sup>,
in L<sub>A259</sub>, R = R<sup>413</sup>, in L<sub>A260</sub>, R = R<sup>414</sup>,
in L<sub>A261</sub>, R = R<sup>415</sup>, in L<sub>A262</sub>, R = R<sup>416</sup>,
in L<sub>A263</sub>, R = R<sup>417</sup>, in L<sub>A264</sub>, R = R<sup>418</sup>,
in L<sub>A265</sub>, R = R<sup>419</sup>, in L<sub>A266</sub>, R = R<sup>420</sup>,
in L<sub>A267</sub>, R = R<sup>421</sup>, in L<sub>A268</sub>, R = R<sup>422</sup>,
in L<sub>A269</sub>, R = R<sup>423</sup>, in L<sub>A270</sub>, R = R<sup>424</sup>,
in L<sub>A271</sub>, R = R<sup>425</sup>, in L<sub>A272</sub>, R = R<sup>426</sup>,
in L<sub>A273</sub>, R = R<sup>427</sup>, in L<sub>A274</sub>, R = R<sup>428</sup>,
in L<sub>A275</sub>, R = R<sup>429</sup>, in L<sub>A276</sub>, R = R<sup>430</sup>,
in L<sub>A277</sub>, R = R<sup>431</sup>, in L<sub>A278</sub>, R = R<sup>432</sup>,
in L<sub>A279</sub>, R = R<sup>433</sup>, in L<sub>A280</sub>, R = R<sup>434</sup>,
in L<sub>A281</sub>, R = R<sup>435</sup>, in L<sub>A282</sub>, R = R<sup>436</sup>,
in L<sub>A283</sub>, R = R<sup>437</sup>, in L<sub>A284</sub>, R = R<sup>438</sup>,
in L<sub>A285</sub>, R = R<sup>439</sup>, in L<sub>A286</sub>, R = R<sup>440</sup>,
and in L<sub>A287</sub>, R = R<sup>441</sup>;;

L<sub>A288</sub> through L<sub>A328</sub>, each
represented by the formula

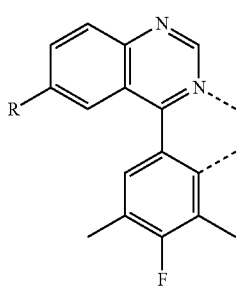

wherein
in L<sub>A288</sub>, R = R<sup>41</sup>, in L<sub>A289</sub>, R = R<sup>42</sup>,
in L<sub>A290</sub>, R = R<sup>43</sup>, in L<sub>A291</sub>, R = R<sup>44</sup>,
in L<sub>A292</sub>, R = R<sup>45</sup>, in L<sub>A293</sub>, R = R<sup>46</sup>,
in L<sub>A294</sub>, R = R<sup>47</sup>, in L<sub>A295</sub>, R = R<sup>48</sup>,
in L<sub>A296</sub>, R = R<sup>49</sup>, in L<sub>A297</sub>, R = R<sup>410</sup>,
in L<sub>A298</sub>, R = R<sup>411</sup>, in L<sub>A299</sub>, R = R<sup>412</sup>,
in L<sub>A300</sub>, R = R<sup>413</sup>, in L<sub>A301</sub>, R = R<sup>414</sup>,
in L<sub>A302</sub>, R = R<sup>415</sup>, in L<sub>A303</sub>, R = R<sup>416</sup>,
in L<sub>A304</sub>, R = R<sup>417</sup>, in L<sub>A305</sub>, R = R<sup>418</sup>,
in L<sub>A306</sub>, R = R<sup>419</sup>, in L<sub>A307</sub>, R = R<sup>420</sup>,
in L<sub>A308</sub>, R = R<sup>421</sup>, in L<sub>A309</sub>, R = R<sup>422</sup>,
in L<sub>A310</sub>, R = R<sup>423</sup>, in L<sub>A311</sub>, R = R<sup>424</sup>,
in L<sub>A312</sub>, R = R<sup>425</sup>, in L<sub>A313</sub>, R = R<sup>426</sup>,
in L<sub>A314</sub>, R = R<sup>427</sup>, in L<sub>A315</sub>, R = R<sup>428</sup>,
in L<sub>A316</sub>, R = R<sup>429</sup>, in L<sub>A317</sub>, R = R<sup>430</sup>,
in L<sub>A318</sub>, R = R<sup>431</sup>, in L<sub>A319</sub>, R = R<sup>432</sup>,
in L<sub>A320</sub>, R = R<sup>433</sup>, in L<sub>A321</sub>, R = R<sup>434</sup>,
in L<sub>A322</sub>, R = R<sup>435</sup>, in L<sub>A323</sub>, R = R<sup>436</sup>,
in L<sub>A324</sub>, R = R<sup>437</sup>, in L<sub>A325</sub>, R = R<sup>438</sup>,
in L<sub>A326</sub>, R = R<sup>439</sup>, in L<sub>A327</sub>, R = R<sup>440</sup>,
and in L<sub>A328</sub>, R = R<sup>441</sup>;;

L<sub>A329</sub> through L<sub>A369</sub>, each
represented by the formula

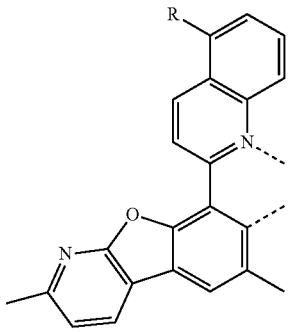

wherein
in L<sub>A329</sub>, R = R<sup>41</sup>, in L<sub>A330</sub>, R = R<sup>42</sup>,
in L<sub>A331</sub>, R = R<sup>43</sup>, in L<sub>A332</sub>, R = R<sup>44</sup>,
in L<sub>A333</sub>, R = R<sup>45</sup>, in L<sub>A334</sub>, R = R<sup>46</sup>,
in L<sub>A335</sub>, R = R<sup>47</sup>, in L<sub>A336</sub>, R = R<sup>48</sup>,
in L<sub>A337</sub>, R = R<sup>49</sup>, in L<sub>A338</sub>, R = R<sup>410</sup>,
in L<sub>A339</sub>, R = R<sup>411</sup>, in L<sub>A340</sub>, R = R<sup>412</sup>,
in L<sub>A341</sub>, R = R<sup>413</sup>, in L<sub>A342</sub>, R = R<sup>414</sup>,
in L<sub>A343</sub>, R = R<sup>415</sup>, in L<sub>A344</sub>, R = R<sup>416</sup>,
in L<sub>A345</sub>, R = R<sup>417</sup>, in L<sub>A346</sub>, R = R<sup>418</sup>,
in L<sub>A347</sub>, R = R<sup>419</sup>, in L<sub>A348</sub>, R = R<sup>420</sup>,
in L<sub>A349</sub>, R = R<sup>421</sup>, in L<sub>A350</sub>, R = R<sup>422</sup>,
in L<sub>A351</sub>, R = R<sup>423</sup>, in L<sub>A352</sub>, R = R<sup>424</sup>,
in L<sub>A353</sub>, R = R<sup>425</sup>, in L<sub>A354</sub>, R = R<sup>426</sup>,
in L<sub>A355</sub>, R = R<sup>427</sup>, in L<sub>A356</sub>, R = R<sup>428</sup>,
in L<sub>A357</sub>, R = R<sup>429</sup>, in L<sub>A358</sub>, R = R<sup>430</sup>,
in L<sub>A359</sub>, R = R<sup>431</sup>, in L<sub>A360</sub>, R = R<sup>432</sup>,
in L<sub>A361</sub>, R = R<sup>433</sup>, in L<sub>A362</sub>, R = R<sup>434</sup>,
in L<sub>A363</sub>, R = R<sup>435</sup>, in L<sub>A364</sub>, R = R<sup>436</sup>,
in L<sub>A365</sub>, R = R<sup>437</sup>, in L<sub>A366</sub>, R = R<sup>438</sup>,
in L<sub>A367</sub>, R = R<sup>439</sup>, in L<sub>A368</sub>, R = R<sup>440</sup>,
and in L<sub>A369</sub>, R = R<sup>441</sup>;;

L<sub>A370</sub> through L<sub>A410</sub>, each
represented by the formula

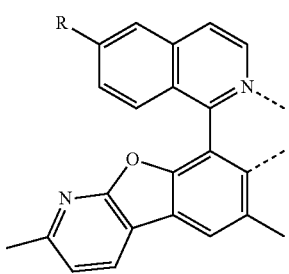

wherein
in L<sub>A370</sub>, R = R<sup>41</sup>, in L<sub>A371</sub>, R = R<sup>42</sup>,
in L<sub>A372</sub>, R = R<sup>43</sup>, in L<sub>A373</sub>, R = R<sup>44</sup>,
in L<sub>A374</sub>, R = R<sup>45</sup>, in L<sub>A375</sub>, R = R<sup>46</sup>,
in L<sub>A376</sub>, R = R<sup>47</sup>, in L<sub>A377</sub>, R = R<sup>48</sup>,
in L<sub>A378</sub>, R = R<sup>49</sup>, in L<sub>A379</sub>, R = R<sup>410</sup>,
in L<sub>A380</sub>, R = R<sup>411</sup>, in L<sub>A381</sub>, R = R<sup>412</sup>,
in L<sub>A382</sub>, R = R<sup>413</sup>, in L<sub>A383</sub>, R = R<sup>414</sup>,
in L<sub>A384</sub>, R = R<sup>415</sup>, in L<sub>A385</sub>, R = R<sup>416</sup>,
in L<sub>A386</sub>, R = R<sup>417</sup>, in L<sub>A387</sub>, R = R<sup>418</sup>,
in L<sub>A388</sub>, R = R<sup>419</sup>, in L<sub>A389</sub>, R = R<sup>420</sup>,
in L<sub>A390</sub>, R = R<sup>421</sup>, in L<sub>A391</sub>, R = R<sup>422</sup>,
in L<sub>A392</sub>, R = R<sup>423</sup>, in L<sub>A393</sub>, R = R<sup>424</sup>,
in L<sub>A394</sub>, R = R<sup>425</sup>, in L<sub>A395</sub>, R = R<sup>426</sup>,
in L<sub>A396</sub>, R = R<sup>427</sup>, in L<sub>A397</sub>, R = R<sup>428</sup>,
in L<sub>A398</sub>, R = R<sup>429</sup>, in L<sub>A399</sub>, R = R<sup>430</sup>,
in L<sub>A400</sub>, R = R<sup>431</sup>, in L<sub>A401</sub>, R = R<sup>432</sup>,
in L<sub>A402</sub>, R = R<sup>433</sup>, in L<sub>A403</sub>, R = R<sup>434</sup>,
in L<sub>A404</sub>, R = R<sup>435</sup>, in L<sub>A405</sub>, R = R<sup>436</sup>, in L$_{A406}$, R = R$^{A37}$, in L$_{A407}$, R = R$^{A38}$,
in L$_{A408}$, R = R$^{A39}$, in L$_{A409}$, R = R$^{A40}$,
and in L$_{A410}$, R = R$^{A41}$;
and
L$_{A411}$ through L$_{A451}$, each
represented by the formula

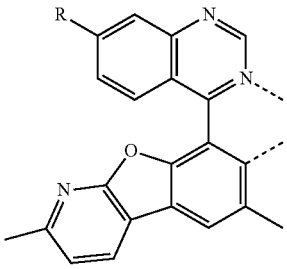

wherein
in L$_{A411}$, R = R$^{A1}$, in L$_{A412}$, R = R$^{A2}$,
in L$_{A413}$, R = R$^{A3}$, in L$_{A414}$, R = R$^{A4}$,
in L$_{A415}$, R = R$^{A5}$, in L$_{A416}$, R = R$^{A6}$,
in L$_{A417}$, R = R$^{A7}$, in L$_{A418}$, R = R$^{A8}$,
in L$_{A419}$, R = R$^{A9}$, in L$_{A420}$, R = R$^{A10}$,
in L$_{A421}$, R = R$^{A11}$, in L$_{A422}$, R = R$^{A12}$,
in L$_{A423}$, R = R$^{A13}$, in L$_{A424}$, R = R$^{A14}$,
in L$_{A425}$, R = R$^{A15}$, in L$_{A426}$, R = R$^{A16}$,
in L$_{A427}$, R = R$^{A17}$, in L$_{A428}$, R = R$^{A18}$,
in L$_{A429}$, R = R$^{A19}$, in L$_{A430}$, R = R$^{A20}$,
in L$_{A431}$, R = R$^{A21}$, in L$_{A432}$, R = R$^{A22}$,
in L$_{A433}$, R = R$^{A23}$, in L$_{A434}$, R = R$^{A24}$,
in L$_{A435}$, R = R$^{A25}$, in L$_{A436}$, R = R$^{A26}$,
in L$_{A437}$, R = R$^{A27}$, in L$_{A438}$, R = R$^{A28}$,
in L$_{A439}$, R = R$^{A29}$, in L$_{A440}$, R = R$^{A30}$,
in L$_{A441}$, R = R$^{A31}$, in L$_{A442}$, R = R$^{A32}$,
in L$_{A443}$, R = R$^{A33}$, in L$_{A444}$, R = R$^{A34}$,
in L$_{A445}$, R = R$^{A35}$, in L$_{A446}$, R = R$^{A36}$,
in L$_{A447}$, R = R$^{A37}$, in L$_{A448}$, R = R$^{A38}$,
in L$_{A449}$, R = R$^{A39}$, in L$_{A450}$, R = R$^{A40}$,
and in L$_{A451}$, R = R$^{A41}$;, wherein, R$^{A1}$ through R$^{A41}$ have the formulas:

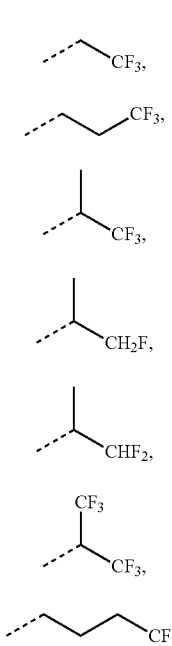

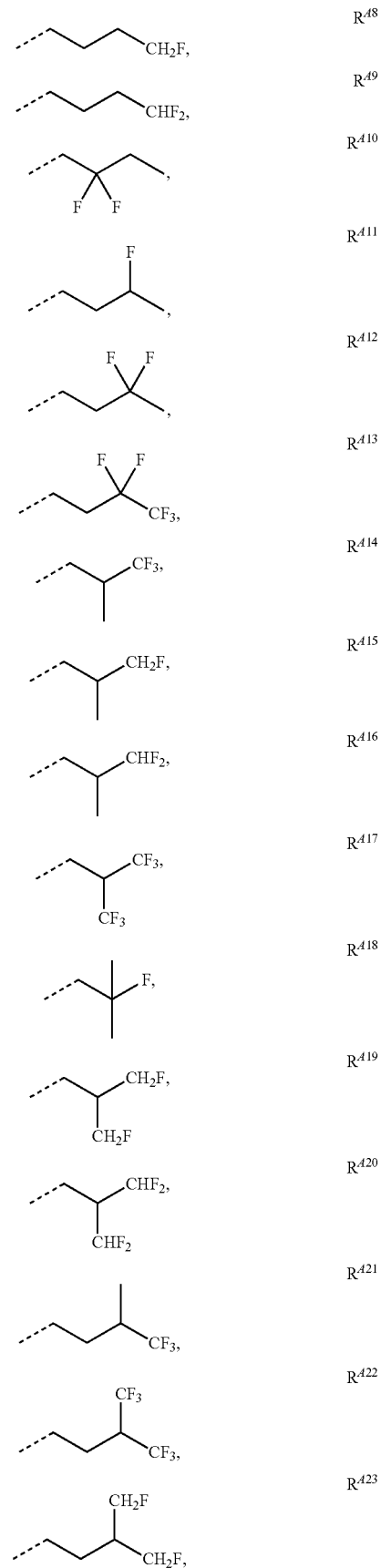

-continued
R^{A24} 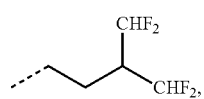
R^{A25} 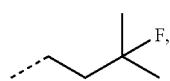
R^{A26} 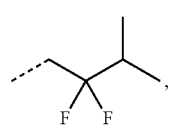
R^{A27} 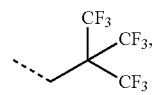
R^{A28} 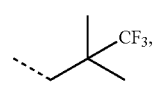
R^{A429} 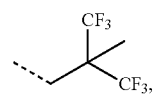
R^{A430} 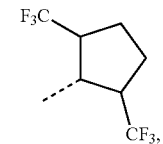
R^{A431} 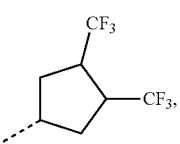
R^{A432} 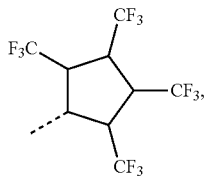
R^{A433} 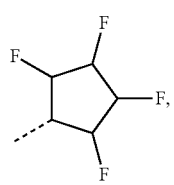
-continued
R^{A434} 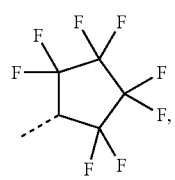
R^{A435} 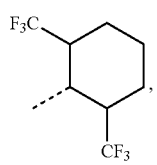
R^{A436} 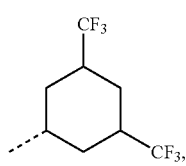
R^{A437} 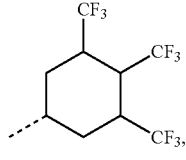
R^{A438} 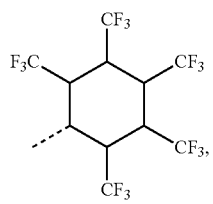
R^{A439} 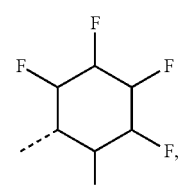
R^{A440} 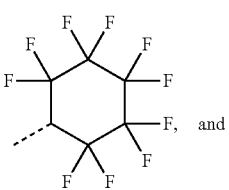
R^{A441} 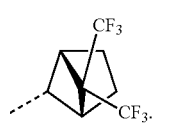
14. The composition of claim 1, wherein the first compound has the formula of $Ir(L^1)_2(L^2)$, wherein $L^1$ is selected from the group consisting of $L_{A1}$ through $L_{A41}$, each represented by the formula

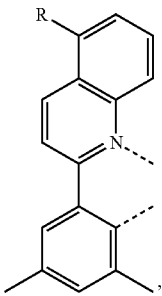

wherein
in $L_{A1}$, R = $R^{A1}$, in $L_{A2}$, R = $R^{A2}$,
in $L_{A3}$, R = $R^{A3}$, in $L_{A4}$, R = $R^{A4}$,
in $L_{A5}$, R = $R^{A5}$, in $L_{A6}$, R = $R^{A6}$,
in $L_{A7}$, R = $R^{A7}$, in $L_{A8}$, R = $R^{A8}$,
in $L_{A9}$, R = $R^{A9}$, in $L_{A10}$, R = $R^{A10}$,
in $L_{A11}$, R = $R^{A11}$, in $L_{A12}$, R = $R^{A12}$,
in $L_{A13}$, R = $R^{A13}$, in $L_{A14}$, R = $R^{A14}$,
in $L_{A15}$, R = $R^{A15}$, in $L_{A16}$, R = $R^{A16}$,
in $L_{A17}$, R = $R^{A17}$, in $L_{A18}$, R = $R^{A18}$,
in $L_{A19}$, R = $R^{A19}$, in $L_{A20}$, R = $R^{A20}$,
in $L_{A21}$, R = $R^{A21}$, in $L_{A22}$, R = $R^{A22}$,
in $L_{A23}$, R = $R^{A23}$, in $L_{A24}$, R = $R^{A24}$,
in $L_{A25}$, R = $R^{A25}$, in $L_{A26}$, R = $R^{A26}$,
in $L_{A27}$, R = $R^{A27}$, in $L_{A28}$, R = $R^{A28}$,
in $L_{A29}$, R = $R^{A29}$, in $L_{A30}$, R = $R^{A30}$,
in $L_{A31}$, R = $R^{A31}$, in $L_{A32}$, R = $R^{A32}$,
in $L_{A33}$, R = $R^{A33}$, in $L_{A34}$, R = $R^{A34}$,
in $L_{A35}$, R = $R^{A35}$, in $L_{A36}$, R = $R^{A36}$,
in $L_{A37}$, R = $R^{A37}$, in $L_{A38}$, R = $R^{A38}$,
in $L_{A39}$, R = $R^{A39}$, in $L_{A40}$, R = $R^{A40}$,
and in $L_{A41}$, R = $R^{A41}$;, $L_{A42}$ through $L_{A82}$, each represented by the formula

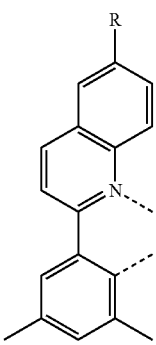

wherein
in $L_{A42}$, R = $R^{A1}$, in $L_{A43}$, R = $R^{A2}$,
in $L_{A44}$, R = $R^{A3}$, in $L_{A45}$, R = $R^{A4}$,
in $L_{A46}$, R = $R^{A5}$, in $L_{A47}$, R = $R^{A6}$,
in $L_{A48}$, R = $R^{A7}$, in $L_{A49}$, R = $R^{A8}$,
in $L_{A50}$, R = $R^{A9}$, in $L_{A51}$, R = $R^{A10}$,
in $L_{A52}$, R = $R^{A11}$, in $L_{A53}$, R = $R^{A12}$,
in $L_{A54}$, R = $R^{A13}$, in $L_{A55}$, R = $R^{A14}$,
in $L_{A56}$, R = $R^{A15}$, in $L_{A57}$, R = $R^{A16}$,
in $L_{A58}$, R = $R^{A17}$, in $L_{A59}$, R = $R^{A18}$,
in $L_{A60}$, R = $R^{A19}$, in $L_{A61}$, R = $R^{A20}$,
in $L_{A62}$, R = $R^{A21}$, in $L_{A63}$, R = $R^{A22}$,
in $L_{A64}$, R = $R^{A23}$, in $L_{A65}$, R = $R^{A24}$,
in $L_{A66}$, R = $R^{A25}$, in $L_{A67}$, R = $R^{A26}$,
in $L_{A68}$, R = $R^{A27}$, in $L_{A69}$, R = $R^{A28}$,
in $L_{A70}$, R = $R^{A29}$, in $L_{A71}$, R = $R^{A30}$,
in $L_{A72}$, R = $R^{A31}$, in $L_{A73}$, R = $R^{A32}$,
in $L_{A74}$, R = $R^{A33}$, in $L_{A75}$, R = $R^{A34}$,
in $L_{A76}$, R = $R^{A35}$, in $L_{A77}$, R = $R^{A36}$,
in $L_{A78}$, R = $R^{A37}$, in $L_{A79}$, R = $R^{A38}$,
in $L_{A80}$, R = $R^{A39}$, in $L_{A81}$, R = $R^{A40}$,
and in $L_{A82}$, R = $R^{A41}$;, $L_{A83}$ through $L_{A123}$, each represented by the formula

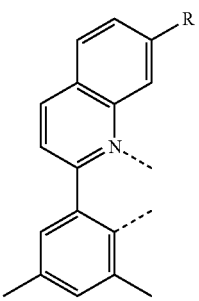

wherein
in $L_{A83}$, R = $R^{A1}$, in $L_{A84}$, R = $R^{A2}$,
in $L_{A85}$, R = $R^{A3}$, in $L_{A86}$, R = $R^{A4}$,
in $L_{A87}$, R = $R^{A5}$, in $L_{A88}$, R = $R^{A6}$,
in $L_{A89}$, R = $R^{A7}$, in $L_{A90}$, R = $R^{A8}$,
In $L_{A91}$, R = $R^{A9}$, in $L_{A92}$, R = $R^{A10}$,
in $L_{A93}$, R = $R^{A11}$, in $L_{A94}$, R = $R^{A12}$,
in $L_{A95}$, R = $R^{A13}$, in $L_{A96}$, R = $R^{A14}$,
in $L_{A97}$, R = $R^{A15}$, in $L_{A98}$, R = $R^{A16}$,
in $L_{A99}$, R = $R^{A17}$, in $L_{A100}$, R = $R^{A18}$,
in $L_{A101}$, R = $R^{A19}$, in $L_{A102}$, R = $R^{A20}$,
in $L_{A103}$, R = $R^{A21}$, in $L_{A104}$, R = $R^{A22}$,
in $L_{A105}$, R = $R^{A23}$, in $L_{A106}$, R = $R^{A24}$,
in $L_{A107}$, R = $R^{A25}$, in $L_{A108}$, R = $R^{A26}$,
in $L_{A109}$, R = $R^{A27}$, in $L_{A110}$, R = $R^{A28}$,
in $L_{A111}$, R = $R^{A29}$, in $L_{A112}$, R = $R^{A30}$,
in $L_{A113}$, R = $R^{A31}$, in $L_{A114}$, R = $R^{A32}$,
in $L_{A115}$, R = $R^{A33}$, in $L_{A116}$, R = $R^{A34}$,
in $L_{A117}$, R = $R^{A35}$, in $L_{A118}$, R = $R^{A36}$,
in $L_{A119}$, R = $R^{A37}$, in $L_{A120}$, R = $R^{A38}$,
in $L_{A121}$, R = $R^{A39}$, in $L_{A122}$, R = $R^{A40}$,
and in $LA_{123}$, R = $R^{A41}$;, $LA_{124}$ through $L_{A164}$, each represented by the formula

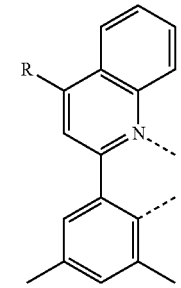

wherein
in $L_{A124}$, R = $R^{A1}$, in $L_{A125}$, R = $R^{A2}$,
in $L_{A126}$, R = $R^{A3}$, in $L_{A127}$, R = $R^{A4}$,
in $L_{A128}$, R = $R^{A5}$, in $L_{A129}$, R = $R^{A6}$,
in $L_{A130}$, R = $R^{A7}$, in $L_{A131}$, R = $R^{A8}$,
In $L_{A132}$, R = $R^{A9}$, in $L_{A133}$, R = $R^{A10}$,
in $L_{A134}$, R = $R^{A11}$, in $L_{A135}$, R = $R^{A12}$,
in $L_{A136}$, R = $R^{A13}$, in $L_{A137}$, R = $R^{A14}$,
in $L_{A138}$, R = $R^{A15}$, in $L_{A139}$, R = $R^{A16}$,
in $L_{A140}$, R = $R^{A17}$, in $L_{A141}$, R = $R^{A18}$,
in $L_{A142}$, R = $R^{A19}$, in $L_{A143}$, R = $R^{A20}$,
in $L_{A144}$, R = $R^{A21}$, in $L_{A145}$, R = $R^{A22}$,
in $L_{A146}$, R = $R^{A23}$, in $L_{A147}$, R = $R^{A24}$,
in $L_{A148}$, R = $R^{A25}$, in $L_{A149}$, R = $R^{A26}$, -continued in $L_{A150}$, R = $R^{427}$, in $L_{A151}$, R = $R^{428}$,
in $L_{A152}$, R = $R^{429}$, in $L_{A153}$, R = $R^{430}$,
in $L_{A154}$, R = $R^{431}$, in $L_{A155}$, R = $R^{432}$,
in $L_{A156}$, R = $R^{433}$, in $L_{A157}$, R = $R^{434}$,
in $L_{A158}$, R = $R^{435}$, in $L_{A159}$, R = $R^{436}$,
in $L_{A160}$, R = $R^{437}$, in $L_{A161}$, R = $R^{438}$,
in $L_{A162}$, R = $R^{439}$, in $L_{A163}$, R = $R^{440}$,
and in $L_{A164}$, R = $R^{441}$;

$L_{A165}$ through $L_{A205}$, each represented by the formula

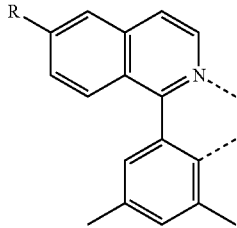

wherein
in $L_{A165}$, R = $R^{41}$, in $L_{A166}$, R = $R^{42}$,
in $L_{A167}$, R = $R^{43}$, in $L_{A168}$, R = $R^{44}$,
in $L_{A169}$, R = $R^{45}$, in $L_{A170}$, R = $R^{46}$,
in $L_{A171}$, R = $R^{47}$, in $L_{A172}$, R = $R^{48}$,
In $L_{A173}$, R = $R^{49}$, in $L_{A174}$, R = $R^{410}$,
in $L_{A175}$, R = $R^{411}$, in $L_{A176}$, R = $R^{412}$,
in $L_{A177}$, R = $R^{413}$, in $L_{A178}$, R = $R^{414}$,
in $L_{A179}$, R = $R^{415}$, in $L_{A180}$, R = $R^{416}$,
in $L_{A181}$, R = $R^{417}$, in $L_{A182}$, R = $R^{418}$,
in $L_{A183}$, R = $R^{419}$, in $L_{A184}$, R = $R^{420}$,
in $L_{A185}$, R = $R^{421}$, in $L_{A186}$, R = $R^{422}$,
in $L_{A187}$, R = $R^{423}$, in $L_{A188}$, R = $R^{424}$,
in $L_{A189}$, R = $R^{425}$, in $L_{A190}$, R = $R^{426}$,
in $L_{A191}$, R = $R^{427}$, in $L_{A192}$, R = $R^{428}$,
in $L_{A193}$, R = $R^{429}$, in $L_{A194}$, R = $R^{430}$,
in $L_{A195}$, R = $R^{431}$, in $L_{A196}$, R = $R^{432}$,
in $L_{A197}$, R = $R^{433}$, in $L_{A198}$, R = $R^{434}$,
in $L_{A199}$, R = $R^{435}$, in $L_{A200}$, R = $R^{436}$,
in $L_{A201}$, R = $R^{437}$, in $L_{A202}$, R = $R^{438}$,
in $L_{A203}$, R = $R^{439}$, in $L_{A204}$, R = $R^{440}$,
and in $L_{A205}$, R = $R^{441}$;

$L_{A206}$ through $L_{A246}$, each represented by the formula

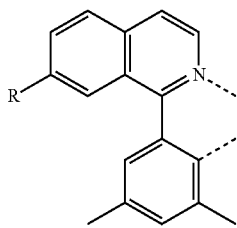

wherein
in $L_{A206}$, R = $R^{41}$, in $L_{A207}$, R = $R^{42}$,
in $L_{A208}$, R = $R^{43}$, in $L_{A209}$, R = $R^{44}$,
in $L_{A210}$, R = $R^{45}$, in $L_{A211}$, R = $R^{46}$,
in $L_{A212}$, R = $R^{47}$, in $L_{A213}$, R = $R^{48}$,
In $L_{A214}$, R = $R^{49}$, in $L_{A215}$, R = $R^{410}$,
in $L_{A216}$, R = $R^{411}$, in $L_{A217}$, R = $R^{412}$,
in $L_{A218}$, R = $R^{413}$, in $L_{A219}$, R = $R^{414}$,
in $L_{A220}$, R = $R^{415}$, in $L_{A221}$, R = $R^{416}$,
in $L_{A222}$, R = $R^{417}$, in $L_{A223}$, R = $R^{418}$,
in $L_{A224}$, R = $R^{419}$, in $L_{A225}$, R = $R^{420}$,
in $L_{A226}$, R = $R^{421}$, in $L_{A227}$, R = $R^{422}$,
in $L_{A228}$, R = $R^{423}$, in $L_{A229}$, R = $R^{424}$,
in $L_{A230}$, R = $R^{425}$, in $L_{A231}$, R = $R^{426}$,
in $L_{A232}$, R = $R^{427}$, in $L_{A233}$, R = $R^{428}$, in $L_{A234}$, R = $R^{429}$, in $L_{A235}$, R = $R^{430}$,
in $L_{A236}$, R = $R^{431}$, in $L_{A237}$, R = $R^{432}$,
in $L_{A238}$, R = $R^{433}$, in $L_{A239}$, R = $R^{434}$,
in $L_{A240}$, R = $R^{435}$, in $L_{A241}$, R = $R^{436}$,
in $L_{A242}$, R = $R^{437}$, in $L_{A243}$, R = $R^{438}$,
in $L_{A244}$, R = $R^{439}$, in $L_{A245}$, R = $R^{440}$,
and in $L_{A246}$, R = $R^{441}$;

$L_{A247}$ through $L_{A287}$, each represented by the formula

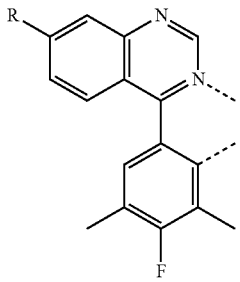

wherein
in $L_{A247}$, R = $R^{41}$, in $L_{A248}$, R = $R^{42}$,
in $L_{A249}$, R = $R^{43}$, in $L_{A250}$, R = $R^{44}$,
in $L_{A251}$, R = $R^{45}$, in $L_{A252}$, R = $R^{46}$,
in $L_{A253}$, R = $R^{47}$, in $L_{A254}$, R = $R^{48}$,
In $L_{A255}$, R = $R^{49}$, in $L_{A256}$, R = $R^{410}$,
in $L_{A257}$, R = $R^{411}$, in $L_{A258}$, R = $R^{412}$,
in $L_{A259}$, R = $R^{413}$, in $L_{A260}$, R = $R^{414}$,
in $L_{A261}$, R = $R^{415}$, in $L_{A262}$, R = $R^{416}$,
in $L_{A263}$, R = $R^{417}$, in $L_{A264}$, R = $R^{418}$,
in $L_{A265}$, R = $R^{419}$, in $L_{A266}$, R = $R^{420}$,
in $L_{A267}$, R = $R^{421}$, in $L_{A268}$, R = $R^{422}$,
in $L_{A269}$, R = $R^{423}$, in $L_{A270}$, R = $R^{424}$,
in $L_{A271}$, R = $R^{425}$, in $L_{A272}$, R = $R^{426}$,
in $L_{A273}$, R = $R^{427}$, in $L_{A274}$, R = $R^{428}$,
in $L_{A275}$, R = $R^{429}$, in $L_{A276}$, R = $R^{430}$,
in $L_{A277}$, R = $R^{431}$, in $L_{A278}$, R = $R^{432}$,
in $L_{A279}$, R = $R^{433}$, in $L_{A280}$, R = $R^{434}$,
in $L_{A281}$, R = $R^{435}$, in $L_{A282}$, R = $R^{436}$,
in $L_{A283}$, R = $R^{437}$, in $L_{A284}$, R = $R^{438}$,
in $L_{A285}$, R = $R^{439}$, in $L_{A286}$, R = $R^{440}$,
and in $L_{A287}$, R = $R^{441}$;

$L_{A288}$ through $L_{A328}$, each represented by the formula

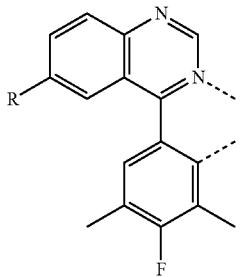

wherein
in $L_{A288}$, R = $R^{41}$, in $L_{A289}$, R = $R^{42}$,
in $L_{A290}$, R = $R^{43}$, in $L_{A291}$, R = $R^{44}$,
in $L_{A292}$, R = $R^{45}$, in $L_{A293}$, R = $R^{46}$,
in $L_{A294}$, R = $R^{47}$, in $L_{A295}$, R = $R^{48}$,
In $L_{A296}$, R = $R^{49}$, in $L_{A297}$, R = $R^{410}$,
in $L_{A298}$, R = $R^{411}$, in $L_{A299}$, R = $R^{412}$,
in $L_{A300}$, R = $R^{413}$, in $L_{A301}$, R = $R^{414}$,
in $L_{A302}$, R = $R^{415}$, in $L_{A303}$, R = $R^{416}$,
in $L_{A304}$, R = $R^{417}$, in $L_{A305}$, R = $R^{418}$,
in $L_{A306}$, R = $R^{419}$, in $L_{A307}$, R = $R^{420}$,
in $L_{A308}$, R = $R^{421}$, in $L_{A309}$, R = $R^{422}$,
in $L_{A310}$, R = $R^{423}$, in $L_{A311}$, R = $R^{424}$,
in $L_{A312}$, R = $R^{425}$, in $L_{A313}$, R = $R^{426}$,
in $L_{A314}$, R = $R^{427}$, in $L_{A315}$, R = $R^{428}$,
in $L_{A316}$, R = $R^{429}$, in $L_{A317}$, R = $R^{430}$,
in $L_{A318}$, R = $R^{431}$, in $L_{A319}$, R = $R^{432}$, in L$_{A320}$, R = R$^{A33}$, in L$_{A321}$, R = R$^{A34}$,
in L$_{A322}$, R = R$^{A35}$, in L$_{A323}$, R = R$^{A36}$,
in L$_{A324}$, R = R$^{A37}$, in L$_{A325}$, R = R$^{A38}$,
in L$_{A326}$, R = R$^{A39}$, in L$_{A327}$, R = R$^{A40}$,
and in L$_{A328}$, R = R$^{A41}$;,
L$_{A329}$ through L$_{A369}$, each
represented by the formula

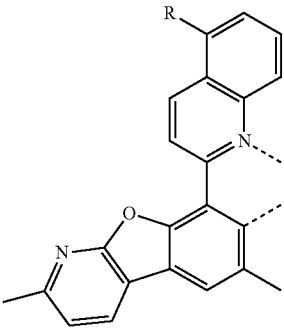

wherein
in L$_{A329}$, R = R$^{41}$, in L$_{A330}$, R = R$^{42}$,
in L$_{A331}$, R = R$^{43}$, in L$_{A332}$, R = R$^{44}$,
in L$_{A333}$, R = R$^{45}$, in L$_{A334}$, R = R$^{46}$,
in L$_{A335}$, R = R$^{47}$, in L$_{A336}$, R = R$^{48}$,
In L$_{A337}$, R = R$^{49}$, in L$_{A338}$, R = R$^{A10}$,
in L$_{A339}$, R = R$^{A11}$, in L$_{A340}$, R = R$^{A12}$,
in L$_{A341}$, R = R$^{A13}$, in L$_{A342}$, R = R$^{A14}$,
in L$_{A343}$, R = R$^{A15}$, in L$_{A344}$, R = R$^{A16}$,
in L$_{A345}$, R = R$^{A17}$, in L$_{A346}$, R = R$^{A18}$,
in L$_{A347}$, R = R$^{A19}$, in L$_{A348}$, R = R$^{A20}$,
in L$_{A349}$, R = R$^{A21}$, in L$_{A350}$, R = R$^{A22}$,
in L$_{A351}$, R = R$^{A23}$, in L$_{A352}$, R = R$^{A24}$,
in L$_{A353}$, R = R$^{A25}$, in L$_{A354}$, R = R$^{A26}$,
in L$_{A355}$, R = R$^{A27}$, in L$_{A356}$, R = R$^{A28}$,
in L$_{A357}$, R = R$^{A29}$, in L$_{A358}$, R = R$^{A30}$,
in L$_{A359}$, R = R$^{A31}$, in L$_{A360}$, R = R$^{A32}$,
in L$_{A361}$, R = R$^{A33}$, in L$_{A362}$, R = R$^{A34}$,
in L$_{A363}$, R = R$^{A35}$, in L$_{A364}$, R = R$^{A36}$,
in L$_{A365}$, R = R$^{A37}$, in L$_{A366}$, R = R$^{A38}$,
in L$_{A367}$, R = R$^{A39}$, in L$_{A368}$, R = R$^{A40}$,
and in LA$_{369}$, R = R$^{A41}$;,
L$_{A370}$ through L$_{A410}$, each
represented by the formula

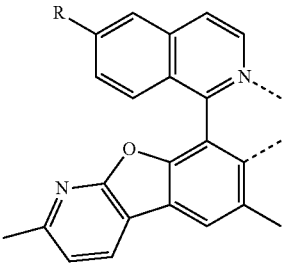

wherein
in L$_{A370}$, R = R$^{41}$, in L$_{A371}$, R = R$^{42}$,
in L$_{A372}$, R = R$^{43}$, in L$_{A373}$, R = R$^{44}$,
in L$_{A374}$, R = R$^{45}$, in L$_{A375}$, R = R$^{46}$,
in L$_{A376}$, R = R$^{47}$, in L$_{A377}$, R = R$^{48}$,
In L$_{A378}$, R = R$^{49}$, in L$_{A379}$, R = R$^{A10}$,
in L$_{A380}$, R = R$^{A11}$, in L$_{A381}$, R = R$^{A12}$,
in L$_{A382}$, R = R$^{A13}$, in L$_{A383}$, R = R$^{A14}$,
in L$_{A384}$, R = R$^{A15}$, in L$_{A385}$, R = R$^{A16}$,
in L$_{A386}$, R = R$^{A17}$, in L$_{A387}$, R = R$^{A18}$,
in L$_{A388}$, R = R$^{A19}$, in L$_{A389}$, R = R$^{A20}$,
in L$_{A390}$, R = R$^{A21}$, in L$_{A391}$, R = R$^{A22}$,
in L$_{A392}$, R = R$^{A23}$, in L$_{A393}$, R = R$^{A24}$,
in L$_{A394}$, R = R$^{A25}$, in L$_{A395}$, R = R$^{A26}$,
in L$_{A396}$, R = R$^{A27}$, in L$_{A397}$, R = R$^{A28}$,
in L$_{A398}$, R = R$^{A29}$, in L$_{A399}$, R = R$^{A30}$,
in L$_{A400}$, R = R$^{A31}$, in L$_{A401}$, R = R$^{A32}$, in L$_{A402}$, R = R$^{A33}$, in L$_{A403}$, R = R$^{A34}$,
in L$_{A404}$, R = R$^{A35}$, in L$_{A405}$, R = R$^{A36}$,
in L$_{A406}$, R = R$^{A37}$, in L$_{A407}$, R = R$^{A38}$,
in L$_{A408}$, R = R$^{A39}$, in L$_{A409}$, R = R$^{A40}$,
and in L$_{A410}$, R = R$^{A41}$;,
and
L$_{A411}$ through L$_{A451}$, each
represented by the formula

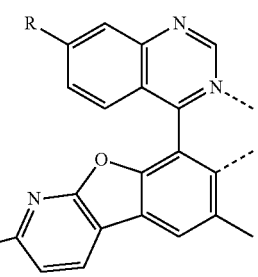

wherein
in L$_{A411}$, R = R$^{41}$, in L$_{A412}$, R = R$^{42}$,
in L$_{A413}$, R = R$^{43}$, in L$_{A414}$, R = R$^{44}$,
in L$_{A415}$, R = R$^{45}$, in L$_{A416}$, R = R$^{46}$,
in L$_{A417}$, R = R$^{47}$, in L$_{A418}$, R = R$^{48}$,
In L$_{A419}$, R = R$^{49}$, in L$_{A420}$, R = R$^{A10}$,
in L$_{A421}$, R = R$^{A11}$, in L$_{A422}$, R = R$^{A12}$,
in L$_{A423}$, R = R$^{A13}$, in L$_{A424}$, R = R$^{A14}$,
in L$_{A425}$, R = R$^{A15}$, in L$_{A426}$, R = R$^{A16}$,
in L$_{A427}$, R = R$^{A17}$, in L$_{A428}$, R = R$^{A18}$,
in L$_{A429}$, R = R$^{A19}$, in L$_{A430}$, R = R$^{A20}$,
in L$_{A431}$, R = R$^{A21}$, in L$_{A432}$, R = R$^{A22}$,
in L$_{A433}$, R = R$^{A23}$, in L$_{A434}$, R = R$^{A24}$,
in L$_{A435}$, R = R$^{A25}$, in L$_{A436}$, R = R$^{A26}$,
in L$_{A437}$, R = R$^{A27}$, in L$_{A438}$, R = R$^{A28}$,
in L$_{A439}$, R = R$^{A29}$, in L$_{A440}$, R = R$^{A30}$,
in L$_{A441}$, R = R$^{A31}$, in L$_{A442}$, R = R$^{A32}$,
in L$_{A443}$, R = R$^{A33}$, in L$_{A444}$, R = R$^{A34}$,
in L$_{A445}$, R = R$^{A35}$, in L$_{A446}$, R = R$^{A36}$,
in L$_{A447}$, R = R$^{A37}$, in L$_{A448}$, R = R$^{A38}$,
in L$_{A449}$, R = R$^{A39}$, in L$_{A450}$, R = R$^{A40}$,
and in L$_{A451}$, R = R$^{A41}$;, wherein, R$^{A1}$ through R$^{A41}$ have the formulas:

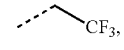 R$^{A1}$

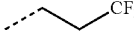 R$^{A2}$

 R$^{A3}$

 R$^{A4}$

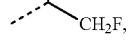 R$^{A5}$

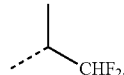 R$^{A6}$

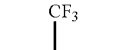

-continued
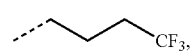 $R^{A7}$
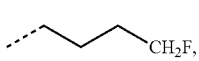 $R^{A8}$
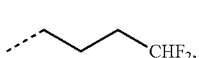 $R^{A9}$
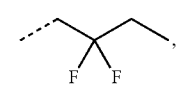 $R^{A10}$
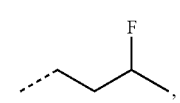 $R^{A11}$
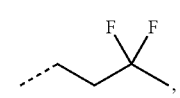 $R^{A12}$
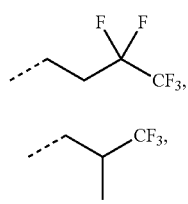 $R^{A13}$
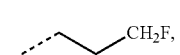 $R^{A14}$
 $R^{A15}$
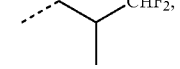 $R^{A16}$
 $R^{A17}$
 $R^{A18}$
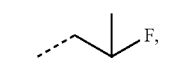 $R^{A19}$
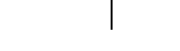 $R^{A20}$
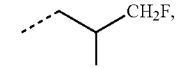 $R^{A21}$
-continued
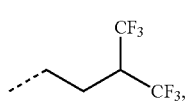 $R^{A22}$
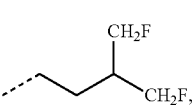 $R^{A23}$
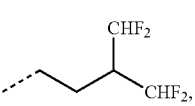 $R^{A24}$
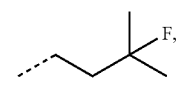 $R^{A25}$
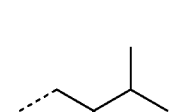 $R^{A26}$
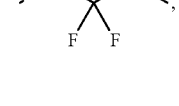 $R^{A27}$
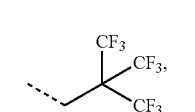 $R^{A28}$
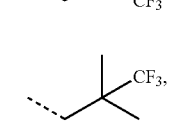 $R^{A29}$
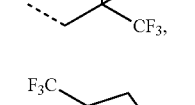 $R^{A30}$
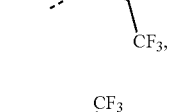 $R^{A31}$
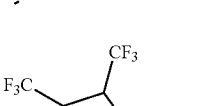 $R^{A32}$ -continued
R^{A33} 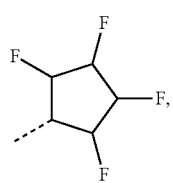
R^{A34} 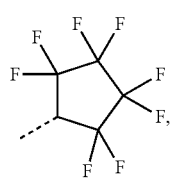
R^{A35} 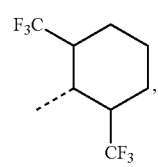
R^{A36} 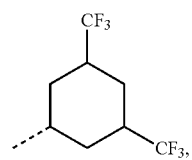
R^{A37} 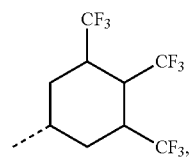
R^{A38} 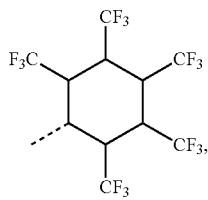
R^{A39} 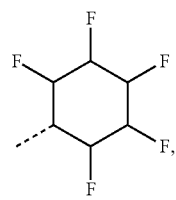
R^{A40} 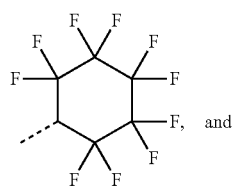 and
-continued
R^{A41} 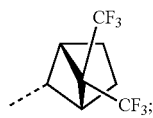
and
wherein $L^2$ is selected from the group consisting of:
$L_{B1}$ 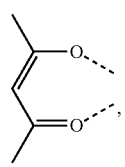
$L_{B2}$ 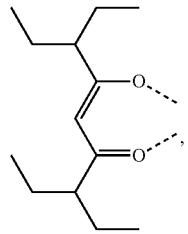
$L_{B3}$ 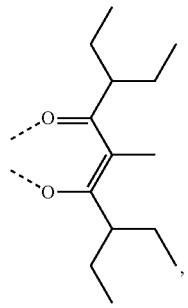
$L_{B4}$ 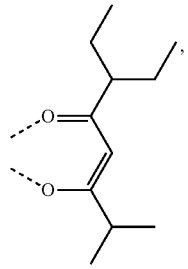
$L_{B5}$ 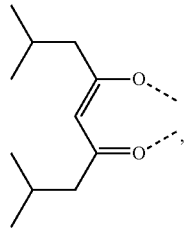

165
-continued $L_{B6}$ 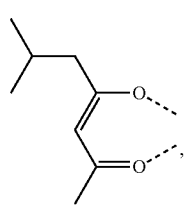

$L_{B7}$ 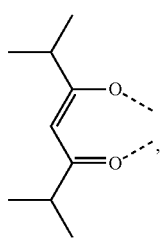

$L_{B8}$ 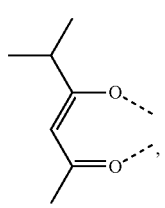

$L_{B9}$ 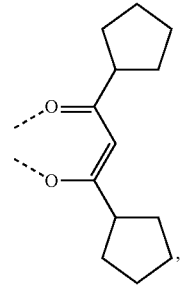

$L_{B10}$ 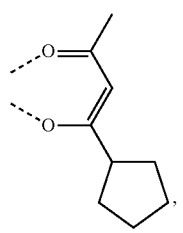

$L_{B11}$ 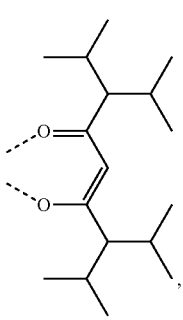

166
-continued $L_{B12}$ 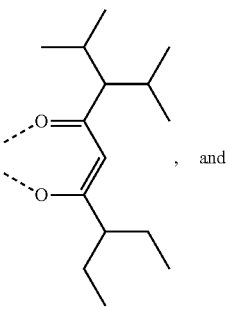, and $L_{B13}$ 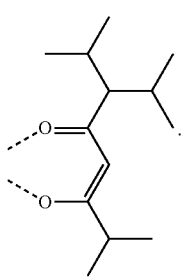.

15. The compound of claim 14, wherein the first compound is selected from the group consisting of Compound 1 through Compound 5,863; and
wherein each of Compound x, where x=451j+k−451, k is an integer from 1 to 451, and j is an integer from 1 to 13, has the formula Ir($L_{Ak}$)$_2$($L_{Bj}$).

16. The composition of claim 1, wherein the first compound is selected from the group consisting of Compound 453
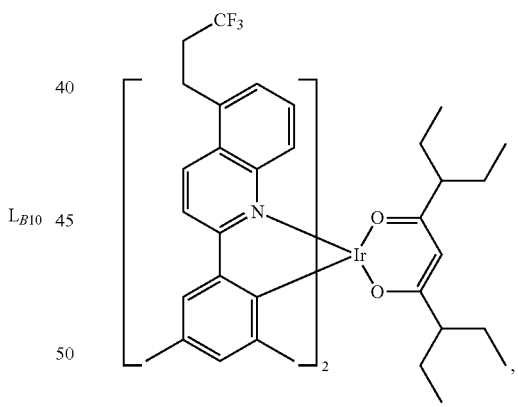

Compound 781
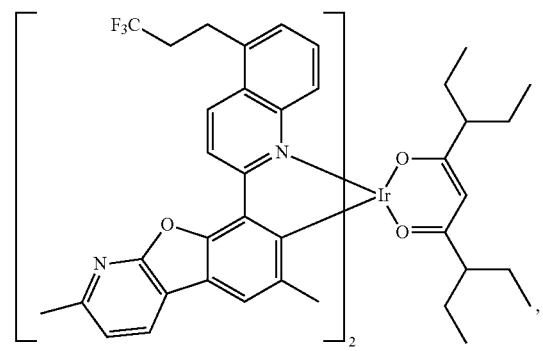

Compound 699

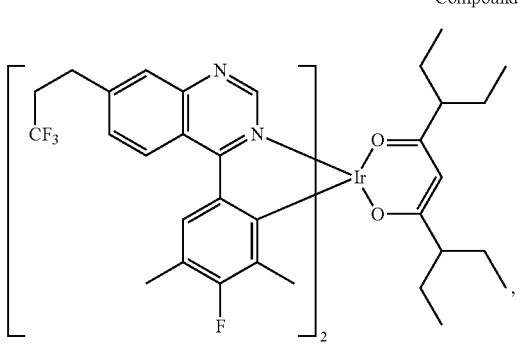

Compound 22

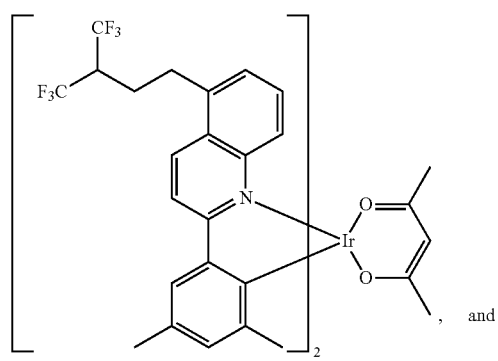, and

Compound 473

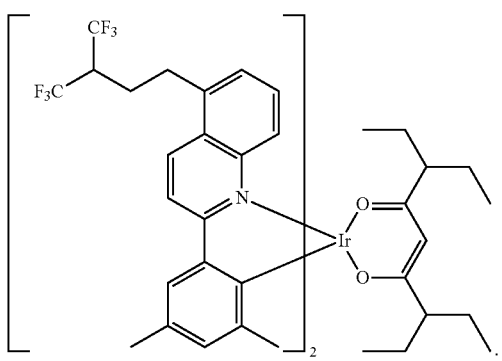.

17. A first device comprising a first organic light emitting device, the first organic light emitting device comprising:
an anode;
a cathode; and
an organic layer, disposed between the anode and the cathode,
comprising a first compound, wherein the first compound has the formula of $M(L^1)_x(L^2)_y(L^3)_z$;
wherein M is selected from the group consisting of Ir, Rh, Re, Ru, Os, Pt, Au, and Cu;
wherein $L^1$, $L^2$, and $L^3$ can be the same or different;
wherein x is 1, 2, or 3;
wherein y is 0, 1, or 2;
wherein z is 0, 1, or 2;
wherein x+y+z is the oxidation state of the metal M;
wherein $L^1$, $L^2$, and $L^3$ are each independently selected from the group consisting of:

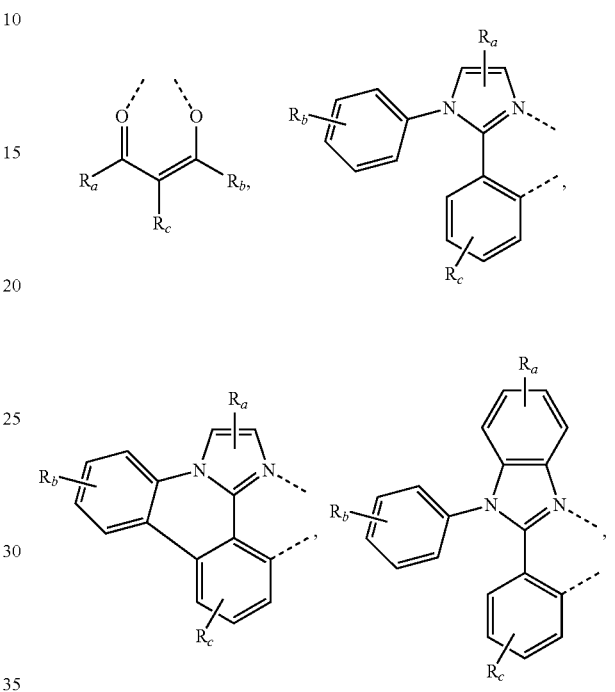

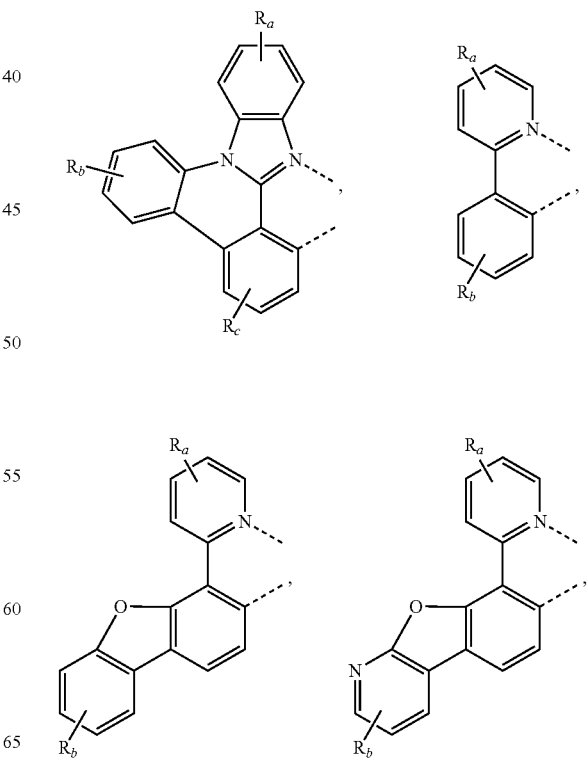

-continued

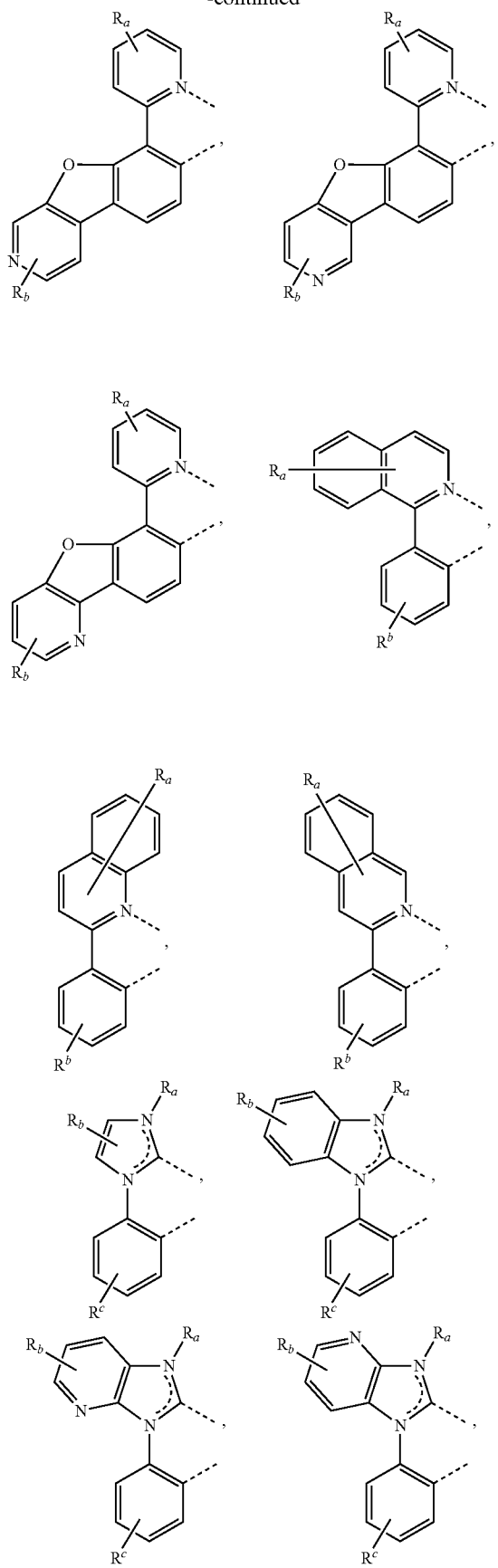
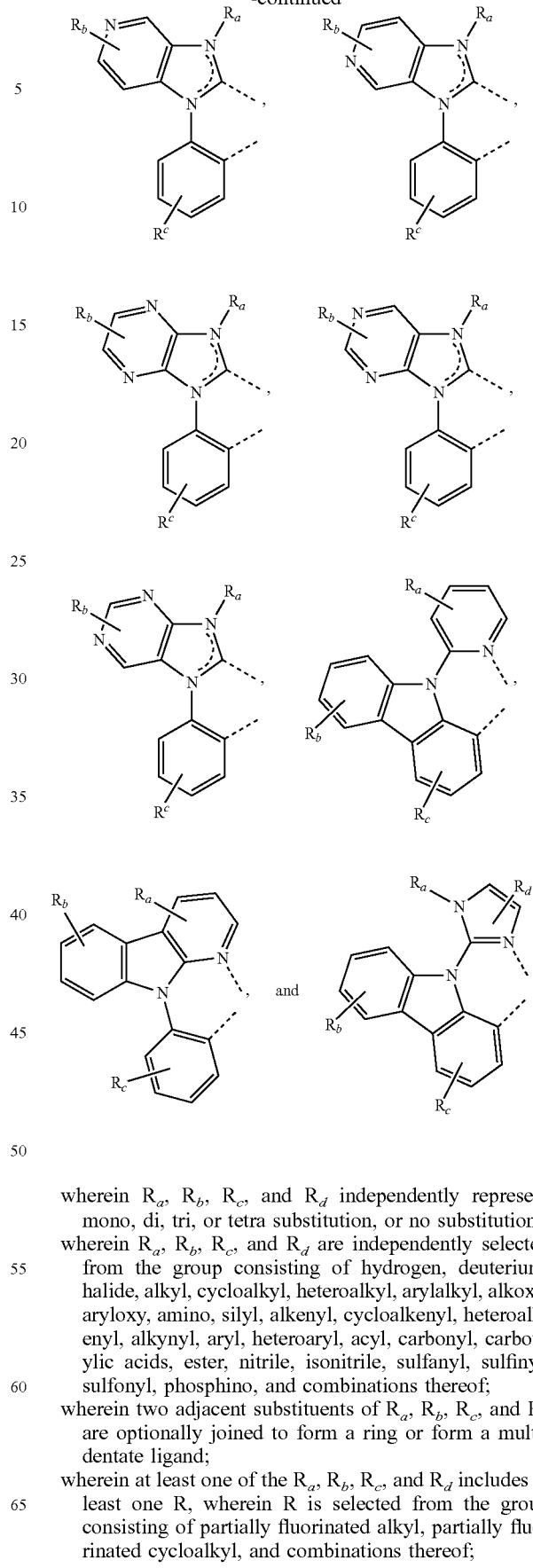

wherein $R_a$, $R_b$, $R_c$, and $R_d$ independently represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, $R_c$, and $R_d$ are optionally joined to form a ring or form a multidentate ligand;

wherein at least one of the $R_a$, $R_b$, $R_c$, and $R_d$ includes at least one R, wherein R is selected from the group consisting of partially fluorinated alkyl, partially fluorinated cycloalkyl, and combinations thereof;

wherein each of the at least one R is directly bonded to an aromatic ring;
wherein in each of the at least one R, C having an F attached thereto is separated by at least one carbon atom from the aromatic ring; and
wherein if one of $L^1$, $L^2$, and $L^3$ is

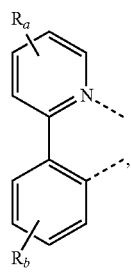

then at least one of the other $L^1$, $L^2$, and $L^3$ is different.

18. The first device of claim 17, wherein the first compound is selected from the group consisting of

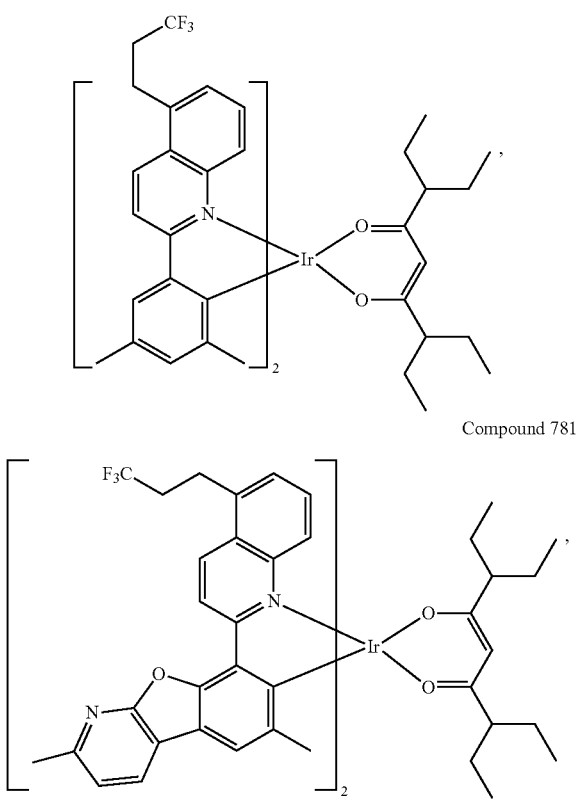

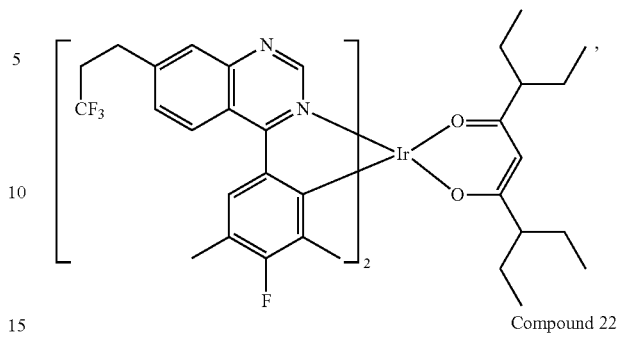

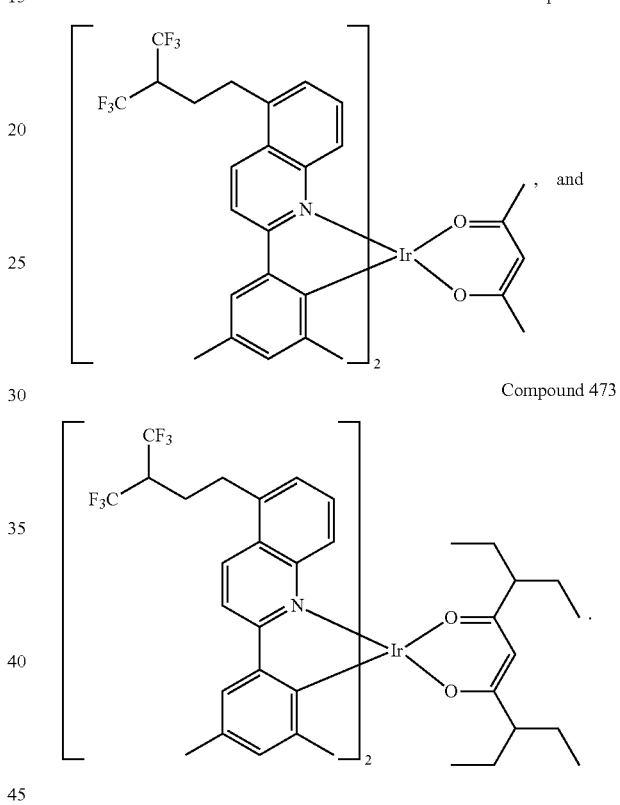

19. The first device of claim 17, wherein the first device is a consumer product selected from the group consisting of flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a wall, theater or stadium screen, and a sign.

* * * * *

UNITED STATES PATENT AND TRADEMARK OFFICE
CERTIFICATE OF CORRECTION

PATENT NO.         : 9,799,838 B2
APPLICATION NO.    : 15/177906
DATED              : October 24, 2017
INVENTOR(S)        : Pierre-Luc T. Boudreault, Walter Yeager and Chuanjun Xia Page 1 of 1

It is certified that error appears in the above-identified patent and that said Letters Patent is hereby corrected as shown below:

In the Claims

In Claim 7, Column 143, Lines 23-35, please delete

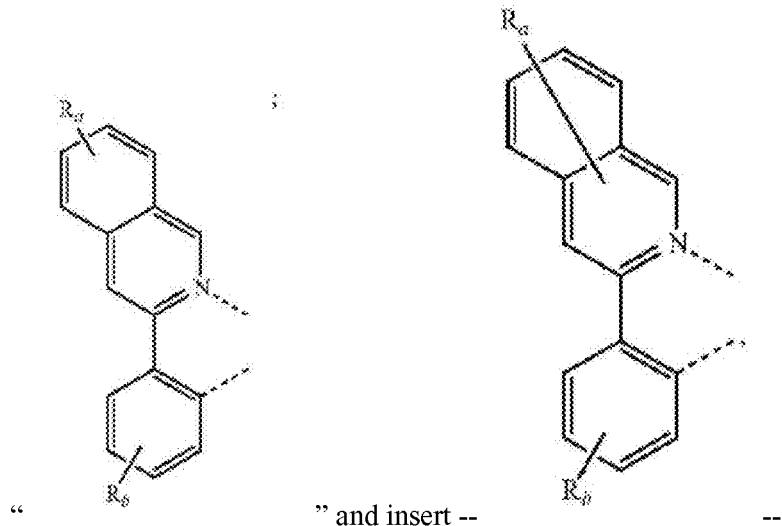

" and insert -- --

Signed and Sealed this
Fifth Day of December, 2017

Joseph Matal
*Performing the Functions and Duties of the
Under Secretary of Commerce for Intellectual Property and
Director of the United States Patent and Trademark Office*